United States Patent
Freimoser-Grundschober et al.

(10) Patent No.: US 9,156,913 B2
(45) Date of Patent: Oct. 13, 2015

(54) ANTI-TENASCIN-C A2 ANTIBODIES AND METHODS OF USE

(75) Inventors: Anne Freimoser-Grundschober, Zurich (CH); Ralf Hosse, Cham (CH); Christian Klein, Bonstetten (CH); Ekkehard Moessner, Kreuzlingen (CH); Valeria G. Nicolini, Erlenbach (CH); Pablo Umaña, Waedenswil (CH)

(73) Assignee: Roche Glycart AG, Schlieren (CH)

( * ) Notice: Subject to any disclaimer, the term of this patent is extended or adjusted under 35 U.S.C. 154(b) by 100 days.

(21) Appl. No.: 13/207,705

(22) Filed: Aug. 11, 2011

(65) Prior Publication Data

US 2012/0039807 A1 Feb. 16, 2012

(30) Foreign Application Priority Data

Aug. 13, 2010 (EP) .................................. 10172841

(51) Int. Cl.
*C07K 16/30* (2006.01)
*A61K 47/48* (2006.01)
*C07K 16/00* (2006.01)
*C12P 21/08* (2006.01)

(52) U.S. Cl.
CPC ........... *C07K 16/30* (2013.01); *A61K 47/48569* (2013.01); *C07K 2317/41* (2013.01); *C07K 2317/55* (2013.01); *C07K 2317/72* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2009/0208500 A1* | 8/2009 | Joly et al. .................... | 424/134.1 |
| 2011/0064751 A1* | 3/2011 | Mossner et al. ........... | 424/178.1 |
| 2011/0294985 A1 | 12/2011 | Fukai et al. | |

FOREIGN PATENT DOCUMENTS

| | | |
|---|---|---|
| WO | 99/54342 | 10/1999 |
| WO | 02/079255 A1 | 10/2002 |
| WO | 2009/049841 | 4/2009 |
| WO | 2009/089998 A1 | 7/2009 |
| WO | 2011/020783 A2 | 2/2011 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Chen et al., "Selection and analysis of an optimized anti-VEGF anitbody: crystal structure of an affinity-matured Fab in complex with antigen" J Mol Biol. 293(4):865-81 (1999).
Navazo et al., "The altervatively spliced domain TnFnIII A1A2 of the extracellular matrix protein tenascin-C suppresses activation-induced T lymphocyte proliferation and cytokine production" J Immunol 167(11):6431-40 (Dec. 2001).
Schliemann et al., "Three clinical-stage tumor targeting antibodies reveal differential expression of oncofetal fibronectin and tenasicin-C isoforms in human lymphoma" Leuk Res. 33(12):1718-22 (Dec. 2009).
PCT ISR dated Oct. 27, 2011 for PCT/EP2011/063734.
Ferrara et al., "Modulation of therapeutic antibody effector funtions by glycosylation engineering: influence of Golgi enzyme localization domain and co-expression of heterologous betal, 4-N-acetylglucosaminyltransferase III and Golgi alpha-mannosidase II" 93(5):861 (2006).

* cited by examiner

*Primary Examiner* — Hong Sang
(74) *Attorney, Agent, or Firm* — Roche Glycart AG

(57) ABSTRACT

The invention provides antibodies against the A2 domain of tenascin-C and methods of using the same.

18 Claims, 23 Drawing Sheets

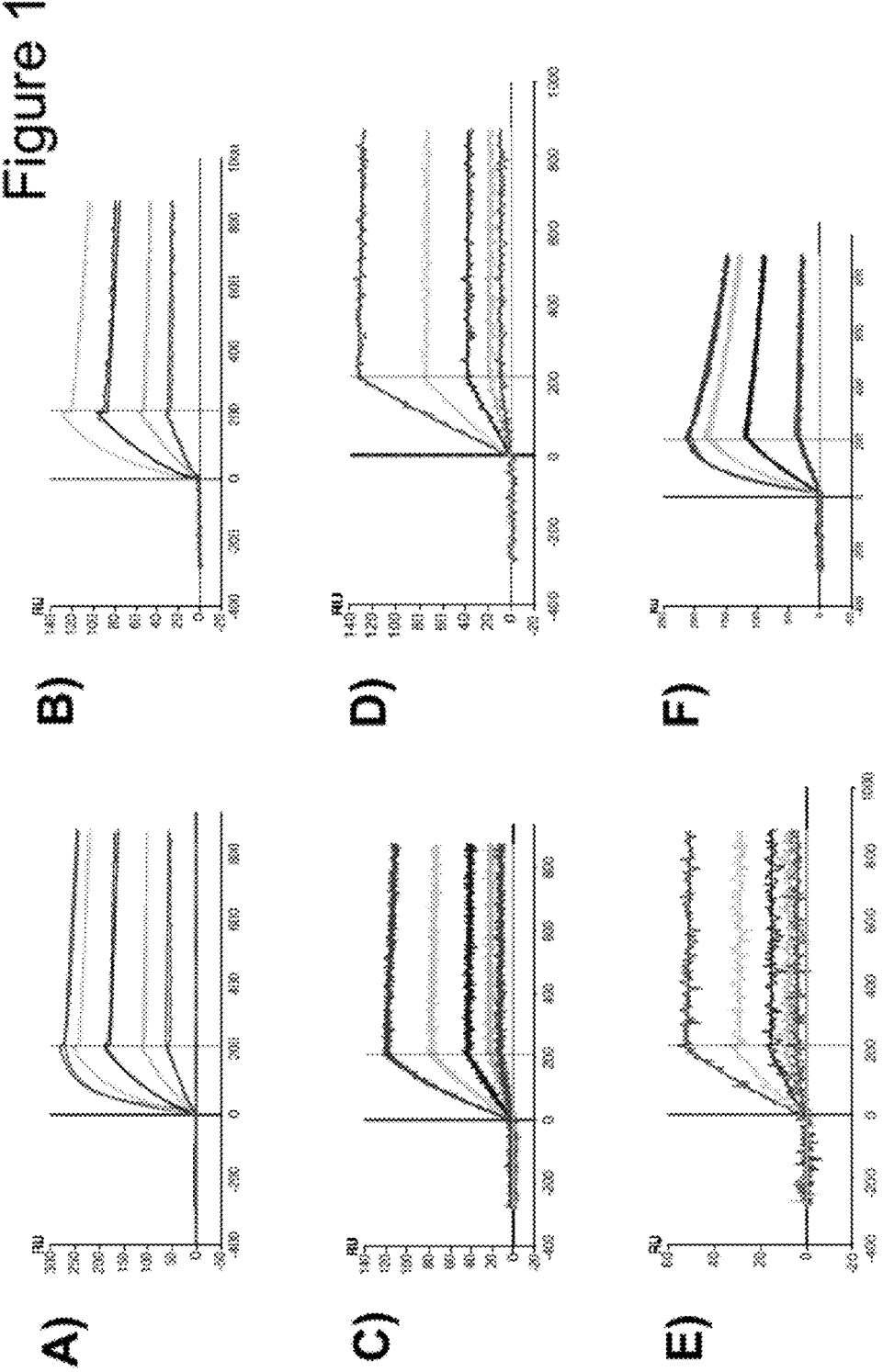

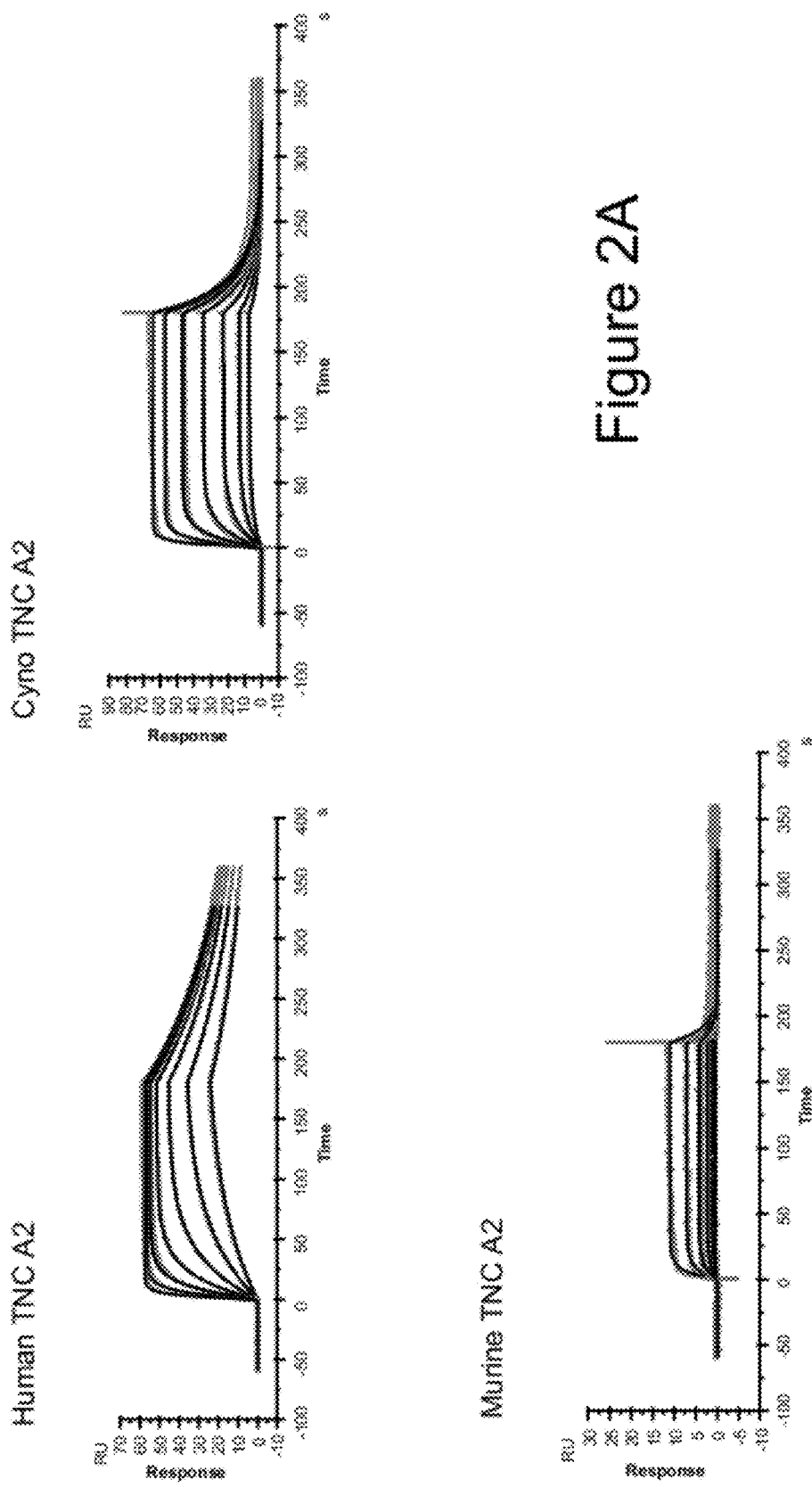

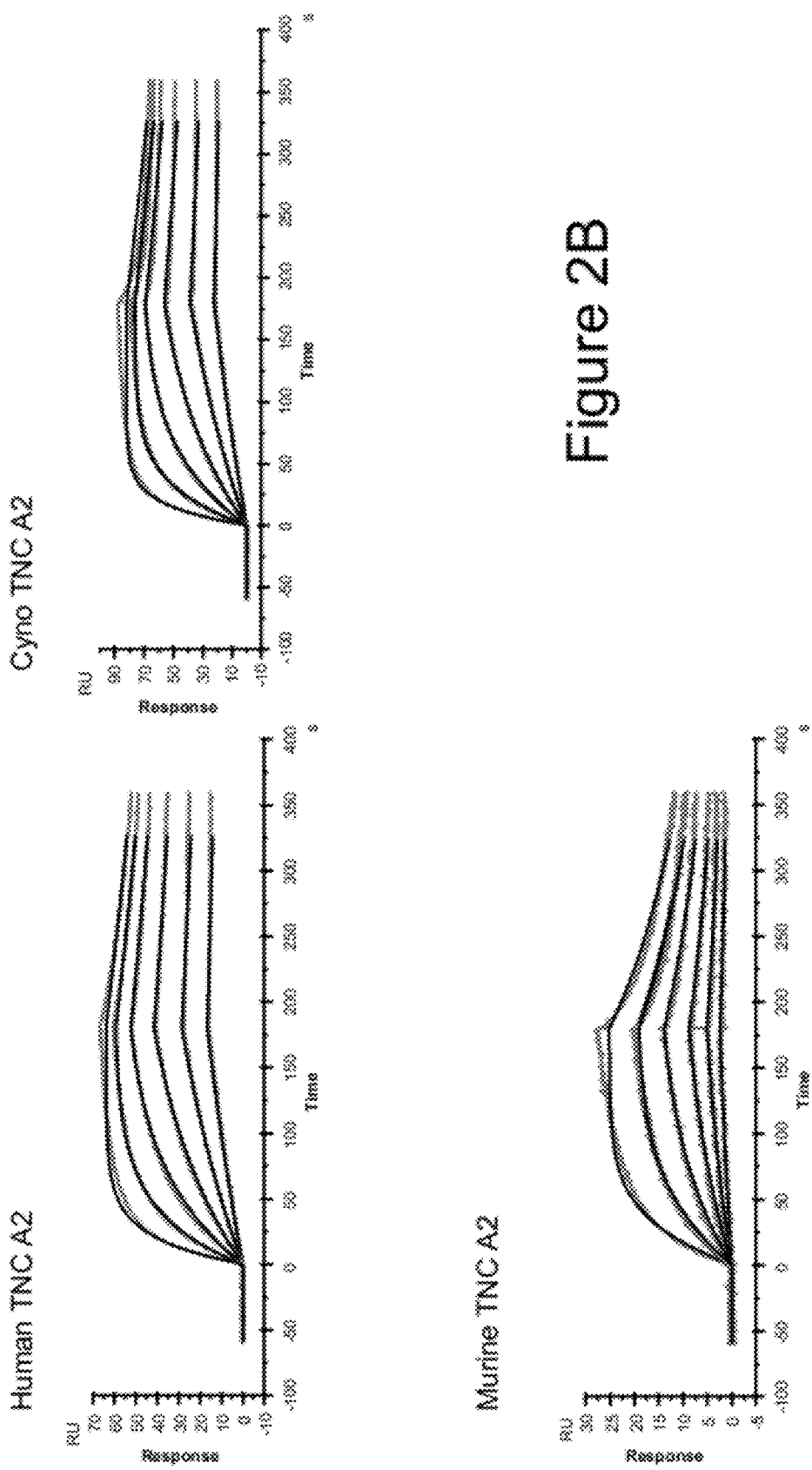

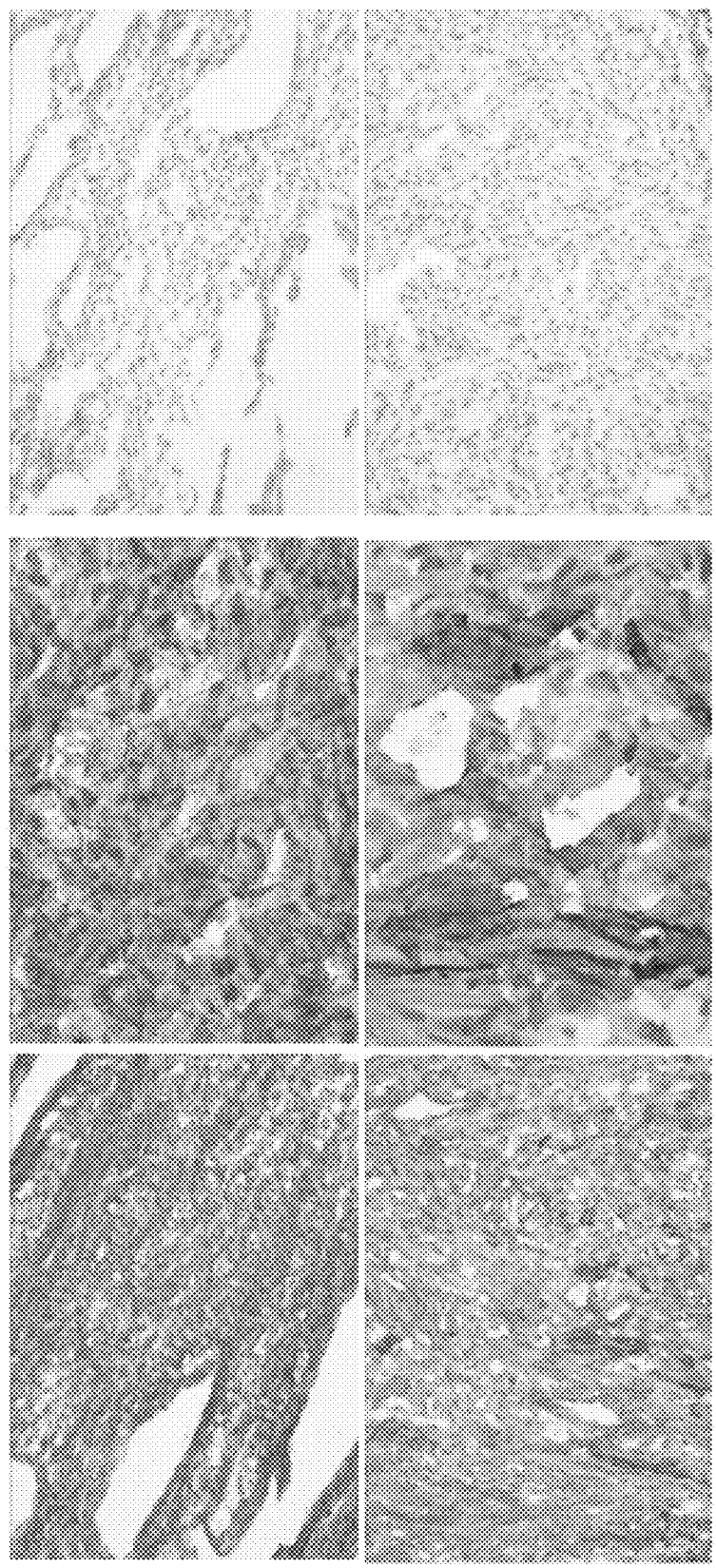

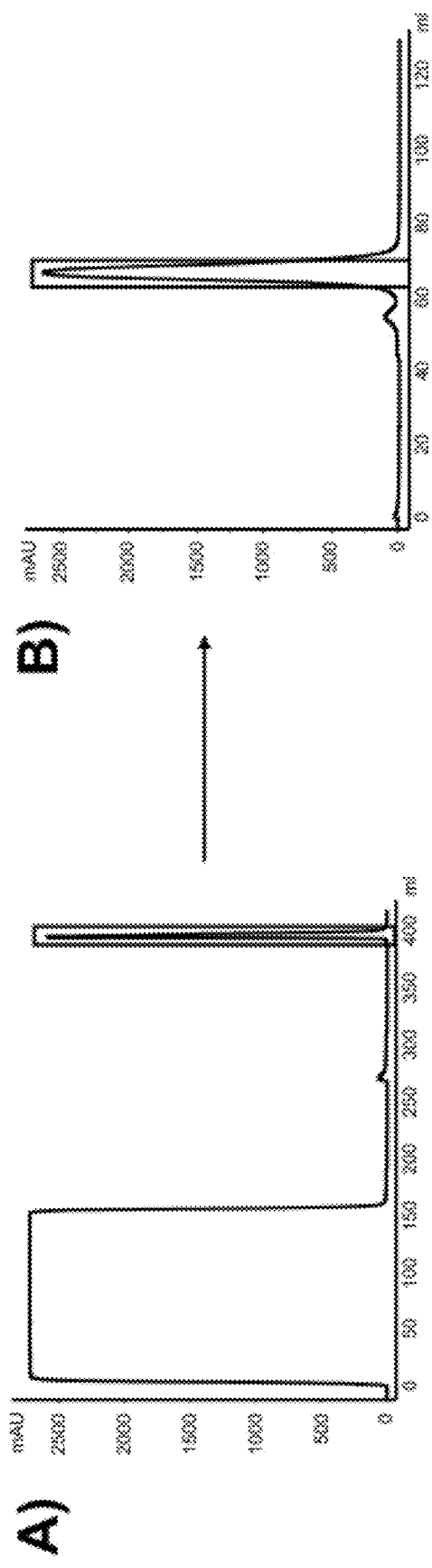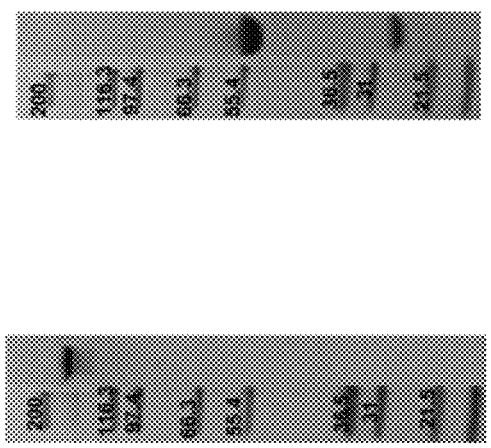
Figure 6

ANTI-TENASCIN-C A2 ANTIBODIES AND METHODS OF USE

CROSS-REFERENCE to RELATED APPLICATIONS

This application claims the benefit of the filing date of European patent application EP10172841.8 filed Aug. 13, 2010, the contents of which are hereby incorporated by reference in its entirety.

FIELD OF THE INVENTION

The present invention relates to antibodies specific for the A2 domain of tenascin-C (TNC A2). In addition, the invention relates to polynucleotides encoding such antibodies, and vectors and host cells comprising such polynucleotides. The invention further relates to methods for producing the antibodies and methods of using them in the treatment of disease.

BACKGROUND

Tenascin C and Anti-Tenascin C Antibodies

Tenascins are a highly conserved family of large multimeric extracellular matrix (ECM) glycoproteins, which is found in vertebrates. Four tenascin paralogues have been identified in mammals, termed tenascin-C, tenascin-R, tenascin-X and tenascin-W. Tenascin family proteins have a common primary structure, comprising N-terminal heptad repeats, epidermal growth factor (EGF)-like repeats, fibronectin type III domain repeats and a C-terminal fibrinogen-like globular domain. Via an N-terminal oligomerization domain, individual subunits assemble into trimers or, as is the case for tenascin-C, even hexamers.

Mammalian tenascin-C monomers typically have 14.5 EGF-like repeats and 8 fibronectin type III domain repeats that are shared by all tenascin-C isoforms. However, up to 9 additional fibronectin type III domain repeats (domains A1 to D) can be independently included or excluded by alternative splicing, giving rise to a large number of tenascin-C isoforms (see e.g. Hsia and Schwarzbauer, J Biol Chem 280, 26641-26644 (2005)).

Tenascin-C is transiently expressed in the developing embryo, but virtually absent from adult tissues. It reappears, however, in tissues undergoing remodeling processes, including certain pathological conditions such as wound healing, inflammation and cancer (reviewed in Chiquet-Ehrismann & Chiquet, J Pathol 200, 488-499 (2003)).

Importantly, tenascin-C is highly expressed in the majority of malignant solid tumors, including tumors of the brain, breast, colon, lung, skin and other organs (reviewed in Orend and Chiquet-Ehrismann, Cancer Letters 244, 143-163 (2006)), where it may be expressed by transformed epithelial cells as well as stromal cells in the tumor microenvironment (Yoshida et al., J Pathol 182, 421-428 (1997), Hanamura et al., Int J Cancer 73, 10-15 (1997)). In particular, the "large isoform" of tenascin-C, containing the alternatively spliced domains A1 to D, is expressed in invasive carcinomas while being nearly undetectable in healthy adult tissues (Borsi et al., Int J Cancer 52, 688-692 (1992), Carnemolla et al., Eur J Biochem 205, 561-567 (1992)). Its expression pattern makes tenascin-C, in particular its alternatively spliced domains, a promising antigen for tumor targeting applications, and accordingly a number of antibodies against several domains of the protein have been developed (see e.g. Brack et al., Clin Cancer Res 12, 3200-3208 (2006) or EP 1 817 345, describing antibodies against the A1 domain of tenascin-C; Silacci et al., Prot Eng Des Sel 19, 471-478 (2006), or EP 1 173 766, describing antibodies against the C domain of tenascin-C; Wang et al., Hybridoma 29, 13-16 (2010), describing an antibody against the D domain of tenascin C; or Balza et al., FEBS 332, 39-43 (1993), describing several antibodies against different domains of human tenascin). Recently, also an antibody recognizing a specific epitope in the A2 domain of human tenascin-C has been described (WO 2009/089998).

Antibody Glycosylation

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions (Jenkins et al., Nature Biotechnol 14, 975-81 (1996)).

IgG1 type antibodies, the most commonly used antibodies in cancer immunotherapy, are glycoproteins that have a conserved N-linked glycosylation site at Asn 297 in each CH2 domain. The two complex biantennary oligosaccharides attached to Asn 297 are buried between the CH2 domains, forming extensive contacts with the polypeptide backbone, and their presence is essential for the antibody to mediate effector functions such as antibody dependent cell-mediated cytotoxicity (ADCC) (Lifely et al., Glycobiology 5, 813-822 (1995); Jefferis et al., Immunol Rev 163, 59-76 (1998); Wright and Morrison, Trends Biotechnol 15, 26-32 (1997)). Protein engineering studies have shown that FcγRs interact with the lower hinge region of the IgG CH2 domain. Lund et al., *J. Immunol.* 157:4963-69 (1996). However, FcγR binding also requires the presence of the oligosaccharides in the CH2 region. Lund et al., *J. Immunol.* 157:4963-69 (1996); Wright and Morrison, *Trends Biotech.* 15:26-31 (1997), suggesting that either oligosaccharide and polypeptide both directly contribute to the interaction site or that the oligosaccharide is required to maintain an active CH2 polypeptide conformation. Modification of the oligosaccharide structure can therefore be explored as a means to increase the affinity of the interaction between IgG1 and FcγR, and to increase ADCC activity of IgG1s.

A way to obtain large increases in the potency of monoclonal antibodies, is to enhance their natural, cell-mediated effector functions by engineering their oligosaccharide component as described in Umaña et al., Nat Biotechnol 17, 176-180 (1999) and U.S. Pat. No. 6,602,684 (WO 99/54342), the contents of which are hereby incorporated by reference in their entirety. Umaña et al. showed that overexpression of β(1,4)-N-acetylglucosaminyltransferase III (GnTIII), a glycosyltransferase catalyzing the formation of bisected oligosaccharides, in Chinese hamster ovary (CHO) cells significantly increases the in vitro ADCC activity of antibodies produced in those cells. Overexpression of GnTIII in production cell lines leads to antibodies enriched in bisected oligosaccharides, which are generally also non-fucosylated and of the hybrid type. If in addition to GnTIII, mannosidase II (ManII) is overexpressed in production cell lines, antibodies enriched in bisected, non-fucosylated oligosaccharides of the complex type are obtained (Ferrara et al., Biotechn Bioeng 93, 851-861 (2006)). Both types of antibodies show strongly enhanced ADCC, as compared to antibodies with unmodified glycans, but only antibodies in which the majority of the N-glycans are of the complex type are able to induce significant complement-dependent cytotoxicity (Ferrara et al., Biotechn Bioeng 93, 851-861 (2006)). Alterations in the composition of the Asn 297 carbohydrate or its elimination also affect binding of the antibody Fc-domain to Fcγ-receptor (FcγR) and complement C1q protein, which is important for ADCC and CDC, respectively (Umaña et al., Nat Biotechnol 17, 176-180 (1999); Davies et al., Biotechnol Bioeng 74, 288-294 (2001); Mimura et al., J Biol Chem 276, 45539-45547 (2001); Radaev et al., J Biol Chem 276, 16478-16483 (2001); Shields et al., J Biol Chem 276, 6591-6604 (2001); Shields et al., J Biol Chem 277, 26733-26740 (2002); Simmons et al., J Immunol Methods 263, 133-147 (2002)).

BRIEF SUMMARY OF THE INVENTION

The present invention provides antibodies that specifically bind to the A2 domain of tenascin-C, having a high affinity and/or enhanced effector function.

In one aspect, the invention is directed to an antibody that specifically binds to TNC A2, comprising at least one (i.e. one, two, three, four, five or six) of the complementarity determining regions (CDRs) set forth in SEQ ID NOs 3, 5, 7, 9, 11, 13, 15, 17, 19, 21, 23, 25, 27, 29, 31, 33, 35, 37, 39, 41, 43, 45 and 47. In one embodiment, the antibody comprises three heavy chain CDRs (i.e. HCDR1, HCDR2, and HCDR3) and/or three light chain CDRs (i.e. LCDR1, LCDR2, and LCDR3) selected from SEQ ID NOs 3, 5, 7, 9, 11, 13, 15, 17, 19, 21, 23, 25, 27, 29, 31, 33, 35, 37, 39, 41, 43, 45 and 47. In a more particular embodiment, the antibody comprises an antibody heavy chain variable region and/or an antibody light chain variable region, particularly both a heavy and light chain variable region, selected from the heavy and light chain variable region sequences set forth in SEQ ID NOs 55, 57, 59, 61, 63, 65, 67, 69, 71, 73, 75, 77, 79, 81, 83, 85, 87, 89 and 91. In one embodiment, the antibody comprises an Fc region, particularly an IgG Fc region. In a further embodiment, the antibody is a full-length antibody, particularly an IgG class antibody. In another embodiment, the antibody comprises a human antibody constant region. In one embodiment, the antibody is human. In one embodiment, the antibody is glycoengineered to have modified oligosaccharides in the Fc region. In one embodiment the antibody has an increased proportion of non-fucosylated and/or bisected oligosaccharides in the Fc region, as compared to a non-glycoengineered antibody. In a further embodiment, the antibody has increased effector function and/or increased Fc receptor binding affinity. In a particular embodiment, the increased effector function is increased antibody-dependent cell-mediated cytotoxicity (ADCC). In another embodiment the antibody binds to human TNC A2 with a $K_D$ value of lower than about 1 μM, preferably lower than about 100 nM, most preferably lower than about 1 nM. In one embodiment, the antibody is affinity matured. In one embodiment, the antibody binds to TNC A2 in human tissues.

In other aspects, the invention is also directed to polypeptides, polynucleotides, host cells, and expression vectors related to the antibodies. In a further aspect, the invention relates to methods of making the antibodies. In a further aspect, the invention is directed to methods of using the antibodies, particularly for the treatment of diseases characterized by expression of TNC A2, such as cancer.

BRIEF DESCRIPTION OF THE FIGURES

FIG. 1 shows Surface Plasmon Resonance (SPR)-based kinetic analyses of affinity-matured anti-TNC A2 Fab fragments binding to human (hu) TNC A2. Processed kinetic data sets are presented for clone 2B10_C3B6 (A), clone 2B10_6A12 (B), clone 2B10_C3A6 (C), clone 2B10_O7D8 (D), clone 2B10_O1F7 (E) and clone 2B10_6H10 (F). Smooth lines represent a global fit of the data to a 1:1 interaction model.

FIG. 2 (A) shows SPR-based kinetic analyses of 2B10 anti-TNC A2 Fab fragments binding to human, murine and cynomolgus TNC A2. Panel (B) shows SPR-based kinetic analyses of 2B10 anti-TNC A2 human IgG binding to human, murine and cynomolgus TNC A2, as described in Example 7.

FIG. 6 shows the purification and analysis of the wild-type 2B10 human IgG. A) Protein A affinity chromatography purification step. B) Size exclusion chromatography purification step. C) Analytical SDS PAGE. Experimental producers are described in Example 1.

DETAILED DESCRIPTION OF EMBODIMENTS OF THE INVENTION

I. Definitions

Figure 3A:
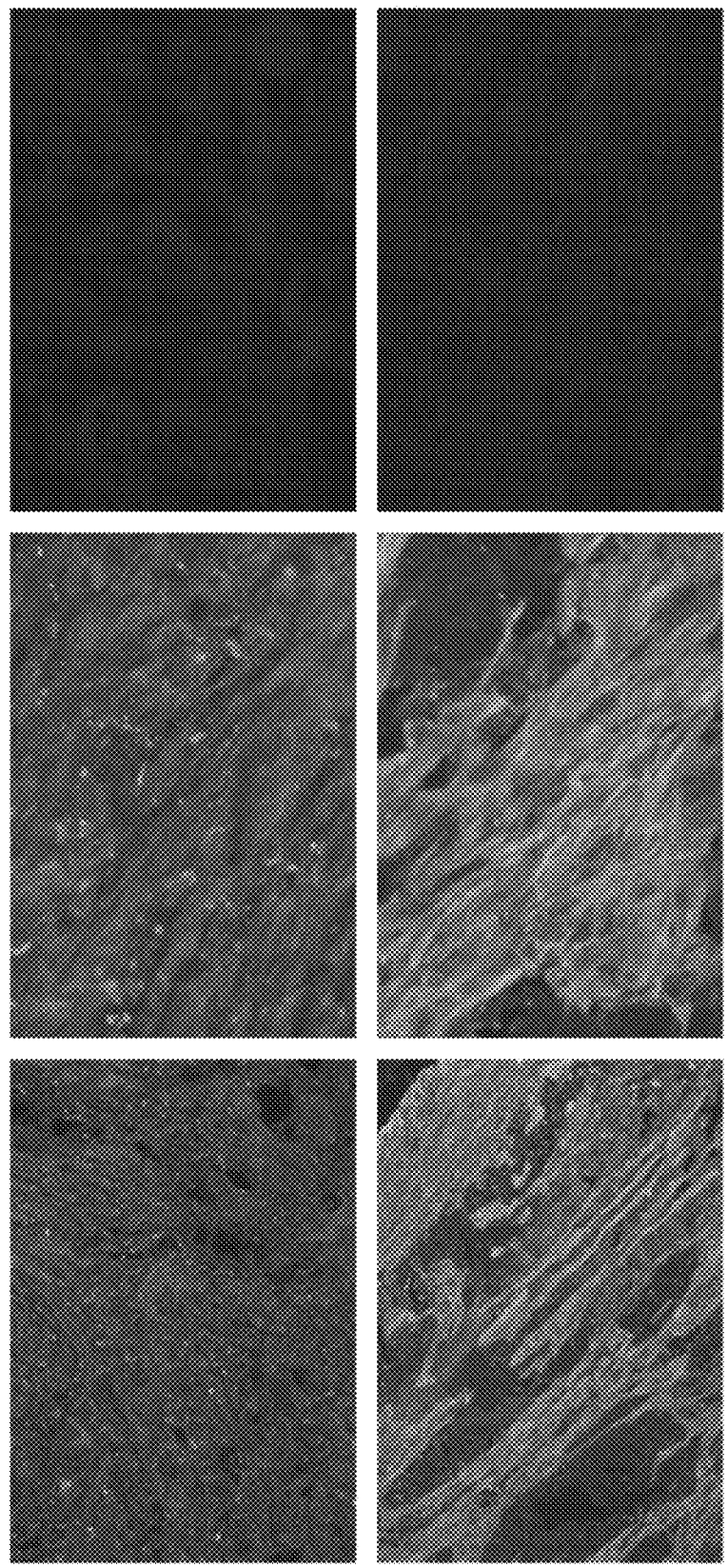
FIG. 3(A) shows immunohistochemical images of normal (upper panels) and tumor (lower panels) human uterus tissue at 100× (left panels) and 400× (middle panels) magnification as stained with 2B10 variable region in a Fab fragment fused to a FLAG fragment (SHD2B10-FLAG). Right panels: control, 100× magnification. (B) shows the expression levels of TNC A2 in various human tissue samples in terms of % of immunofluorescence surface area as stained with 2B10 variable region in a Fab fragment fused to a FLAG fragment (SHD2B10-FLAG). Various human tissue samples from healthy individuals and cancer patients were stained with the SHD2B10-FLAG Fab fragment as described in Example 8.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. Specific illustrative and exemplary embodiments for measuring binding affinity are described in the following.

An "affinity matured" antibody refers to an antibody with one or more alterations (e.g. amino acid mutations) in one or more hypervariable regions (HVRs) (e.g. CDRs), compared to a parent antibody which does not possess such alterations, such alterations resulting in an improvement in the affinity of the antibody for antigen. Typically, the affinity matured antibody binds to the same epitope as the parent antibody.

The terms "anti-TNC A2 antibody" and "an antibody that binds to the A2 domain of Tenascin-C" refer to an antibody that is capable of binding TNC A2 with sufficient affinity such that the antibody is useful as a diagnostic and/or therapeutic agent in targeting TNC A2. In one embodiment, the extent of binding of an anti-TNC A2 antibody to an unrelated, non-TNC A2 protein is less than about 10% of the binding of the antibody to TNC A2 as measured, e.g., by a radioimmunoassay (RIA). In certain embodiments, an antibody that binds to TNC A2 has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-TNC A2 antibody binds to an epitope of TNC A2 that is conserved among TNC A2 from different species.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity. Also included are antibody fragments having an Fc region, and fusion proteins that comprise a region equivalent to the Fc region of an immunoglobulin.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, single-chain antibody molecules (e.g. scFv), diabodies, and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein. The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "chimeric" antibody refers to an antibody in which a portion of the heavy and/or light chain is derived from a particular source or species, while the remainder of the heavy and/or light chain is derived from a different source or species. For chimeric antibodies, for example, the non-antigen binding components may be derived from a wide variety of species, including primates such as chimpanzees and humans. Humanized antibodies are a particularly preferred form of chimeric antibodies.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below. "Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; cytokine secretion; immune-complex-mediated antigen uptake by antigen presenting cells; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al.,

*Sequences of Proteins of Immunological Interest*, 5th Ed. Public Health Service, National Institutes of Health, Bethesda, Md., 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)). "Framework" or "FR" refers to variable domain residues other than hypervariable region (HVR) (or CDR) residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In one embodiment, the host cell is engineered to allow the production of an antibody with modified oligosaccharides. In certain embodiments, the host cells have been further manipulated to express increased levels of one or more polypeptides having $\beta(1,4)$-N-acetylglucosaminyltransferase III (GnTIII) activity. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

CDRs also comprise "specificity determining residues," or "SDRs," which are residues that contact antigen. SDRs are contained within regions of the CDRs called abbreviated-CDRs, or a-CDRs. In general, only one-fifth to one-third of the residues in a given CDR participate in antigen binding. The specificity-determining residues in a particular CDR can be identified by, for example, computation of interatomic contacts from three-dimensional modeling and determination of the sequence variability at a given residue position in accordance with the methods described in Padlan et al., *FASEB J.* 9(1):133-139 (1995). Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (see Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "antibody conjugate" is an antibody conjugated to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For review of methods for assessment of antibody purity, see, e.g., Flatman et al., *J. Chromatogr. B* 848:79-87 (2007).

An "isolated" polynucleotide refers to a polynucleotide molecule that has been separated from a component of its natural environment. An isolated polynucleotide includes a polynucleotide molecule contained in cells that ordinarily contain the polynucleotide molecule, but the polynucleotide molecule is present extrachromosomally or at a chromosomal location that is different from its natural chromosomal location.

"Isolated polynucleotide encoding an anti-TNC A2 antibody" refers to one or more polynucleotide molecules encoding antibody heavy and light chains (or fragments thereof), including such polynucleotide molecule(s) in a single vector or separate vectors, and such polynucleotide molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The light chain of an antibody may be assigned to one of two types, called kappa (κ) and lambda (λ), based on the amino acid sequence of its constant domain.

"No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount selected from the group consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

The term "package insert" is used to refer to instructions customarily included in commercial packages of therapeutic products, that contain information about the indications, usage, dosage, administration, combination therapy, contraindications and/or warnings concerning the use of such therapeutic products.

The term "parent" antibody refers to an antibody that is used as the starting point or basis for the preparation of a variant.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software.

Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program. Similarly, by a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide or polypeptide is at least 80%, 85%, 90%, 95%, 96%, 97%, 98% or 99% identical to a nucleotide sequence or polypeptide sequence of the present invention can be determined conventionally using known computer programs, such as the ones listed above.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "A2 domain of tenascin-C (TNC A2)" as used herein, refers to any native TNC A2 from any vertebrate source, including mammals such as primates (e.g. humans) and rodents (e.g., mice and rats), unless otherwise indicated. The term encompasses "full-length," unprocessed TNC A2 as well as any form of TNC A2 that results from processing in the cell. The term also encompasses naturally occurring variants of TNC A2, e.g., splice variants or allelic variants. The amino acid sequence of an exemplary human TNC A2 (with a C-terminal avi-tag and 6× His-tag) is shown in SEQ ID NO: 97. In the human tenascin-C molecule, the A2 domain is the second (counted from the N-terminus) of the up to nine alternatively spliced fibronectin-type III domains, which may be inserted between the fifth and the sixth of the constant fibronectin-type III domains (for a schematic representation of the domain structure of tenascin-C, see e.g. Orend and Chiquet-Ehrismann, Cancer Letters 244, 143-163 (2006). Similarly, in the mouse tenascin-C molecule, the A2 is the second of up to six alternatively spliced fibronectin-type III domains (described e.g. in Joestner and Faissner, J Biol Chem 274, 17144-17151 (1999)).

As used herein, "treatment" (and grammatical variations thereof such as "treat" or "treating") refers to clinical intervention in an attempt to alter the natural course of disease of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, $6^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." As used herein, the term "polypeptide having GnTIII activity" refers to polypeptides that are able to catalyze the addition of a N-acetylglucosamine (GlcNAc) residue in β-1-4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependence in a given activity as compared to the GnTIII (i.e., the candidate polypeptide will exhibit greater activity or not more than about 25-fold less and, preferably, not more than about tenfold less activity, and most preferably, not more than about three-fold less activity relative to the GnTIII).

As used herein, the term "Golgi localization domain" refers to the amino acid sequence of a Golgi resident polypeptide which is responsible for anchoring the polypeptide to a location within the Golgi complex. Generally, localization domains comprise amino terminal "tails" of an enzyme.

As used herein, the terms "engineer, engineered, engineering," particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

As used herein, the term "Fc-mediated cellular cytotoxicity" includes antibody-dependent cell-mediated cytotoxicity (ADCC) and cellular cytotoxicity mediated by a soluble Fc-fusion protein containing a human Fc-region. It is an immune mechanism leading to the lysis of "targeted cells" by "human immune effector cells."

As used herein, the term "human immune effector cells" refers to a population of leukocytes that display Fc receptors on their surfaces, through which they bind to the Fc-region of antibodies or of Fc-fusion proteins and perform effector functions. Such a population may include, but is not limited to, peripheral blood mononuclear cells (PBMC) and/or natural killer (NK) cells. As used herein, the term "targeted cells" refers to cells to which antigen binding molecules comprising an Fc region (e.g., antibodies or fragments thereof comprising an Fc region) or Fc-fusion proteins specifically bind. The antigen binding molecules or Fc fusion-proteins bind to target cells via the protein part that is N-terminal to the Fc region.

As used herein, the term "increased Fc-mediated cellular cytotoxicity" is defined as either an increase in the number of "targeted cells" that are lysed in a given time, at a given concentration of antibody or of Fc-fusion protein in the medium surrounding the target cells, by the mechanism of Fc-mediated cellular cytotoxicity defined above, and/or a reduction in the concentration of antibody or of Fc-fusion protein, in the medium surrounding the target cells, required to achieve the lysis of a given number of "targeted cells," in a given time, by the mechanism of Fc-mediated cellular cytotoxicity. The increase in Fc-mediated cellular cytotoxicity is relative to the cellular cytotoxicity mediated by the same antigen binding molecule or Fc-fusion protein produced by the same type of host cells, using the same standard production, purification, formulation and storage methods, (which are known to those skilled in the art) but that has not been produced by host cells engineered to have an altered pattern of glycosylation (e.g., to express the glycosyltransferase, GnTIII, or other glycosyltransferases) by the methods described herein.

By "antibody having increased antibody dependent cell-mediated cytotoxicity (ADCC)" is meant an antibody, as that term is defined herein, having increased ADCC as determined by any suitable method known to those of ordinary skill in the art. One accepted in vitro ADCC assay is as follows:

1) the assay uses target cells that are known to express the target antigen recognized by the antigen-binding region of the antibody;

2) the assay uses human peripheral blood mononuclear cells (PBMCs), isolated from blood of a randomly chosen healthy donor, as effector cells;

3) the assay is carried out according to following protocol:

i) the PBMCs are isolated using standard density centrifugation procedures and are suspended at $5 \times 10^6$ cells/ml in RPMI cell culture medium;

ii) the target cells are grown by standard tissue culture methods, harvested from the exponential growth phase with a viability higher than 90%, washed in RPMI cell culture medium, labeled with 100 micro-Curies of $^{51}$Cr, washed twice with cell culture medium, and resuspended in cell culture medium at a density of $10^5$ cells/ml;

iii) 100 microliters of the final target cell suspension above are transferred to each well of a 96-well microtiter plate;

iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;

v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);

vi) for the spontaneous release (SR) controls, 3 additional wells in the plate containing the labeled target cells, receive 50 microliters of RPMI cell culture medium instead of the antibody solution (point iv above);

vii) the 96-well microtiter plate is then centrifuged at 50×g for 1 minute and incubated for 1 hour at 4° C.;

viii) 50 microliters of the PBMC suspension (point i above) are added to each well to yield an effector:target cell ratio of 25:1 and the plates are placed in an incubator under 5% $CO_2$ atmosphere at 37° C. for 4 hours;

ix) the cell-free supernatant from each well is harvested and the experimentally released radioactivity (ER) is quantified using a gamma counter; x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);

4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress GnTIII.

II. Compositions and Methods

Tenascin-C, in particular the A2 domain and other alternatively spliced domains of tenascin-C, is specifically expressed in certain pathological conditions but essentially absent from healthy adult tissues, thus antibodies targeting this antigen have great therapeutic potential. The present invention provides antibodies that bind to the A2 domain of tenascin-C, in particular antibodies with high affinity and strong effector functions. Antibodies of the invention are useful, e.g., for the diagnosis or treatment of diseases characterized by expression of TNC A2, such as cancer.

A. Exemplary Anti-TNC A2 Antibodies

The present invention provides for antibodies that specifically bind to the A2 domain of tenascin C (TNC A2). Particularly, the present invention provides for antibodies that specifically bind TNC A2, wherein said antibodies are glycoengineered to have increased effector function. In one embodiment, an anti-TNC A2 antibody of the invention comprises at least one (e.g. one, two, three, four, five, or six) heavy or light chain complementarity determining region (CDR) selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, and SEQ ID NO: 47, or a variant or truncated form thereof containing at least the specificity-determining residues (SDRs) for said CDR. In one embodiment, an anti-TNC A2 antibody of the invention comprises at least one (e.g. one, two, three, four, five, or six) heavy or light chain complementarity determining region (CDR) selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, and SEQ ID NO: 47, wherein the antibody does not comprise the combination of a heavy chain CDR1 (HCDR1) selected from the group of SEQ ID NO: 3, SEQ ID NO: 5, SEQ ID NO: 7, a heavy chain CDR2 (HCDR2) selected from the group of SEQ ID NO: 9, SEQ ID NO: 15, and SEQ ID NO: 21, the heavy chain CDR3 (HCDR3) of SEQ ID NO: 27, the light chain CDR1 (LCDR1) of SEQ ID NO: 29, the light chain CDR2 (LCDR2) of SEQ ID NO: 35, and the light chain CDR3 (LCDR3) of SEQ ID NO:47.

In one embodiment, said at least one CDR is a heavy chain CDR, particularly a heavy chain CDR3 of SEQ ID NO: 27. In another embodiment, the antibody comprises at least one heavy chain CDR and at least one light chain CDR, particularly a heavy chain CDR3 of SEQ ID NO:27 and a light chain CDR3 of SEQ ID NO: 47.

In one embodiment, an antibody of the invention comprises at least one, at least two, or all three heavy chain CDR (HCDR) sequences selected from (a) HCDR1 comprising an amino acid sequence selected from the group of SEQ ID NO: 3, SEQ ID NO: 5, and SEQ ID NO: 7; (b) HCDR2 comprising an amino acid sequence selected from the group of SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, and SEQ ID NO: 25; and (c) HCDR3 comprising the amino acid sequence of SEQ ID NO: 27. In a further embodiment, the antibody comprises a heavy chain variable region comprising (a) a heavy chain CDR1 selected from the group of SEQ ID NO: 3, SEQ ID NO: 5, and SEQ ID NO: 7; (b) a heavy chain CDR2 selected from the group of SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, and SEQ ID NO: 25; and (c) the heavy chain CDR3 of SEQ ID NO: 27, or variants or truncated forms thereof containing at least the SDRs for said CDRs.

In one embodiment, an antibody of the invention comprises at least one, at least two, or all three light chain CDR (LCDR) sequences selected from (a) LCDR1 comprising an amino acid sequence selected from the group of SEQ ID NO: 29, SEQ ID NO: 31, and SEQ ID NO: 33; (b) LCDR2 comprising an amino acid sequence selected from the group of SEQ ID NO: 35, SEQ ID NO: 37, SEQ ID NO: 39, SEQ ID NO: 41, SEQ ID NO: 43, and SEQ ID NO: 45; and (c) LCDR3 comprising the amino acid sequence of SEQ ID NO: 47. In a further embodiment, the antibody comprises a light chain variable region comprising (a) a light chain CDR1 selected from the group of SEQ ID NO: 29, SEQ ID NO: 31, and SEQ ID NO: 33; (b) a light chain CDR2 selected from the group of SEQ ID NO: 35, SEQ ID NO: 37, SEQ ID NO: 39, SEQ ID NO: 41, SEQ ID NO: 43, and SEQ ID NO: 45; and (c) the light chain CDR3 of SEQ ID NO:47, or variants or truncated forms thereof containing at least the SDRs for said CDRs.

In one embodiment, an antibody of the invention comprises a heavy chain variable region comprising a heavy chain CDR1 selected from the group of SEQ ID NO: 3, SEQ ID NO: 5, and SEQ ID NO: 7; a heavy chain CDR2 selected from the group of SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, and SEQ ID NO: 25; and the heavy chain CDR3 of SEQ ID NO: 27, and a light chain variable region comprising a light chain CDR1 selected from the group of SEQ ID NO: 29, SEQ ID NO: 31, and SEQ ID NO: 33; a light chain CDR2 selected from the group of SEQ ID NO: 35, SEQ ID NO: 37, SEQ ID NO: 39, SEQ ID NO: 41, SEQ ID NO: 43, and SEQ ID NO: 45; and the light chain CDR3 of SEQ ID NO:47, or variants or truncated forms thereof containing at least the SDRs for said CDRs.

In another embodiment, an antibody of the invention comprises a heavy chain variable region comprising a heavy chain CDR1 selected from the group of SEQ ID NO: 3, SEQ ID NO: 5, and SEQ ID NO: 7; a heavy chain CDR2 selected from the group of SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, and SEQ ID NO: 25; and the heavy chain CDR3 of SEQ ID NO: 27, and a light chain variable region comprising a light chain CDR1 selected from the group of SEQ ID NO: 29, SEQ ID NO: 31, and SEQ ID NO: 33; a light chain CDR2 selected from the group of SEQ ID NO: 35, SEQ ID NO: 37, SEQ ID NO: 39, SEQ ID NO: 41, SEQ ID NO: 43, and SEQ ID NO: 45; and the light chain CDR3 of SEQ ID NO:47, wherein said antibody does not comprise the combination of a heavy chain CDR1 (HCDR1) selected from the group of SEQ ID NO: 3, SEQ ID NO: 5, SEQ ID NO: 7, a heavy chain CDR2 (HCDR2) selected from the group of SEQ ID NO: 9, SEQ ID NO: 15, and SEQ ID NO: 21, the heavy chain CDR3 (HCDR3) of SEQ ID NO: 27, the light chain CDR1 (LCDR1) of SEQ ID NO: 29, the light chain CDR2 (LCDR2) of SEQ ID NO: 35, and the light chain CDR3 (LCDR3) of SEQ ID NO:47.

In a specific embodiment, an antibody of the invention comprises a heavy chain variable region comprising a heavy chain CDR1 selected from the group of SEQ ID NO: 3, SEQ ID NO: 5, and SEQ ID NO: 7; a heavy chain CDR2 selected from the group of SEQ ID NO: 11, SEQ ID NO: 13, SEQ ID NO: 17, SEQ ID NO: 19, SEQ ID NO: 23, and SEQ ID NO: 25; and the heavy chain CDR3 of SEQ ID NO: 27, and a light chain variable region comprising the light chain CDR1 of SEQ ID NO: 29, the light chain CDR2 of SEQ ID NO: 35, and the light chain CDR3 of SEQ ID NO:47. In another specific embodiment, an antibody of the invention comprises a heavy chain variable region comprising a heavy chain CDR1 selected from the group of SEQ ID NO: 3, SEQ ID NO: 5, and SEQ ID NO: 7; a heavy chain CDR2 selected from the group of SEQ ID NO: 9, SEQ ID NO: 15, and SEQ ID NO: 21; and the heavy chain CDR3 of SEQ ID NO: 27, and a light chain variable region comprising a light chain CDR1 selected from the group of SEQ ID NO: 29, SEQ ID NO: 31, and SEQ ID NO: 33; a light chain CDR2 selected from the group of SEQ ID NO: 37, SEQ ID NO: 39, SEQ ID NO: 41, SEQ ID NO: 43, and SEQ ID NO: 45; and the light chain CDR3 of SEQ ID NO:47. In yet another specific embodiment, an antibody of the invention comprises a heavy chain variable region comprising a heavy chain CDR1 selected from the group of SEQ ID NO: 3, SEQ ID NO: 5, and SEQ ID NO: 7; a heavy chain CDR2 selected from the group of SEQ ID NO: 9, SEQ ID NO: 15, and SEQ ID NO: 21; and the heavy chain CDR3 of SEQ ID NO: 27, and a light chain variable region comprising the light chain of SEQ ID NO: 29, the light chain CDR2 of SEQ ID NO: 35; and the light chain CDR3 of SEQ ID NO:47.

In one embodiment, an antibody of the invention comprises a heavy chain variable region (VH) comprising an amino acid sequence having at least about 90%, 91%, 92%, 93%, 94%, 95%, 96%, 97%, 98% or 99% identity to a sequence selected from the group of SEQ ID NO: 59, SEQ ID NO: 67, and SEQ ID NO: 63. In one embodiment, the antibody comprises a heavy chain variable region comprising an amino acid sequence selected from the group of: SEQ ID NO: 59, SEQ ID NO: 67, and SEQ ID NO: 63.

In certain embodiments, a VH sequence having at least 90%, 91%, 92%, 93%, 94%, 95%, 96%, 97%, 98% or 99% identity contains substitutions (e.g., conservative substitutions), insertions, or deletions relative to the reference sequence, but an anti-TNC A2 antibody comprising that sequence retains the ability to bind to TNC A2. In certain embodiments, a total of 1 to 10 amino acids have been substituted, inserted and/or deleted in SEQ ID NO 59, 63 or 67. In certain embodiments, substitutions, insertions, or deletions occur in regions outside the HVRs or CDRs (i.e., in the FRs). Optionally, an anti-TNC A2 antibody according to the invention comprises the VH sequence in SEQ ID NO 59, 63 or 67, including post-translational modifications of that sequence. In a particular embodiment, the VH comprises one, two or three heavy chain CDRs selected from the sequences set forth in SEQ ID NOs 3, 5, 7, 9, 11, 13, 15, 17, 19, 21, 23, 25 and 27 for the HCDR1, HCDR2 and HCDR3.

In another embodiment, an antibody of the invention comprises a light chain variable region comprising an amino acid sequence having at least about 90%, 91%, 92%, 93%, 94%, 95%, 96%, 97%, 98% or 99% identity to a sequence selected from the group of SEQ ID NO: 55, SEQ ID NO: 57, SEQ ID NO: 69, SEQ ID NO: 73, SEQ ID NO: 77, SEQ ID NO: 81, SEQ ID NO: 85, and SEQ ID NO: 89. In yet another embodiment, the antibody comprises a light chain variable region comprising an amino acid sequence selected from the group of: SEQ ID NO: 55, SEQ ID NO: 57, SEQ ID NO: 69, SEQ ID NO: 73, SEQ ID NO: 77, SEQ ID NO: 81, SEQ ID NO: 85, and SEQ ID NO: 89.

In certain embodiments, a VL sequence having at least 90%, 91%, 92%, 93%, 94%, 95%, 96%, 97%, 98% or 99% identity contains substitutions (e.g., conservative substitutions), insertions, or deletions relative to the reference sequence, but an anti-TNC A2 antibody comprising that sequence retains the ability to bind to TNC A2. In certain embodiments, a total of 1 to 10 amino acids have been substituted, inserted and/or deleted in SEQ ID NO 55, 57, 69, 73, 77, 81, 85 or 89. In certain embodiments, the substitutions, insertions, or deletions occur in regions outside the HVRs or CDRs (i.e., in the FRs). Optionally, an anti-TNC A2 antibody of the invention comprises the VL sequence in SEQ ID NO 55, 57, 69, 73, 77, 81, 85 or 89, including post-translational modifications of that sequence. In a particular embodiment, the VL comprises one, two or three light chain CDRs selected from sequences set forth in SEQ ID NOs 29, 31, 33, 35, 37, 39, 41, 43, 45 and 47 for the LCDR1, LCDR2 and LCDR3.

In another aspect, an anti-TNC A2 antibody is provided, wherein the antibody comprises a VH as in any of the embodiments provided above, and a VL as in any of the embodiments provided above. In one embodiment, the antibody comprises a heavy chain variable region comprising an amino acid sequence that is at least about 90%, 91%, 92%, 93%, 94%, 95%, 96%, 97%, 98%, 99% or 100% identical to a sequence selected from the group of: SEQ ID NO: 59, SEQ ID NO: 67, and SEQ ID NO: 63, and a light chain variable region comprising an amino acid sequence that is at least about 90%, 91%, 92%, 93%, 94%, 95%, 96%, 97%, 98%, 99% or 100% identical to a sequence selected from the group of: SEQ ID NO: 55, SEQ ID NO: 57, SEQ ID NO: 69, SEQ ID NO: 73, SEQ ID NO: 77, SEQ ID NO: 81, SEQ ID NO: 85, and SEQ ID NO: 89. In one embodiment, the antibody comprises the VH and VL sequences in SEQ ID NO 59, 63 or 67 and SEQ ID NO 55, 57, 69, 73, 77, 81, 85 or 89, respectively, including post-translational modifications of those sequences.

In one embodiment, the antibody comprises a heavy chain variable region comprising an amino acid sequence selected from the group of: SEQ ID NO: 59, SEQ ID NO: 67, and SEQ ID NO: 63, and a light chain variable region comprising an amino acid sequence selected from the group of: SEQ ID NO: 55, SEQ ID NO: 57, SEQ ID NO: 69, SEQ ID NO: 73, SEQ ID NO: 77, SEQ ID NO: 81, SEQ ID NO: 85, and SEQ ID NO: 89, wherein said antibody does not comprise a combination of a heavy chain variable region comprising the amino acid sequence of SEQ ID NO: 59 and a light chain variable region comprising the amino acid sequence of SEQ ID NO: 55 or SEQ ID NO: 57.

In a specific embodiment, an antibody of the invention comprises a heavy chain variable region comprising the amino acid sequence of SEQ ID NO: 59 and a light chain variable region comprising an amino acid sequence selected from the group of SEQ ID NO: 69, SEQ ID NO: 73, SEQ ID NO: 77, SEQ ID NO: 81, SEQ ID NO: 85, and SEQ ID NO: 89. In another specific embodiment, an antibody of the invention comprises a heavy chain variable region comprising the amino acid sequence of SEQ ID NO:63 or SEQ ID NO:67, and a light chain variable region comprising the amino acid sequence of SEQ ID NO: 57. In yet another specific embodiment an antibody of the invention comprises a heavy chain variable region comprising the amino acid sequence of SEQ ID NO:59, and a light chain variable region comprising the amino acid sequence of SEQ ID NO: 55 or SEQ ID NO:57. In a particular embodiment, the antibody according to any of the above embodiments additionally comprises an Fc region or a region equivalent to the Fc region of an immunoglobulin.

In one embodiment an antibody of the invention comprises an Fc region, particularly a IgG Fc region, most particularly a IgG1 Fc region.

In a particular embodiment, the antibody of the invention is a full length antibody, particularly an IgG class antibody, most particularly an IgG1 isotype antibody. In another embodiment, the antibody of the invention is an antibody fragment, selected from the group of: an scFv fragment, an Fv fragment, a Fab fragment, and a F(ab')2 fragment. In a further embodiment, the antibody of the invention is an antibody fragment having an Fc region, or a fusion protein that comprises a region equivalent to the Fc region of an immunoglobulin. In one embodiment, the antibody of the invention is a monoclonal antibody.

In one embodiment, an antibody of the invention is chimeric, more specifically humanized. In a particular embodiment, an antibody of the invention is human. In another embodiment, an antibody of the invention comprises a human constant region. In one embodiment the antibody of the invention comprises a human Fc region, preferably a human IgG Fc region, most particularly a human IgG1 Fc region.

In one embodiment, an antibody of the invention comprises a heavy chain constant region, wherein said heavy chain constant region is a human IgG constant region, particularly a human IgG1 constant region, comprising an Fc region. In a specific embodiment, the antibody comprises a heavy chain constant region comprising the amino acid sequence of SEQ ID NO: 93. In another specific embodiment an antibody of the invention comprises a light chain constant region comprising the amino acid sequence of SEQ ID NO: 95. In yet another specific embodiment, an antibody of the invention comprises a heavy chain constant region comprising the amino acid sequence of SEQ ID NO: 93, and a light chain constant region comprising the amino acid sequence of SEQ ID NO: 95.

In a particular embodiment, the invention provides an antibody that specifically binds to TNC A2, wherein said antibody comprises a) a heavy chain variable region comprising an amino acid sequence that is at least about 90%, 91%, 92%, 93%, 94%, 95%, 96%, 97%, 98%, 99% or 100% identical to a sequence selected from the group of SEQ ID NO: 59, SEQ ID NO: 67, and SEQ ID NO: 63, or a light chain variable region comprising an amino acid sequence that is at least about 90%, 91%, 92%, 93%, 94%, 95%, 96%, 97%, 98%, 99% or 100% identical to a sequence selected from the group of SEQ ID NO: 55, SEQ ID NO: 57, SEQ ID NO: 69, SEQ ID NO: 73, SEQ ID NO: 77, SEQ ID NO: 81, SEQ ID NO: 85, and SEQ ID NO: 89, or a combination thereof, and b) an Fc region or a region equivalent to the Fc region of an immunoglobulin.

In one embodiment, an antibody of the invention comprises an Fc region, wherein said Fc region is a glycoengineered Fc region. In a further embodiment, an antibody of the invention is glycoengineered to have modified oligosaccharides in the Fc region. In a specific embodiment, the antibody has an increased proportion of bisected oligosaccharides in the Fc region, compared to a non-glycoengineered antibody. In a more specific embodiment, at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 50%, more preferably at least about 70%, of the N-linked oligosaccharides in the Fc region of the antibody are bisected. The bisected oligosaccharides may be of the hybrid or complex type.

In another specific embodiment, an antibody of the invention has an increased proportion of non-fucosylated oligosaccharides in the Fc region, compared to a non-glycoengineered antibody. In a more specific embodiment, at least about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 50%, more preferably at least about 70%, of the N-linked oligosaccharides in the Fc region of the antibody are non-fucosylated. The non-fucosylated oligosaccharides may be of the hybrid or complex type.

In a particular embodiment, an antibody of the invention has an increased proportion of bisected, non-fucosylated oligosaccharides in the Fc region, compared to a non-glycoengineered antibody. Specifically, the antibody comprises an Fc region in which at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 15%, more preferably at least about 25%, at least about 35% or at least about 50%, of the N-linked oligosaccharides are bisected, non-fucosylated. The bisected, non-fucosylated oligosaccharides may be of the hybrid or complex type.

In one embodiment, an antibody of the invention has increased effector function and/or increased Fc receptor binding affinity. Increased effector function and/or increased Fc receptor binding can result e.g. from glycoengineering and/or affinity maturation of antibodies. In one embodiment, the increased effector function and/or increased Fc receptor binding is a result of glycoengineering of the Fc region of the antibody. In another embodiment, the increased effector function and/or increased Fc receptor binding is a result of a combination of increased affinity and glycoengineering. The increased effector function can include, but is not limited to, one or more of the following: increased Fc-mediated cellular cytotoxicity (including increased antibody-dependent cell-mediated cytotoxicity (ADCC)), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. In a particular embodiment, the increased effector function is increased ADCC. The increased Fc receptor binding preferably is increased binding to an activating Fc receptor, most preferably FcγRIIIa.

In one embodiment, an antibody of the invention does not cause a clinically significant level of toxicity when administered to an individual in a therapeutically effective amount.

In one embodiment, an antibody of the invention is affinity matured. In a further embodiment, an antibody of the invention binds to the A2 domain of tenascin C (TNC A2) with a dissociation constant ($K_D$) value lower than about 1 μM to about 0.001 nM, particularly a $K_D$ value lower than about 100 nM, lower than about 20 nM, lower than about 10 nM, or lower than about 1 nM. In one embodiment, an antibody of the invention binds to the A2 domain of human, mouse, and cynomolgus TNC A2. In one embodiment, an antibody of the invention binds to the A2 domain of human and cynomolgus TNC A2. In a more specific embodiment, an antibody of the invention binds to the A2 domain of human and cynomolgus TNC A2 with a $K_D$ value lower than about lower than about 20 nM, lower than about 10 nM, or lower than about 1 nM. $K_D$ values are determined by Surface Plasmon Resonance, using the antibodies as Fab or IgG, particularly as IgG.

In one embodiment, an anti-TNC A2 antibody of the invention binds TNC A2 in human tissues. In a particular embodiment, the invention provides an antibody that specifically binds to the A2 domain of tenascin C (TNC A2), wherein said antibody comprises a heavy chain variable region comprising an amino acid sequence selected from the group of SEQ ID NO: 59, SEQ ID NO: 67, and SEQ ID NO: 63, a light chain variable region comprising an amino acid sequence selected from the group of SEQ ID NO: 55, SEQ ID NO: 57, SEQ ID NO: 69, SEQ ID NO: 73, SEQ ID NO: 77, SEQ ID NO: 81, SEQ ID NO: 85, and SEQ ID NO: 89, and a human IgG Fc region, and wherein optionally said antibody is glycoengineered to have increased effector function and/or Fc receptor binding affinity. In another particular embodiment, the invention provides an antibody that specifically binds to the A2 domain of tenascin C (TNC A2), wherein said antibody comprises a heavy chain variable region comprising an amino acid sequence selected from the group of SEQ ID NO: 59, SEQ ID NO: 67, and SEQ ID NO: 63, a light chain variable region comprising an amino acid sequence selected from the group of SEQ ID NO: 55, SEQ ID NO: 57, SEQ ID NO: 69, SEQ ID NO: 73, SEQ ID NO: 77, SEQ ID NO: 81, SEQ ID NO: 85, and SEQ ID NO: 89, and a human IgG Fc region, and wherein said antibody has an increased proportion of non-fucosylated oligosaccharides and/or an increased proportion of bisected oligosaccharides in said Fc region.

In one aspect, the invention provides for an antibody that specifically bind to the A2 domain of tenascin C (TNC A2), wherein said antibody is derived from a parent antibody comprising the heavy chain CDR1 of SEQ ID NO: 3, the heavy chain CDR2 of SEQ ID NO: 9, the heavy chain CDR3 of SEQ ID NO: 27, the light chain CDR1 of SEQ ID NO: 29, the light chain CDR2 of SEQ ID NO: 35, and the light chain CDR3 of SEQ ID NO: 47, and wherein said antibody comprises at least one amino acid substitution in at least one heavy or light chain CDR of to the parent antibody. For example, the antibody may comprise at least one, e.g. from about one to about ten (i.e., about 1, 2, 3, 4, 5, 6, 7, 8, 9, or 10), and particularly from about two to about five, substitutions in one or more hypervariable regions or CDRs (i.e., 1, 2, 3, 4, 5, or 6 hypervariable regions or CDRs) of the parent antibody. In certain embodiments, any one or more amino acids of the parent antibody as provided above are substituted at the following CDR positions:

Heavy chain CDR2 (SEQ ID NO: 9): positions 1, 6 and 8
Light chain CDR1 (SEQ ID NO: 29): positions 5 and 9
Light chain CDR1 (SEQ ID NO: 35): positions 1, 2 and 3
In certain embodiments, the substitutions are conservative substitutions, as provided herein. In certain embodiments, any one or more of the following substitutions may be made in any combination:

Heavy chain CDR2 (SEQ ID NO: 9): G1A or V, F6L, T8I
Light chain CDR1 (SEQ ID NO: 29): G5S, D9V
Light chain CDR1 (SEQ ID NO: 35): A1D, A2S or V, S3Y or T
Additionally, the antibody may also comprise one or more additions, deletions and/or substitutions in one or more framework regions of either the heavy or the light chain, compared to the parent antibody. In one embodiment, said at least one amino acid substitution in at least one CDR contributes to increased binding affinity of the antibody compared to its parent antibody. In another embodiment said antibody has at least about 2-fold to about 10-fold greater affinity for TNC A2 than the parent antibody (when comparing the antibody of the invention and the parent antibody in the same format, e.g. the Fab format). Further, the antibody derived from a parent antibody may incorporate any of the features, singly or in combination, described in the preceding paragraphs in relation to the antibodies of the invention.

The present invention also provides for polynucleotides encoding antibodies that specifically bind to the A2 domain of tenascin-C. In one aspect, the invention is directed to an isolated polynucleotide encoding a polypeptide that forms part of an anti-TNC A2 antibody according to the invention as described hereinbefore. In one embodiment, the isolated polynucleotide encodes an antibody heavy chain and/or an antibody light chain that forms part of an anti-TNC A2 antibody according to the invention as described hereinbefore.

In one embodiment, the invention is directed to an isolated polynucleotide comprising a sequence encoding one or more (e.g. one, two, three, four, five, or six) of the heavy or light chain complementarity determining regions (CDRs) set forth in SEQ ID NOs 3, 5, 7, 9, 11, 13, 15, 17, 19, 21, 23, 25, 27, 29, 31, 33, 35, 37, 39, 41, 43, 45 and 47, or a variant or truncated form thereof containing at least the specificity-determining residues (SDRs) for said CDR. In another embodiment, the polynucleotide comprises a sequence that encodes three heavy chain CDRs (e.g., HCDR1, HCDR2, and HCDR3) or three light chain CDRs (e.g. LCDR1, LCDR2, and LCDR3) selected from SEQ ID NOs 3, 5, 7, 9, 11, 13, 15, 17, 19, 21, 23, 25, 27, 29, 31, 33, 35, 37, 39, 41, 43, 45 and 47, or variants or truncated forms thereof containing at least the SDRs for each of said three complementarity determining regions. In yet another embodiment, the polynucleotide comprises a sequence encoding three heavy chain CDRs (e.g., HCDR1, HCDR2, and HCDR3) and three light chain CDRs (e.g. LCDR1, LCDR2, and LCDR3) selected from SEQ ID NOs 3, 5, 7, 9, 11, 13, 15, 17, 19, 21, 23, 25, 27, 29, 31, 33, 35, 37, 39, 41, 43, 45 and 47. In a particular embodiment the polynucleotide encoding one or more CDRs comprises a sequence that is at least about 90%, 95%, 96%, 97%, 98%, 99%, or 100% identical to one or more of the CDR nucleotide sequences of SEQ ID NOs 4, 6, 8, 10, 12, 14, 16, 18, 20, 22, 24, 26, 28, 30, 32, 34, 36, 38, 40, 42, 44, 46, 48, 49, 50, 51, 52, 53 and 54.

In a further embodiment, the polynucleotide comprises a sequence encoding a heavy chain variable region selected from the group of SEQ ID NO: 59, SEQ ID NO: 67, and SEQ ID NO: 63, and/or a sequence encoding a light chain variable region selected from the group of SEQ ID NO: 55, SEQ ID NO: 57, SEQ ID NO: 69, SEQ ID NO: 73, SEQ ID NO: 77, SEQ ID NO: 81, SEQ ID NO: 85, and SEQ ID NO: 89. In a particular embodiment, the polynucleotide encoding a heavy chain and/or light chain variable region comprises a sequence selected from the group of variable region nucleotide sequences consisting of SEQ ID NOs 56, 58, 60, 62, 64, 66, 68, 70, 72, 74, 76, 78, 80, 82, 84, 86, 88, 90 and 92, or a combination thereof.

In a specific embodiment, the polynucleotide comprises a sequence encoding a heavy chain variable region selected from the group of SEQ ID NO: 59, SEQ ID NO: 67, and SEQ ID NO: 63, and a sequence encoding a heavy chain constant region, particularly a human heavy chain constant region. In a particular embodiment, said heavy chain constant region is a human IgG heavy chain constant region, specifically a human IgG1 heavy chain constant region, comprising an Fc region. In a specific embodiment, said heavy chain constant region comprises the sequence of SEQ ID NO: 93. In another specific embodiment, the polynucleotide comprises a sequence encoding a light chain variable region selected from the group of SEQ ID NO: 55, SEQ ID NO: 57, SEQ ID NO: 69, SEQ ID NO: 73, SEQ ID NO: 77, SEQ ID NO: 81, SEQ ID NO: 85, and SEQ ID NO: 89, and a sequence encoding a light chain constant region, particularly a human light chain constant region. In a specific embodiment, said light chain constant region comprises the sequence of SEQ ID NO: 95.

In one embodiment, the invention is directed to a composition that comprises a first isolated polynucleotide encoding a polypeptide comprising an amino acid sequence that is at least about 90%, 95%, 96%, 97%, 98%, 99%, or 100% identical to a sequence selected from the group consisting of SEQ ID NO: 59, SEQ ID NO: 67, and SEQ ID NO: 63, and a second isolated polynucleotide encoding a polypeptide comprising an amino acid sequence that is at least about 90%, 95%, 96%, 97%, 98%, 99%, or 100% identical to a sequence selected from the group consisting of SEQ ID NO: 55, SEQ ID NO: 57, SEQ ID NO: 69, SEQ ID NO: 73, SEQ ID NO: 77, SEQ ID NO: 81, SEQ ID NO: 85, and SEQ ID NO: 89.

In one embodiment, the invention is directed to a composition that comprises a first isolated polynucleotide comprising a sequence that is at least about 90%, 95%, 96%, 97%, 98%, 99%, or 100% identical to a sequence selected from the group consisting of SEQ ID NO: 60, SEQ ID NO: 68, and SEQ ID NO: 64, and a second isolated polynucleotide comprising a sequence that is at least about 90%, 95%, 96%, 97%, 98%, 99%, or 100% identical to a sequence selected from the group consisting of SEQ ID NO: 56, SEQ ID NO: 58, SEQ ID NO: 70, SEQ ID NO: 74, SEQ ID NO: 78, SEQ ID NO: 82, SEQ ID NO: 86, and SEQ ID NO: 90.

In a further aspect, the invention is also directed to isolated polypeptides, encoded by any of the polynucleotides according the invention as described hereinbefore.

In a further aspect, an anti-TNC A2 antibody according to any of the above embodiments may incorporate any of the features, singly or in combination, as described in Sections 1-6 below:

1. Antibody Affinity

In certain embodiments, an antibody provided herein has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, $10^{-8}$ M to $10^{-13}$ M, e.g., from $10^{-9}$ M to $10^{-13}$ M). Preferably, the antibodies provided herein bind to the A2 domain of tenascin-C (TNC A2), in particular human TNC A2, with a $K_D$ value lower than 1 nM, as determined by Surface Plasmon Resonance (SPR).

According to one embodiment, $K_D$ is measured using surface plasmon resonance. Such an assay can be performed, for example, using a BIACORE®-T100 machine (GE Healthcare) at 25° C. with biotinylated antigen immobilized on streptavidin chips at ~80 response units (RU). Briefly, for immobilization antigen is diluted with 10 mM HEPES, 150 mM NaCl, 3 mM EDTA, 0.05% Surfactant P20, pH 7.4, to 0.1 μg/ml before injection at a flow rate of 10 μl/minute to achieve approximately 80 response units (RU) of coupled protein. Protein and DNA sequences of suitable antigen constructs are shown in SEQ ID NOs 99-104. For kinetics measurements, two-fold serial dilutions of Fab (1.56 nM to 100 nM) or IgG (0.39 nM to 25 nM) are injected in 10 mM HEPES, 150 mM NaCl, 3 mM EDTA, 0.05% Surfactant P20, pH 7.4 at 25° C. at a flow rate of approximately 50 μl/min. Association and dissociation times are 180 sec and a regeneration with 10 mM glycine pH 1.5 for 60 sec is performed between the cycles. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999).

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003), or Carter, *Nat. Rev. Immunol.* 6:343-357 (2006).

Single-chain Fv or scFv fragments comprise a VH domain and a VL domain as a single polypeptide chain. Typically, the VH and VL domains are joined by a linker sequence. For a review of scFv fragments, see, e.g., Plückthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90:6444-6448 (1993). Triabodies and tetrabodies are also described in Hudson et al., *Nat. Med.* 9:129-134 (2003).

A minibody is a bivalent, homodimeric scFv derivative that contains a constant region, typically the CH3 region of an immunoglobulin, preferably IgG, more preferably IgG1, as the dimerisation region. Generally, the constant region is connected to the scFv via a hinge region and/or a linker region. Examples of minibody proteins can be found in Hu et al., *Cancer Res.* 56: 3055-61 (1996).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof. In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity. Humanization may be achieved by various methods including, but not limited to (a) grafting the entire non-human variable domains onto human constant regions to generate chimeric antibodies, (b) grafting only the non-human (e.g., donor antibody) CDRs onto human (e.g., recipient antibody) framework and constant regions with or without retention of critical framework residues (e.g., those that are important for retaining good antigen binding affinity or antibody functions), (c) grafting only the non-human specificity-determining regions (SDRs or a-CDRs; the residues critical for the antibody-antigen interaction) onto human framework and constant regions, or (d) transplanting the entire non-human variable domains, but "cloaking" them with a human-like section by replacement of surface residues. Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527, 791, 6,982,321, and 7,087,409; Jones et al., *Nature* 321:522-525 (1986); Morrison et al., *Proc. Natl. Acad. Sci.* 81:6851-6855 (1984); Morrison and Oi, *Adv. Immunol.* 44:65-92 (1988); Verhoeyen et al., *Science* 239:1534-1536 (1988); Padlan, *Molec. Immun.* 31(3):169-217 (1994); Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas.

Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for TNC A2 and the other is for any other antigen. In certain embodiments, bispecific antibodies may bind to two different epitopes of TNC A2. Bispecific antibodies may also be used to localize cytotoxic agents to cells which express TNC A2. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305:537 (1983), WO 93/08829, and Traunecker et al., *EMBO J.* 10:3655 (1991)), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science* 229:81 (1985)); using leucine zippers to produce bi-specific antibodies (see, e.g., Kostelny et al., *J. Immunol.* 148(5):1547-1553 (1992)); using "diabody" technology for making bispecific antibody fragments (see, e.g., Hollinger et al., *Proc. Natl. Acad. Sci. USA* 90:6444-6448 (1993)); and using single-chain Fv (sFv) dimers (see, e.g. Gruber et al., *J. Immunol.* 152:5368 (1994)); and preparing trispecific antibodies as described, e.g., in Tutt et al. *J. Immunol.* 147:60 (1991). Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to TNC A2 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Amino acid substitutions can result in replacing one amino acid with another amino acid having similar structural and/or chemical properties, e.g., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, phenylalanine, tryptophan, and methionine; polar neutral amino acids include serine, threonine, cysteine, tyrosine, asparagine, and glutamine; positively charged (basic) amino acids include arginine, lysine, and histidine; and negatively charged (acidic) amino acids include aspartic acid and glutamic acid. Conservative substitutions are shown in Table 2 under the heading of "preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g., basic). The variation allowed may be experimentally determined by systematically making insertions, deletions, or substitutions of amino acids in a polypeptide molecule using recombinant DNA techniques and assaying the resulting recombinant variants for activity. One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, it may be beneficial to analyze a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In some embodiments, modifications of the oligosaccharide in an antibody of the invention may be made in order to create antibody variants with certain improved properties.

In one aspect, the present invention provides glycoforms of anti-TNC A2 antibodies having increased effector function, including antibody-dependent cellular cytotoxicity. Glycosylation engineering of antibodies has been previously described. See, e.g., U.S. Pat. No. 6,602,684, incorporated herein by reference in its entirety. Methods of producing anti-TNC A2 antibodies from host cells that have altered activity of genes involved in glycosylation are also described herein in detail (see, e.g, section entitled "Recombinant Methods and Compositions" below). An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. The oligosaccharides normally found in the Fc region of serum IgG are of complex biantennary type (Wormald et al., *Biochemistry* 36:130-38 (1997), with a low level of terminal sialic acid and bisecting N-acetylglucosamine (GlcNAc), and a variable degree of terminal galactosylation and core fucosylation (fucose attached to a GlcNAc residue in the "stem" of the biantennary oligosaccharide structure). Some studies suggest that the minimal carbohydrate structure required for FcγR binding lies within the oligosaccharide core. Lund et al., *J. Immunol.* 157:4963-69 (1996).

The mouse- or hamster-derived cell lines used in industry and academia for production of antibodies normally attach the required oligosaccharide determinants to Fc sites. IgGs expressed in these cell lines lack, however, the bisecting GlcNAc found in low amounts in serum IgGs. Lifely et al., *Glycobiology* 318:813-22 (1995). In the N-linked glycosylation pathway, a bisecting GlcNAc is added by GnTIII. Schachter, *Biochem. Cell Biol.* 64:163-81 (1986). Umaña et al. used a single, antibody-producing CHO cell line that was previously engineered to express, in an externally-regulated fashion, different levels of a cloned GnTIII enzyme gene (Umaña, P., et al., *Nature Biotechnol.* 17:176-180 (1999)). This approach established for the first time a rigorous correlation between expression of a glycosyltransferase (e.g., GnTIII) and the ADCC activity of the modified antibody. Thus, the invention contemplates anti-TNC A2 antibodies, comprising an Fc region or region equivalent to an Fc region having altered glycosylation resulting from changing the expression level of a glycosyltransferase gene in the antibody-producing host cell. In a specific embodiment, the change in gene expression level is an increase in GnTIII activity. Increased GnTIII activity results in an increase in the percentage of bisected oligosaccharides, as well as a decrease in the percentage of fucosylated oligosaccharides, in the Fc region of the antibody. This antibody, or fragment thereof, has increased Fc receptor binding affinity and increased effector function.

Antibodies are provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umaña et al.); and US 2005/0123546 (Umaña et al.).

In one embodiment, the anti-TNC A2 antibodies of the invention have an increased proportion of bisected oligosaccharides in the Fc region as a result of the modification of their oligosaccharides by the methods of the present invention. In one embodiment, the percentage of bisected N-linked oligosaccharides in the Fc region of the anti-TNC A2 antibodies of the invention is at least about 10% to about 100%, specifically at least about 50%, more specifically, at least about 60%, at least about 70%, at least about 80%, or at least about 90-95% of the total oligosaccharides. The bisected oligosaccharides may be of the hybrid or complex type.

In another embodiment, the anti-TNC A2 antibodies of the invention have an increased proportion of nonfucosylated oligosaccharides in the Fc region as a result of the modification of their oligosaccharides by the methods of the present invention. In one embodiment, the percentage of nonfucosylated oligosaccharides is at least about 20% to about 100%, specifically at least about 50%, at least about 60% to about 70%, and more specifically, at least about 75%. The nonfucosylated oligosaccharides may be of the hybrid or complex type.

The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described for example in WO 2008/077546. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. The relative amount of fucose is the percentage of fucose-containing structures related to all glycostructures identified in an N-Glycosidase F treated sample (e. g. complex, hybrid and high mannose structures) by MALDI-TOF MS. Such fucosylation variants may have improved ADCC function.

The glycoengineering methodology that can be used with the anti-TNC A2 antibodies of the present invention has been described in greater detail in U.S. Pat. No. 6,602,684, U.S. Pat. Appl. Publ. No. 2004/0241817 A1, U.S. Pat. Appl. Publ. No. 2003/0175884 A1, Provisional U.S. Patent Application No. 60/441,307 and WO 2004/065540, the entire contents of each of which is incorporated herein by reference in its entirety. The anti-TNC A2 antibodies of the present invention can alternatively be glycoengineered to have reduced fucose residues in the Fc region according to the techniques disclosed in U.S. Pat. Appl. Pub. No. 2003/0157108 (Genentech), or in EP 1 176 195 A1, WO 03/084570, WO 03/085119 and U.S. Pat. Appl. Pub. Nos. 2003/0115614, 2004/093621, 2004/110282, 2004/110704, 2004/132140, Niwa et al., J Immunol Methods 306, 151/160 (2006), U.S. Pat. No. 6,946,292 (Kyowa). Glycoengineered anti-TNC A2 antibodies of the invention may also be produced in expression systems that produce modified glycoproteins, such as those taught in U.S. Pat. Appl. Pub. No. 60/344,169 and WO 03/056914 (GlycoFi, Inc.) or in WO 2004/057002 and WO 2004/024927 (Greenovation).

Further examples of publications related to "defucosylated" or "fucose-deficient" antibody variants include: WO 2000/61739; WO 2001/29246; US 2002/0164328; US 2004/0109865; WO 2005/035586; WO 2005/035778; WO2005/053742; WO2002/031140; Okazaki et al. *J. Mol. Biol.* 336: 1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

In a particular embodiment, the anti-TNC A2 antibodies of the invention have an increased proportion of bisected, nonfucosylated oligosaccharides in the Fc region. The bisected, nonfucosylated oligosaccharides may be either hybrid or complex. Specifically, the methods of the present invention may be used to produce anti-TNC A2 antibodies in which at least about 10% to about 100%, specifically at least about 15%, more specifically at least about 20% to about 25%, and more specifically at least about 30% to about 35% of the oligosaccharides in the Fc region of the antigen binding molecule are bisected, nonfucosylated. The anti-TNC A2 antibodies of the present invention may also comprise an Fc region in which at least about 10% to about 100%, specifically at least about 15%, more specifically at least about 20% to about 25%, and more specifically at least about 30% to about 35% of the oligosaccharides in the Fc region of the antibody are bisected hybrid nonfucosylated.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Increases in ADCC or other effector functions of the anti-TNC A2 antibodies of the present invention can also achieved by increasing affinity of the antigen binding molecule for TNC A2, for example by affinity maturation or other methods of improving affinity (see Tang et al., *J. Immunol.* 2007, 179:2815-2823), or by amino acid modifications in the Fc region as described below. Combinations of these approaches are also encompassed by the present invention.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)). Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

For further examples concerning Fc region variants see also U.S. Pat. Appl. Nos. 60/439,498; 60/456,041; 60/514,549; or WO 2004/063351 (variant Fc regions with increased binding affinity due to amino acid modification); or U.S. patent application Ser. No. 10/672,280 or WO 2004/099249 (Fc variants with altered binding to FcγR due to amino acid modification), Duncan & Winter, *Nature* 322:738-40 (1988); U.S. Pat. No. 5,648,260; U.S. Pat. No. 5,624,821; and WO 94/29351.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an antibody conjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated polynucleotide encoding an anti-TNC A2 antibody described herein is provided. Such polynucleotide may encode an amino acid sequence comprising the VL and/or an amino acid sequence comprising the VH of the antibody (e.g., the light and/or heavy chains of the antibody). In a further embodiment, one or more vectors (e.g., cloning vectors or expression vectors) comprising such polynucleotide are provided. In a further embodiment, a host cell comprising such polynucleotide or such vector is provided. In one such embodiment, a host cell comprises (e.g., has been transformed with): (1) a vector comprising a polynucleotide that encodes an amino acid sequence comprising the VL of the antibody and an amino acid sequence comprising the VH of the antibody (e.g. a polycistronic vector), or (2) a first vector comprising a polynucleotide that encodes an amino acid sequence comprising the VL of the antibody and a second vector comprising a polynucleotide that encodes an amino acid sequence comprising the VH of the antibody. In one embodiment, the host cell is a eukaryotic cell, particularly a mammalian cell, e.g. a Chinese Hamster Ovary (CHO), a baby hamster kidney (BHK) cell or lymphoid cell (e.g., Y0, NS0, Sp20 cell). In one embodiment, a method of making an anti-TNC A2 antibody is provided, wherein the method comprises culturing a host cell comprising a polynucleotide encoding the antibody, as provided above, under conditions suitable for expression of the antibody, and optionally recovering the antibody from the host cell (or host cell culture medium).

For recombinant production of an anti-TNC A2 antibody, one or more polynucleotide(s) encoding an antibody, e.g., as described above, are isolated and inserted into one or more vectors for further cloning and/or expression in a host cell. Methods which are well known to those skilled in the art can be used to construct expression vectors containing the coding sequence of an anti-TNC A2 antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989) and Ausubel et al., CURRENT PROTOCOLS IN MOLECULAR BIOLOGY, Greene Publishing Associates and Wiley Interscience, N.Y (1989).

In one embodiment, one or several polynucleotides encoding an anti-TNC A2 antibody may be expressed under the control of a constitutive promoter or, alternatively, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different polynucleotides encoding an antibody of the present invention are comprised within the host cell system, some of them may be expressed under the control of a constitutive promoter, while others are expressed under the control of a regulated promoter.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006). Such expression systems are also taught in U.S. Pat. Appl. No. 60/344,169 and WO 03/056914 (methods for producing human-like glycoprotein in a non-human eukaryotic host cell).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383: 44-68 (1982); MRC 5 cells; and FS4 cells. Other useful mammalian host cell lines include Chinese hamster ovary (CHO) cells, including DHFR⁻ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Stable expression is generally preferred to transient expression because it typically achieves more reproducible results and also is more amenable to large-scale production; however, it is within the skill of one in the art to determine whether transient expression is better for a particular situation.

The present invention is further directed to a method for modifying the glycosylation profile of the anti-TNC A2 antibodies of the present invention that are produced by a host cell, comprising expressing in said host cell one or more polynucleotide(s) encoding an anti-TNC A2 antibody and one or more polynucleotide(s) encoding a polypeptide with a glycosyltransferase activity, or a vector comprising such polynucleotides. Generally, any type of cultured cell line, including the cell lines discussed above, can be used to generate cell lines for the production of anti-TNC A2 antibodies with altered glycosylation pattern. Preferred cell lines include CHO cells, BHK cells, NS0 cells, SP2/0 cells, YO myeloma cells, P3X63 mouse myeloma cells, PER cells, PER.C6 cells or hybridoma cells, and other mammalian cells. Polypeptides with glycosyltransferase activity include $\beta(1,4)$-N-acetylglucosaminyltransferase III (GnTIII), $\alpha$-mannosidase II (ManII), $\beta(1,4)$-galactosyltransferase (GalT), $\beta(1,2)$-N-acetylglucosaminyltransferase I (GnTI), and β(1,2)-N-acetylglucosaminyltransferase II (GnTII). In one embodiment, a combination of polynucleotides encoding for polynucleotides with glycosyltransferase activity are expressed in the host cell (e.g., GnTIII and Man II). Likewise, the method also encompasses expression of one or more polynucleotide(s) encoding the anti-TNC A2 antibody in a host cell in which a glycosyltransferase gene has been disrupted or otherwise deactivated (e.g., a host cell in which the activity of the gene encoding α1,6 core fucosyltransferase has been knocked out). In a particular embodiment, the anti-TNC A2 antibodies of the present invention can be produced in a host cell that further expresses a polynucleotide encoding a polypeptide having GnTIII activity to modify the glycosylation pattern of said antibodies. In a specific embodiment, the polypeptide having GnTIII activity is a fusion polypeptide comprising the Golgi localization domain of a Golgi resident polypeptide. In another particular embodiment, the expression of the anti-TNC A2 antibody of the present invention in a host cell that expresses a polynucleotide encoding a polypeptide having GnTIII activity results in anti-TNC A2 antibodies with increased Fc receptor binding affinity and/or increased effector function. Accordingly, in one embodiment, the present invention is directed to a host cell comprising (a) one or more isolated polynucleotide(s) comprising a sequence encoding a polypeptide having GnTIII activity; and (b) one or more isolated polynucleotide(s) encoding an anti-TNC A2 antibody of the present invention. In a particular embodiment, the polypeptide having GnTIII activity is a fusion polypeptide comprising the catalytic domain of GnTIII and the Golgi localization domain of a heterologous Golgi resident polypeptide. Particularly, said Golgi localization domain is the Golgi localization domain of mannosidase II. Methods for generating such fusion polypeptides and using them to produce antibodies with increased effector functions are disclosed in WO2004/065540, U.S. Provisional Pat. Appl. No. 60/495,142 and U.S. Pat. Appl. Publ. No. 2004/0241817, the entire contents of which are expressly incorporated herein by reference. In another embodiment, the host cell additionally comprises an isolated polynucleotide comprising a sequence encoding a polypeptide having mannosidase II (ManII) activity. The polynucleotide(s) encoding polypeptide(s), like the polynucleotide(s) encoding the anti-TNC A2 antibody, may be expressed under the control of a constitutive promoter or, alternately, a regulated expression system. Such systems are well known in the art, and include the systems discussed above.

The host cells which contain the coding sequence of the anti-TNC A2 antibody and/or the coding sequence of polypeptides having glycosyltransferase activity, and which express the biologically active gene products may be identified e.g. by DNA-DNA or DNA-RNA hybridization; the presence or absence of "marker" gene functions; assessing the level of transcription as measured by the expression of the respective mRNA transcripts in the host cell; or detection of the gene product as measured by immunoassay or by its biological activity—methods which are well known in the art. GnTIII or Man II activity can be detected e.g. by employing a lectin which binds to biosynthetis products of GnTIII or ManII, respectively. An example for such a lectin is the $E_4$-PHA lectin which binds preferentially to oligosaccharides containing bisecting GlcNAc. Biosynthesis products (i.e. specific oligosaccharide structures) of polypeptides having GnTIII or ManII activity can also be detected by mass spectrometric analysis of oligosaccharides released from glycoproteins produced by cells expressing said polypeptides. Alternatively, a functional assay which measures the increased Fc receptor binding or increased effector function mediated by antibodies produced by the cells engineered with the polynucleotide encoding a polypeptide having GnTIII activity may be used.

The present invention is also directed to a method for producing an anti-TNC A2 antibody having modified oligosaccharides, comprising (a) culturing a host cell engineered to express at least one polynucleotide encoding a polypeptide having glycosyltransferase activity under conditions which permit the production of an anti-TNC A2 antibody according to the present invention, wherein said polypeptide having glycosyltransferase activity is expressed in an amount sufficient to modify the oligosaccharides in the Fc region of said anti-TNC A2 antibody produced by said host cell; and (b) isolating said anti-TNC A2 antibody. In one embodiment, the polypeptide having glycosyltransferase activity is GnTIII. In another embodiment, there are two polypeptides having glycosyltransferase activity. In a particular embodiment, the two peptides having glycosyltransferase activity are GnTIII and ManII. In another embodiment, the polypeptide having glycosyltransferase activity is a fusion polypeptide comprising the catalytic domain of GnTIII. In a more specific embodiment, the fusion polypeptide further comprises the Golgi localization domain of a Golgi resident polypeptide. Particularly, the Golgi localization domain is the localization domain of mannosidase II or GnTI, most particularly the localization domain of mannosidase II. Alternatively, the Golgi localization domain is selected from the group consisting of: the localization domain of mannosidase I, the localization domain of GnTII, and the localization domain of α1,6 core fucosyltransferase.

In a particular embodiment, the modified anti-TNC A2 antibody produced by the host cell or method described above has an IgG constant region or a fragment thereof comprising the Fc region. In another particular embodiment the anti-TNC A2 antibody is a humanized or human antibody or a fragment thereof comprising an Fc region.

The anti-TNC A2 antibody with altered glycosylation produced by the host cell or method described above typically exhibit increased Fc receptor binding affinity and/or increased effector function as a result of the modification of the host cell (e.g., by expression of a glycosyltransferase gene). Preferably, the increased Fc receptor binding affinity is increased binding to an activating Fcγ receptor, most preferably the FcγRIIIa receptor. The increased effector function is preferably an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNCs), increased binding to monocytes, increased crosslinking of target-bound antibodies, increased direct signaling inducing apoptosis, increased dendritic cell maturation, and increased T cell priming.

C. Assays

Anti-TNC A2 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with another specific anti-TNC A2 antibody for binding to TNC A2. In certain embodiments, such a competing antibody binds to the same epitope (e.g., a linear or a conformational epitope) that is bound by said other specific anti-TNC A2 antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized TNC A2 is incubated in a solution comprising a first labeled antibody that binds to TNC A2 (e.g. the 2B10 antibody described in the Examples) and a second unlabeled antibody that is being tested for its ability to compete with the first antibody for binding to TNC A2. The second antibody may be present in a hybridoma supernatant. As a control, immobilized TNC A2 is incubated in a solution comprising the first labeled antibody but not the second unlabeled antibody. After incubation under conditions permissive for binding of the first antibody to TNC A2, excess unbound antibody is removed, and the amount of label associated with immobilized TNC A2 is measured. If the amount of label associated with immobilized TNC A2 is substantially reduced in the test sample relative to the control sample, then that indicates that the second antibody is competing with the first antibody for binding to TNC A2. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-TNC A2 antibodies thereof having biological activity. Biological activity may include, e.g., lysis of targeted cells, antibody-dependent cell-mediated cytotoxicity (ADCC), complement-dependent cytotoxicity (CDC), or induction of apoptosis. Antibodies having such biological activity in vivo and/or in vitro are also provided.

In certain embodiments, an antibody of the invention is tested for such biological activity. Exemplary assays for testing ADCC are described hereinbefore (see under "Definitions": "antibody having increased ADCC") and in Example 11. Assays for detecting cell lysis (e.g. by measurement of LDH release) or apoptosis (e.g. using the TUNEL assay) are well known in the art. Assays for measuring ADCC or CDC are also described in WO 2004/065540 (see Example 1 therein), the entire content of which is incorporated herein by reference.

D. Antibody Conjugates

The invention also provides conjugates comprising an anti-TNC A2 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, in an antibody-drug conjugate (ADC) an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an antibody conjugate comprises an antibody as described herein conjugated to an enzymatically active toxin or fragment thereof, including but not limited to diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

In another embodiment, an antibody conjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The antibody conjugates herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-TNC A2 antibodies provided herein is useful for detecting the presence of TNC A2 in a biological sample. The term "detecting" as used herein encompasses quantitative or qualitative detection. In certain embodiments, a biological sample comprises a cell or tissue, such as cells or tissues from brain, breast, colon, kidney, liver, lung, ovary, pancreas, prostate, skeletal muscle, skin, small intestine, stomach or uterus, including also cells or tissues tumors of these organs.

In one embodiment, an anti-TNC A2 antibody for use in a method of diagnosis or detection is provided. In a further aspect, a method of detecting the presence of TNC A2 in a biological sample is provided. In certain embodiments, the method comprises contacting the biological sample, optionally with a control sample, with an anti-TNC A2 antibody as described herein under conditions permissive for binding of the anti-TNC A2 antibody to TNC A2, and detecting whether a complex is formed between the anti-TNC A2 antibody and TNC A2. Such method may be an in vitro or in vivo method. In one embodiment, an anti-TNC A2 antibody is used to select subjects eligible for therapy with an anti-TNC A2 antibody, e.g. where TNC A2 is a biomarker for selection of patients.

Exemplary disorders that may be diagnosed using an antibody of the invention include disorders associated with the expression of TNC A2, such as cancer and inflammatory conditions.

In one aspect, a method of diagnosing disease in a subject is provided, said method comprising administering to said subject an effective amount of a diagnostic agent, wherein said diagnostic agent comprises an anti-TNC A2 antibody as described herein and a label, typically an imaging agent, that allows detection of a complex of said diagnostic agent and TNC A2.

In certain embodiments, labeled anti-TNC A2 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-TNC A2 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, acetate and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH2O, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, if the disease to be treated is cancer, it may be desirable to further provide one or more anti-cancer agents, e.g. a chemotherapeutic agent, an inhibitor of tumor cell proliferation, or an activator of tumor cell apoptosis. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application, but will typically be injectable or infusible solutions.

G. Therapeutic Methods and Compositions

Any of the anti-TNC A2 antibodies or pharmaceutical formulations comprising the anti-TNC A2 antibodies provided herein may be used in therapeutic methods.

The anti-TNC A2 antibodies provided herein can be used for treating diseases characterized by TNC A2 expression, particularly by abnormal expression (e.g. overexpression, or expression in a different pattern in the cell) of TNC A2 compared to normal tissue of the same cell type. TNC A2 is abnormally expressed (e.g. overexpressed) in many human tumors compared to non-tumor tissue of the same cell type. Thus, the anti-TNC A2 antibodies provided herein are particularly useful in the prevention of tumor formation, eradication of tumors and inhibition of tumor growth or metastasis. The anti-TNC A2 antibodies provided herein can be used to treat any tumor expressing TNC A2. Particular malignancies that can be treated by the anti-TNC A2 antibodies provided herein include, for example, lung cancer, colon cancer, gastric cancer, breast cancer, head and neck cancer, skin cancer, liver cancer, kidney cancer, prostate cancer, pancreatic cancer, brain cancer, cancer of the skeletal muscle.

The anti-TNC A2 antibodies disclosed herein can be used to inhibit tumor growth or kill tumor cells. For example, the anti-TNC A2 antibodies can bind to TNC A2 that is on the membrane or cell surface of cancerous cells (tumor cells or cells of the tumor stroma) and elicit, e.g., ADCC or other effector mediated killing of the cancerous cells.

The anti-TNC A2 antibodies can alternatively be used in order to block the function of TNC A2, particularly by physically interfering with its binding of another compound. For example, the antigen binding molecules can be used to block TNC A2 mediated cell adhesion, spreading or migration.

In one aspect, an anti-TNC A2 antibody for use as a medicament is provided. In further aspects, an anti-TNC A2 antibody for use in treating a disease characterized by expression of TNC A2 is provided. In certain embodiments, an anti-TNC A2 antibody for use in a method of treatment is provided. In certain embodiments, the invention provides an anti-TNC A2 antibody for use in a method of treating an individual having a disease characterized by expression of TNC A2, comprising administering to the individual an effective amount of the anti-TNC A2 antibody. In one such embodiment, the method further comprises administering to the individual an effective amount of at least one additional therapeutic agent, e.g., as described below. In further embodiments, the invention provides an anti-TNC A2 antibody for use in inducing lysis of a cell. In certain embodiments, the invention provides an anti-TNC A2 antibody for use in a method of inducing lysis of a cell in an individual comprising administering to the individual an effective amount of the anti TNC A2 antibody to induce lysis of a cell. An "individual" according to any of the above embodiments is preferably a human. A "disease characterized by expression of TNC A2" according to any of the above embodiments is preferably cancer, most preferably a cancer selected from the group of lung cancer, colon cancer, gastric cancer, breast cancer, head and neck cancer, skin cancer, liver cancer, kidney cancer, prostate cancer, pancreatic cancer, brain cancer, cancer of the skeletal muscle. A "cell" according to any of the above embodiments is preferably a cell present in a tumor, such as a tumor cell or a cell of the tumor stroma, most preferably a tumor cell. "TNC A2 expression" according to any of the above embodiments preferably is abnormal expression, such as overexpression or expression in a different pattern in the cell, compared to normal tissue of the same cell type.

In a further aspect, the invention provides for the use of an anti-TNC A2 antibody in the manufacture or preparation of a medicament. In one embodiment, the medicament is for treatment of a disease characterized by expression of TNC A2. In a further embodiment, the medicament is for use in a method of treating a disease characterized by expression of TNC A2 comprising administering to an individual having a disease characterized by expression of TNC A2 an effective amount of the medicament. In one such embodiment, the method further comprises administering to the individual an effective amount of at least one additional therapeutic agent, e.g., as described below. In a further embodiment, the medicament is for inducing lysis of a cell. In a further embodiment, the medicament is for use in a method of inducing lysis of a cell in an individual comprising administering to the individual an amount effective of the medicament to inducing lysis of a cell. An "individual" according to any of the above embodiments is preferably a human. A "disease characterized by expression of TNC A2" according to any of the above embodiments is preferably cancer, most preferably a cancer selected from the group of lung cancer, colon cancer, gastric cancer, breast cancer, skin cancer, liver cancer, kidney cancer, prostate cancer, pancreatic cancer, brain cancer, cancer of the skeletal muscle. A "cell" according to any of the above embodiments is preferably a cell present in a tumor, such as a tumor cell or a cell of the tumor stroma, most preferably a tumor cell. "TNC A2 expression" according to any of the above embodiments preferably is abnormal expression, such as overexpression or expression in a different pattern in the cell, compared to normal tissue of the same cell type.

In a further aspect, the invention provides a method for treating a disease characterized by expression of TNC A2. In one embodiment, the method comprises administering to an individual having such disease characterized by expression of TNC A2 an effective amount of an anti-TNC A2 antibody. In one such embodiment, the method further comprises administering to the individual an effective amount of at least one additional therapeutic agent, as described below. In a further embodiment, the invention provides a method for inducing lysis of a cell in an individual. In one embodiment, the method comprises administering to the individual an effective amount of an anti-TNC A2 antibody to induce lysis of a cell. An "individual" according to any of the above embodiments may be a human. A "disease characterized by expression of TNC A2" according to any of the above embodiments is preferably cancer, most preferably a cancer selected from the group of lung cancer, colon cancer, gastric cancer, breast cancer, skin cancer, liver cancer, kidney cancer, prostate cancer, pancreatic cancer, brain cancer, cancer of the skeletal muscle. A "cell" according to any of the above embodiments is preferably a cell present in a tumor, such as a tumor cell or a cell of the tumor stroma, most preferably a tumor cell. "TNC A2 expression" according to any of the above embodiments preferably is abnormal expression, such as overexpression or expression in a different pattern in the cell, compared to normal tissue of the same cell type.

In a further aspect, the invention provides pharmaceutical formulations comprising any of the anti-TNC A2 antibodies provided herein, e.g., for use in any of the above therapeutic methods. In one embodiment, a pharmaceutical formulation comprises any of the anti-TNC A2 antibodies provided herein and one or more pharmaceutically acceptable carrier. In another embodiment, a pharmaceutical formulation comprises any of the anti-TNC A2 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is an anti-cancer agent. Suitable anti-cancer agents are e.g. a chemotherapeutic agent, an inhibitor of tumor cell proliferation, or an activator of tumor cell apoptosis.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy. An antibody of the invention (and any additional therapeutic agent) can be administered by any suitable means, including parenteral, intrapulmonary, and intranasal, and, if desired for local treatment, intralesional administration. Parenteral administration includes intramuscular, intravenous, intraarterial, intraperitoneal, or subcutaneous administration. Intravenous administration is typically preferred. However, the intraperitoneal route is expected to be particularly useful, for example, in the treatment of colorectal tumors. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an antibody conjugate of the invention in place of or in addition to an anti-TNC A2 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an antibody conjugate of the invention in place of or in addition to an anti-TNC A2 antibody.

III. Examples

The following are examples of methods and compositions of the invention. It is understood that various other embodiments may be practiced, given the general description provided above.

Example 1

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions. DNA sequences were determined by double strand sequencing. In some cases desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of the subcloned gene fragments was confirmed by DNA sequencing. Gene Segments were designed with suitable restriction sites to allow sub-cloning into the respective expression vectors.

General information regarding the nucleotide sequences of human immunoglobulin light and heavy chains is given in: Kabat, E. A. et al., (1991) Sequences of Proteins of Immunological Interest, Fifth Ed., NIH Publication No 91-3242. For expression, all constructs contained a 5'-end DNA sequence coding for a leader peptide which targets proteins for secretion in eukaryotic cells. Exemplary leader peptides and polynucleotide sequences encoding them are given in SEQ ID NOs 107 to 115.

Preparation of (Glycoengineered) Antibodies

The full antibody heavy and light chain DNA sequences have been obtained by subcloning the variable regions in frame with either the constant heavy chain or the constant light chain pre-inserted into the respective recipient mammalian expression vector. The antibody expression was driven by an MPSV promoter and the vector carries a synthetic polyA signal sequence at the 3' end of the CDS. In addition each vector contains an EBV OriP sequence.

Antibodies are produced by co-transfecting HEK293-EBNA cells with the mammalian antibody expression vectors using a calcium phosphate-transfection. Exponentially growing HEK293-EBNA cells are transfected by the calcium phosphate method. Alternatively, HEK293 cells growing in suspension are transfected by polyethylenimine. For the production of unmodified non-glycoengineered antibody, the cells are transfected only with antibody heavy and light chain expression vectors in a 1:1 ratio.

For the production of the glycoengineered antibody, the cells are co-transfected with two additional plasmids, one for a fusion GnTIII polypeptide expression (a GnT-III expression vector), and one for mannosidase II expression (a Golgi mannosidase II expression vector) at a ratio of 4:4:1:1, respectively. Cells are grown as adherent monolayer cultures in T flasks using DMEM culture medium supplemented with 10% FCS, and are transfected when they are between 50 and 80% confluent. For the transfection of a T150 flask, 15 million cells are seeded 24 hours before transfection in 25 ml DMEM culture medium supplemented with FCS (at 10% V/V final), and cells are placed at 37° C. in an incubator with a 5% $CO_2$ atmosphere overnight. For each T150 flask to be transfected, a solution of DNA, $CaCl_2$ and water is prepared by mixing 94 µg total plasmid vector DNA divided equally between the light and heavy chain expression vectors, water to a final volume of 469 µl and 469 µl of a 1M $CaCl_2$ solution. To this solution, 938 µl of a 50 mM HEPES, 280 mM NaCl, 1.5 mM $Na_2HPO_4$ solution at pH 7.05 are added, mixed immediately for 10 sec and left to stand at room temperature for 20 sec. The suspension is diluted with 10 ml of DMEM supplemented with 2% FCS, and added to the T150 in place of the existing medium. Then additional 13 ml of transfection medium are added. The cells are incubated at 37° C., 5% $CO_2$ for about 17 to 20 hours, then medium is replaced with 25 ml DMEM, 10% FCS. The conditioned culture medium is harvested approx. 7 days post-media exchange by centrifugation for 15 min at 210×g, the solution is sterile filtered (0.22 um filter) and sodium azide in a final concentration of 0.01% w/v is added, and kept at 4° C.

The secreted wildtype or glycoengineered afucosylated antibodies are purified from cell culture supernatants by affinity chromatography using Protein A (HiTrap ProtA, GE Healthcare) affinity chromatography. Briefly, the column was equilibrated with 20 mM sodium phosphate, 20 mM sodium citrate pH 7.5, the cell supernatant was loaded, followed by a first wash with 20 mM sodium phosphate, 20 mM sodium citrate pH 7.5, and a second wash with 13.3 mM sodium phosphate, 20 mM sodium citrate, 500 mM sodium chloride pH 5.45. The antibodies were eluted with 20 mM sodium citrate, 100 mM sodium chloride, 100 mM glycine pH 3. In a subsequent size exclusion chromatographic step on a HiLoad Superdex 200 column (GE Healthcare) the buffer was exchanged to 25 mM potassium phosphate, 125 mM sodium chloride, 100 mM glycine solution of pH 6.7 or alternatively 140 mM sodium chloride, 20 mM histidine, pH 6.0 and the pure monomeric IgG1 antibodies were collected. If required an additional cation exchange chromatography step is included between the two standard purification steps.

The protein concentration of purified protein samples is determined by measuring the optical density (OD) at 280 nm, using the molar extinction coefficient calculated on the basis of the amino acid sequence. Purity and molecular weight of antibodies are analyzed by SDS-PAGE in the presence and absence of a reducing agent (5 mM 1,4-dithiotreitol) and staining with Coomassie (SimpleBlue™ SafeStain from Invitrogen). The NuPAGE® Pre-Cast gel system (Invitrogen, USA) is used according to the manufacturer's instruction (4-20% Tris-Glycine gels or 3-12% Bis-Tris). The aggregate content of antibody samples is analyzed using a Superdex 200 10/300GL analytical size-exclusion column (GE Healthcare, Sweden) in 2 mM MOPS, 150 mM NaCl, 0.02% $NaN_3$, pH 7.3 running buffer at 25° C. The integrity of the amino acid backbone of reduced antibody light and heavy chains is verified by NanoElectrospray Q-TOF mass spectrometry after removal of N-glycans by enzymatic treatment with Peptide-N Glycosidase F (Roche Molecular Biochemicals).

Figure 7:
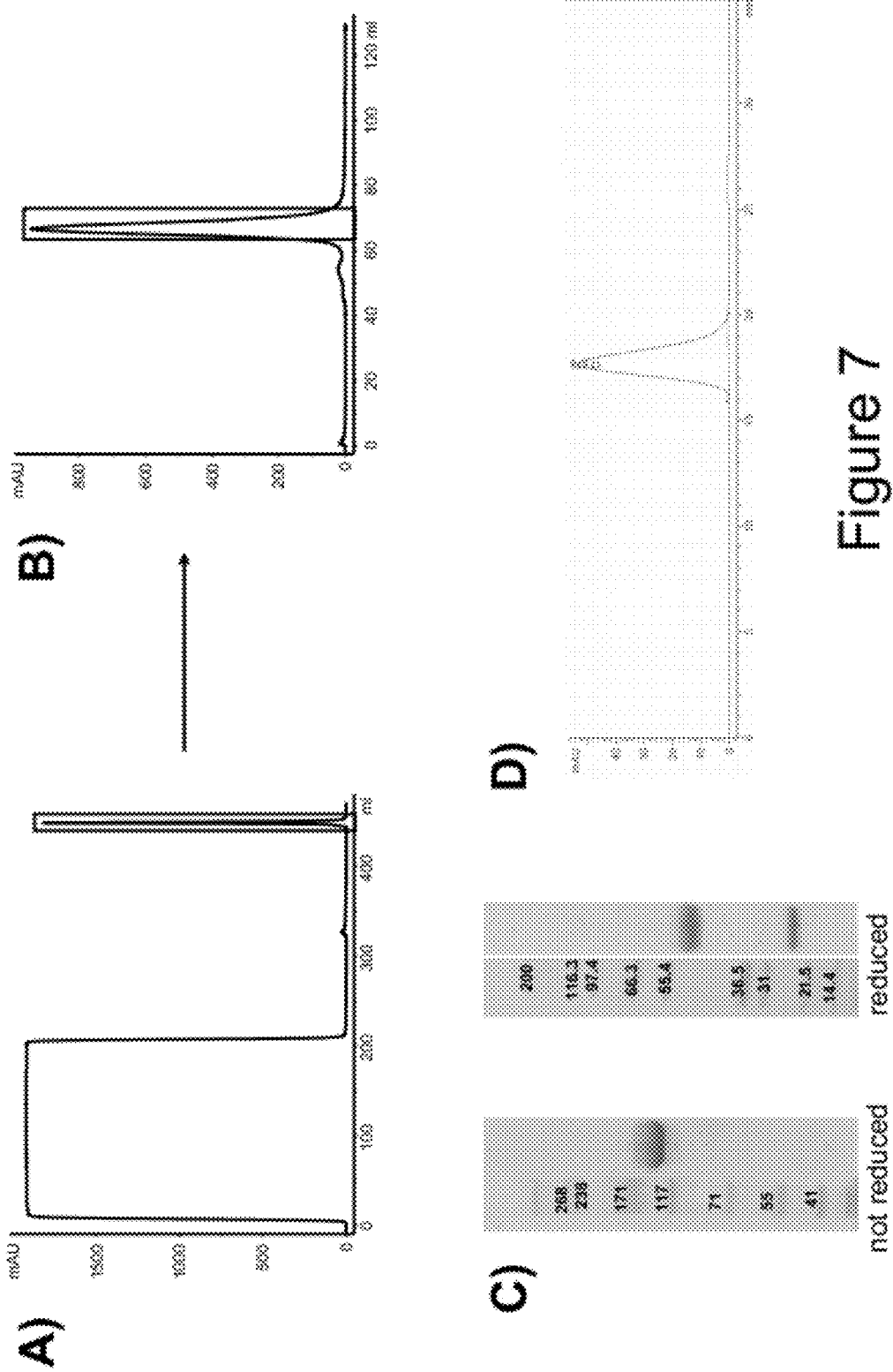
FIG. 7 shows the purification and analysis of the glycoengineered 2B10 human IgG. A) Protein A affinity chromatography purification step. B) Size exclusion chromatography purification step. C) Analytical SDS PAGE. D) Analytical size exclusion chromatography. Experimental producers are described in Example 1.

The results of the purification and analysis of the wild-type and glycoengineered 2B10 human IgG antibodies are shown in FIGS. 6 and 7.

The oligosaccharides attached to the Fc region of the antibodies are analysed by MALDI TOF-MS as described below. Oligosaccharides are enzymatically released from the antibodies by PNGaseF digestion. The resulting digest solution containing the released oligosaccharides is either prepared directly for MALDI TOF-MS analysis or is further digested with EndoH glycosidase prior to sample preparation for MALDI TOF-MS analysis.

Analysis of Glycostructure of (Glycoengineered) Antibodies

For determination of the relative ratios of fucose- and non-fucose (a-fucose) containing oligosaccharide structures, released glycans of purified antibody material are analyzed by MALDI-Tof-mass spectrometry. The antibody sample (about 50 µg) is incubated overnight at 37° C. with 5 mU N-Glycosidase F (QAbio; PNGaseF: E-PNG01) in 2 mM Tris, pH 7.0, in order to release the oligosaccharide from the protein backbone. For deamination of glycans acetic acid to a final concentration of 150 mM is added and incubated for 1 h at 37° C. For analysis by MALDI TOF mass spectrometry, 2 µL of the sample are mixed on the MALDI target with 2 µL DHB matrix solution (2,5-dihydroxybenzoic acid [Bruker Daltonics #201346] dissolved in 50% ethanol/5 mM NaCl at 4 mg/ml) and analysed with MALDI TOF Mass Spectrometer Autoflex II instrument [Bruker Daltonics]. Routinely, 50-300 shots are recorded and summed up to a single experiment. The spectra obtained are evaluated by the flex analysis software (Bruker Daltonics) and masses are determined for the each of the peaks detected. Subsequently, the peaks are assigned to fucose or a-fucose (non-fucose) containing carbohydrate structures by comparing the masses calculated and the masses theoretically expected for the respective structures (e.g. complex, hybrid and oligo- or high-mannose, respectively, with and without fucose).

For determination of the ratio of hybrid structures, the antibody samples are digested with N-Glycosidase F and Endo-Glycosidase H [QAbio; EndoH: E-EH02] concomitantly. N-Glycosidase F releases all N-linked glycan structures (complex, hybrid and oligo- and high mannose structures) from the protein backbone and the Endo-Glycosidase H cleaves all the hybrid type glycans additionally between the two N-acetylglucosamine (GlcNAc) residues at the reducing end of the glycan. This digest is subsequently treated and analysed by MALDI TOF mass spectrometry in the same way as described above for the N-Glycosidase F digested sample. By comparing the pattern from the N-Glycosidase F digest and the combined N-glycosidase F/Endo H digest, the degree of reduction of the signals of a specific carbohydrate structure is used to estimate the relative content of hybrid structures. The relative amount of each carbohydrate structure is calculated from the ratio of the peak height of an individual structure and the sum of the peak heights of all oligosaccharides detected. The amount of fucose is the percentage of fucose-containing structures related to all carbohydrate structures identified in the N-Glycosidase F treated sample (e.g. complex, hybrid and oligo- and high-mannose structures, resp.). The amount of non-fucosylation is the percentage of fucose-lacking structures related to all carbohydrates identified in the N-Glycosidase F treated sample (e.g. complex, hybrid and oligo- and high-mannose structures, resp.).

The degree of non-fucosylation as determined by MALDI-TOF MS for the 2B10 human IgG antibodies was 8.1% for the wild-type version and 83% for the glycoengineered version.

Example 2

Construction of Generic Fab-Libraries

Generic antibody libraries in the Fab-format were constructed on the basis of human germline genes using the following V-domain pairings: Vk3_20 kappa light chain with VH3_23 heavy chain for the DP47-3 library and Vk1_17 kappa light chain with VH1_69 heavy chain for the DP88-3 library. See SEQ ID NOs 1 and 2.

Both libraries were randomized in CDR3 of the light chain (L3) and CDR3 of the heavy chain (H3) and were assembled from 3 fragments per library by splicing by overlapping extension (SOE) PCR. Fragment 1 comprises the 5' end of the antibody gene including randomized L3, fragment 2 is a central constant fragment spanning from L3 to H3, whereas fragment 3 comprises randomized H3 and the 3' portion of the antibody gene.

The following primer combinations were used to generate library fragments for DP47-3 library: fragment 1 (LMB3-LibL1b_new), fragment 2 (MS63-MS64), fragment 3 (Lib2H-fdseqlong). See Table 3. The following primer combinations were used to generate library fragments for the DP88-3 library: fragment 1 (LMB3-RJH_LIB3), fragment 2 (RJH31-RJH32) and fragment 3 (LIB88_2-fdseqlong). See Table 4.

TABLE 3

| Primers Used In the DP47-3 Library | | SEQ ID NO |
|---|---|---|
| LMB3 | CAGGAAACAGCTATGACCATGATTAC | 116 |
| LibL1b_new | CACTTTGGTCCCCTGGCCGAACGTMNNGGGMN NMNNMNNACCCTGCTGACAGTAATACACTGC | 117 |
| MS63 | TTTCGCACAGTAATATACGGCCGTGTCC | 118 |
| MS64 | ACGTTCGGCCAGGGGACCAAAGTGG | 119 |
| Lib2H | GGCCGTATATTACTGTGCGAAANNKNNKNNKN NKNNKTTTGACTACTGGGGCCAAGGAAC | 120 |
| fdseqlong | GACGTTAGTAAATGAATTTTCTGTATGAGG | 121 |

TABLE 4

| Primers Used in DP88-3 Library | | SEQ ID NO |
|---|---|---|
| LMB3 | CAGGAAACAGCTATGACCATGATTAC | 116 |
| RJH_LIB3 | GACTTTGGTGCCCTGGCCAAACGT MNN GGG MNN MNN ACC MNN CTGCAAGCAGTAATAGGTGGCAAAATC | 122 |
| RJH31 | ACGTTTGGCCAGGGCACCAAAGTCGAG | 123 |
| RJH32 | TCTCGCACAGTAATACACGGCGGTGTCC | 124 |
| LIB88_2 | GGACACCGCCGTGTATTACTGTGCGAGA-[(33% GAC Asp; 26% GGT Gly; 10% GAA Glu; 9% CGT Arg; 7% Lys; 6% GTT Val; 5% TCT Ser; 4% CTG Leu)1 - (23% GGT Gly; 17% TAC Tyr; 16% TCT Ser; 11% GCT Ala; 9% CGT Arg; 7% AAC Asn; 6% ACT Thr; 6% GTT Val; 5% CCG Pro)8]-TTTGACTACTGGGGCCAAGGGACCACCGTGACCGTCTCC | 125 |
| fdseqlong | GACGTTAGTAAATGAATTTTCTGTATGAGG | 121 |

The PCR protocol for the production of library fragments included: 5 minutes of initial denaturation at 94° C.; 25 cycles of 1 minute at 94° C., 1 minute at 58° C., and 1 minute at 72° C.; and terminal elongation for 10 minutes at 72° C. For assembly PCR, equimolar ratios of the 3 fragments were used as template. The assembly PCR protocol included: 3 minutes of initial denaturation at 94° C.; and 5 cycles of 30 seconds at 94° C., 1 minute at 58° C., and 2 minutes at 72° C. At this stage, primers complementary to sequence outside fragments 1-3 were added and an additional 20 cycles were performed prior to a terminal elongation for 10 min at 72° C. After assembly of sufficient amounts of full length randomized Fab constructs, the Fab constructs were digested with NcoI/NotI for the DP47-3 library and with NcoI/NheI for the DP88-3 library alongside with similarly treated acceptor phagemid vector. For the DP47-3 library, 22.8 µg of Fab library was ligated with 16.2 µg of phagemid vector. For the DP88-3 library, 30.6 µg of Fab library was ligated with 30.6 µg of phagemid vector.

Purified ligations were used for 68 transformations for the DP47-3 library and 64 transformations for the DP88-3 library, respectively, to obtain final library sizes of $4.2 \times 10^{10}$ for DP47-3 and $3.3 \times 10^9$ for DP88-3. Phagemid particles displaying the Fab libraries were rescued and purified by PEG/NaCl purification to be used for selections.

Example 3

Selection of Anti-TNC A2 Clone 2B10 (Primary Selections)

Selections were carried out against *E. coli*-expressed human TNC-A2 which was subcloned 5' of an avi-tag and 6×his-tag. See SEQ ID NO: 97.

The antigen was biotinylated in vivo upon expression. Selections have been carried out in solution according to the following protocol: (i) binding of ~$10^{12}$ phagemid particles of library DP88-3 and 100 nM biotinylated human TNC A2 for 0.5 hours in a total volume of 1 ml; (ii) capture of biotinylated human TNC-A2 and attached phage by the addition of $5.4 \times 10^7$ streptavidin-coated magnetic beads for 10 minutes; (iii) washing of beads using 5×1 ml PBS/Tween20 and 5×1 ml PBS; (iv) elution of phage particles by the addition of 1 mL 100 mM TEA (triethylamine) for 10 minutes and neutralization by the addition of 500 µL 1M Tris/HCl pH 7.4; and (v) re-infection of log-phase *E. coli* TG1 cells, infection with helperphage VCSM13 and subsequent PEG/NaCl precipitation of phagemid particles to be used in subsequent selection rounds.

Selections were carried out over 3 rounds using constant antigen concentrations at 100 nM. In round 2, capture of antigen:phage complexes was performed on neutravidin plates instead of streptavidin beads. Specific binders were identified by ELISA as follows using: 100 µl of 100 nM biotinylated human TNC-A2 was coated in each well of neutravidin plates.

Fab-containing bacterial supernatants were added and binding Fabs were detected via their Flag-tags by using an anti-Flag/HRP secondary antibody. Once identified, clone 2B10 was bacterially expressed in a 0.5 liter culture volume, affinity purified and further characterized by SPR-analysis using BIACORE T100. See SEQ ID NOs: 56 and 60.

Example 4

Construction of Anti-TNC A2 Affinity Maturation Libraries Based on Clone 2B10

An affinity maturation library was constructed on the basis of a pre-selected antibody from the primary TNC A2 selections. More precisely, it was based on parental clone 2B10 and consisted of two sub-libraries: 1) $V_L$ sub-library, randomized in CDR1 and CDR2 of the light chain (L1/L2) and 2) $V_H$ sub-library, randomized in CDR1 and CDR2 of the heavy chain (H1/H2). These sub-libraries were pooled upon transformation. Each of these sub-libraries was constructed by four subsequent steps of amplification and assembly. For L1/L2 libraries: 1) amplification of fragment 1 (LMB3-AM_Vk1A30_L1_ba) and fragment 2 (RJH50 (Vk1A30_L1/L2_fo)-RJH51 (Vk1A30_BsiWI_ba)), 2) assembly of fragments 1 and 2 using outer primers LMB3 and RJH51 (Vk1A30_BsiWI_ba) to create the template for 3) amplification of fragment 3 (LMB3-AM_Vk1A30_L2_ba) and fragment 4 (RJH52 (Vk1A30_L2/L3)-RJH51 (Vk1A30_BsiWI_ba)) and 4) final assembly of fragments 3 and 4 using the same outer primers as above. For H1/H2 libraries: 1) amplification of fragment 1 (RJH53-AM_DP88_H1_ba_opt) and fragment 2 (RJH54(DP88_H1/H2_fo)-MS52), 2) assembly of fragments 1 and 2 using outer primers RJH53 and MS52 to create the template for 3) amplification of fragment 3 (RJH53-AM_DP88_H2_ba) and fragment 4 (RJH55 (DP88_H2H3_fo)-MS52) and 4) final assembly of fragments 3 and 4 using the same outer primers as above. Final assembly products have been digested NcoI/BsiWI for $V_L$ sub-libraries and MunI and NheI for $V_H$ sub-libraries and were cloned in similarly digested acceptor vectors. Library size resulted in $1.16 \times 10^{10}$ independent clones.

TABLE 5

| Primers used in L1/L2 Affinity Maturation Libraries for Anti-TNC A2 binder 2B10 | | SEQ ID NO |
|---|---|---|
| LMB3 | CAGGAAACAGCTATGACCATGATTAC | 116 |
| AM_Vk1A30_L1_ba | CCTGGCTTCTGCTGGTACCAGCCTAAATCATTA CGAATGCCCTGACTTGCCCGGCAGGTGATG | 126 |
| RJH50(Vk1A30_L1/L2_fo) | GCTGGTACCAGCAGAAGCCAGGGAAAG | 127 |
| RJH51(Vk1A30_BsiWI_ba) | GGTGCAGCCACCGTACGCTTGATCTC | 128 |
| AM_Vk1A30_L2_ba | CTTGATGGGACGCCACTCTGCAAACTGGACGCA GCATAGATCAGGCGCTTAGGGGCTTTCC | 129 |
| RJH52(Vk1A30_L2/L3) | TTGCAGAGTGGCGTCCCATCAAGGTTC | 130 |

Underline: 60% original base and 40% randomization as V

Bold: 60% original base and 40% randomization as N

TABLE 6

Primers used in H1/H2 Affinity Maturation Libraries for Anti-TNC A2 binder 2B10

| | | SEQ ID NO |
|---|---|---|
| RJH53 | CATCAGGGCCTGAGCTCGCCCGTCAC | 131 |
| AM_DP88_H1_ba_opt | GTCCAGGGGCCTGTCGCACCCAGCTTATAGCGTAGCTGCTGAATGTGCCTCCGGAGGCCTTG | 132 |
| RJH54(DP88_H1/H2_fo) | ATAAGCTGGGTGCGACAGGCCCCTGGAC | 133 |
| MS52 | GAAGACCGATGGCCTTTGGTGCTAG | 134 |
| AM_DP88_H2_ba | GACCCTGCCCTGGAACTTCTGTGCGTAGTTTGCGGTACCAAAGATAGGGATGATCCCTCCCATCCACTCGAGCCCTTGTCCAG | 135 |
| RJH55(DP88_H2H3_fo) | TACGCACAGAAGTTCCAGGGCAGGGTCAC | 136 |

Underligned: 60% original base and 40% randomization as V
Bold: 60% original base and 40% randomization as N Example 5

Selection of Affinity-Matured Anti-TNC A2 Clones

Selections were carried out against E. coli expressed human TNC A2 which was cloned upstream an avi-tag and 6×his-tag (see SEQ ID NO: 97). The antigen was biotinylated in vivo upon expression. Selections have been carried out in solution as described for the primary TNC A2 selections using decreasing concentrations of human TNC A2 ranging from 100 to 2 nM. After identification of affinity-matured clones by ELISA, secondary screenings were carried out using a ProteOn XPR36 biosensor (Biorad) and kinetic rate constants and affinities were determined analyzing affinity-purified Fab preparations on the same instrument. $K_D$ was measured by surface plasmon resonance using a ProteOn XPR36 machine (Biorad) at 25° C. with antigens immobilized on NLC sensor chips (Biorad). Briefly, recombinant antigen was diluted to 10 μg/ml in PBS/0.005% Tween-20, pH 7.4 and injected at 30 μg/min for 100 to 300 s to achieve approximately 200-800 response units (RU) of coupled antigen. For one-shot kinetic measurements, two-fold dilution series of purified Fabs (concentration range between ~0.01 nM and 25 nM) were injected at a flow rate of 100 μl/min. Association time was 210 s, dissociation time 600 s. The sensorchip was regenerated by injection of 50 mM NaOH for 18 s at a flow rate of 100 μl/min. Association rates ($k_{on}$) and dissociation rates ($k_{off}$) were calculated using a simple one-to-one Langmuir binding model (ProteOn manager software version 2.1) by simultaneously fitting the association and dissociation sensorgrams. The equilibrium dissociation constant ($K_D$) is calculated as the ratio $k_{off}/k_{on}$.

The following affinity-matured clones were identified: 2B10_O1F7 (see SEQ ID NOs: 85 and 87), 2B10_6H10 (see SEQ ID NOs: 89 and 91), 2B10_C3A6 (see SEQ ID NOs: 69 and 71), 2B10_D1A2 (see SEQ ID NOs: 73 and 75), and 2B10_O7D8 (see SEQ ID NOs: 81 and 83) (all of these are derived from the $V_L$ sub-library), as well as 2B10_C3B6 (see SEQ ID NOs: 61 and 63) and 2B10_6A12 (see SEQ ID NOs: 65 and 67) (these two clones are derived from the $V_H$ sub-library). Moreover, for clone 2B10_D1A2, a V32D mutant was generated (see SEQ ID NOs: 77 and 79) (numbering according to Kabat).

FIG. 1 shows the Surface Plasmon Resonance sensorgrams of the selected affinity matured Fabs binding to immobilized TNC A2, and Table 7 gives the respective affinities derived. The selected Fabs span a high affinity range in the pM range.

TABLE 7

Summary of kinetic equilibrium constants ($K_D$) of affinity-matured anti-TNC A2 antibodies as Fab fragments (monovalent binding).

| antibody | affinity (KD) to hu TNC A2 [pM] |
|---|---|
| 2B10_C3B6 | 191 |
| 2B10_6A12 | 290 |
| 2B10_C3A6 | 497 |
| 2B10_O7D8 | 147 |
| 2B10_O1F7 | 56 |
| 2B10_6H10 | 810 |

Example 6

IgG Conversion of 2B10 Fabs Binding TNC A2

The parental 2B10 Fab and the affinity matured 2B10 Fab derivatives have been converted into a human IgG1 format, a mouse IgG2a format and a human IgG1 format with an Avi Tag fused to the C-terminus of the heavy chain. The affinity matured 2B10 Fabs were converted into mouse IgG to allow immunohistochemical analysis (see Example 8)

The full antibody heavy and light chain DNA sequences were obtained either by subcloning the variable regions in frame with the respective constant heavy and the constant light chain regions pre-inserted into different recipient mammalian expression vectors or were recombined by fusing a short sequence stretch homologous to the recipient vectors insertion site. The recombination was performed according to the "In-Fusion Cloning System" from Invitrogen.

In all vectors the antibody expression is driven by an MPSV promoter and all vectors carry a synthetic polyA signal sequence at the 3' end of the CDS. In addition each vector contains an EBV OriP sequence.

Example 7

Determination of Affinity of 2B10 Fab and IgG to TNC A2

The affinity of the TNC A2 2B10 Fab fragment as well as of the human IgG1 converted TNC A2 2B10 antibody was subsequently determined and confirmed for human, murine and cynomolgus TNC A2 domain by surface plasmon resonance using a BIACORE® T100 machine (GE Healthcare) at 25° C. For this purpose the biotinylated antigens (expressed in E. coli, antigen in context but not glycosylated) were immobilized on a streptavidin chip and the constructs were used as analytes. For immobilization the antigens were diluted with HBS-EP+ (GE Healthcare, 10 mM HEPES, 150 mM NaCl, 3 mM EDTA, 0.05% Surfactant P20, pH 7.4) to 0.1 µg/ml before injection at a flow rate of 10 µl/minute to achieve approximately 80 response units (RU) of coupled protein. The TNC A2 domain from man, mouse and cynomolgus monkey was expressed in the context of the domains A1 and A3. The antigen constructs comprising the fifth fibronectin type III domain of human TNC (Fn5), the A1 and A2 domain of either human, murine or cynomolgus TNC, and the A3 domain of human TNC (TNC Fn5-A1-human/murine/cynoA2-A3) are shown in SEQ ID NOs 99-104.

For kinetics measurements, two-fold serial dilutions of Fab fragments (range between 1.56 nM to 100 nM) or IgG (range between 0.39 nM to 25 nM) were injected in HBS-EP+ at 25° C. at a flow rate of 50 µl/min. Association and dissociation times were 180 s and a regeneration with 10 mM glycine pH 1.5 for 60 s was performed between cycles. Association rates ($k_{on}$) and dissociation rates ($k_{off}$) were calculated using a simple one-to-one Langmuir binding model (BIACORE® T100 Evaluation Software version 1.1.1) by simultaneously fitting the association and dissociation sensorgrams. The equilibrium dissociation constant ($K_D$) was calculated as the ratio $k_{off}/k_{on}$. See, e.g., Chen et al., J Mol Biol 293, 865-881 (1999)

TNC domains 1 to 8 produced in HEK served as negative control (see SEQ ID 105 and 106). The $K_D$ values of binding are given in Table 8. FIG. 2 A-B shows the corresponding SPR-based kinetic analyses.

TABLE 8

Summary of kinetic equilibrium constants ($K_D$) of 2B10 anti-TNC A2 antibodies as Fab fragments and as IgG

| Construct | Human TNC | Murine TNC | Cyno TNC |
|---|---|---|---|
| IgG 2B10 Immob E. coli Ag | Avidity: 0.29 nM | Avidity: 1.9 nM | Avidity: 0.21 nM |
| Fab fragment 2B10 Immob E. coli Ag | Affinity: 1.8 nM | Affinity: 180 nM | Affinity: 17 nM |

Example 8

Figure 3B:
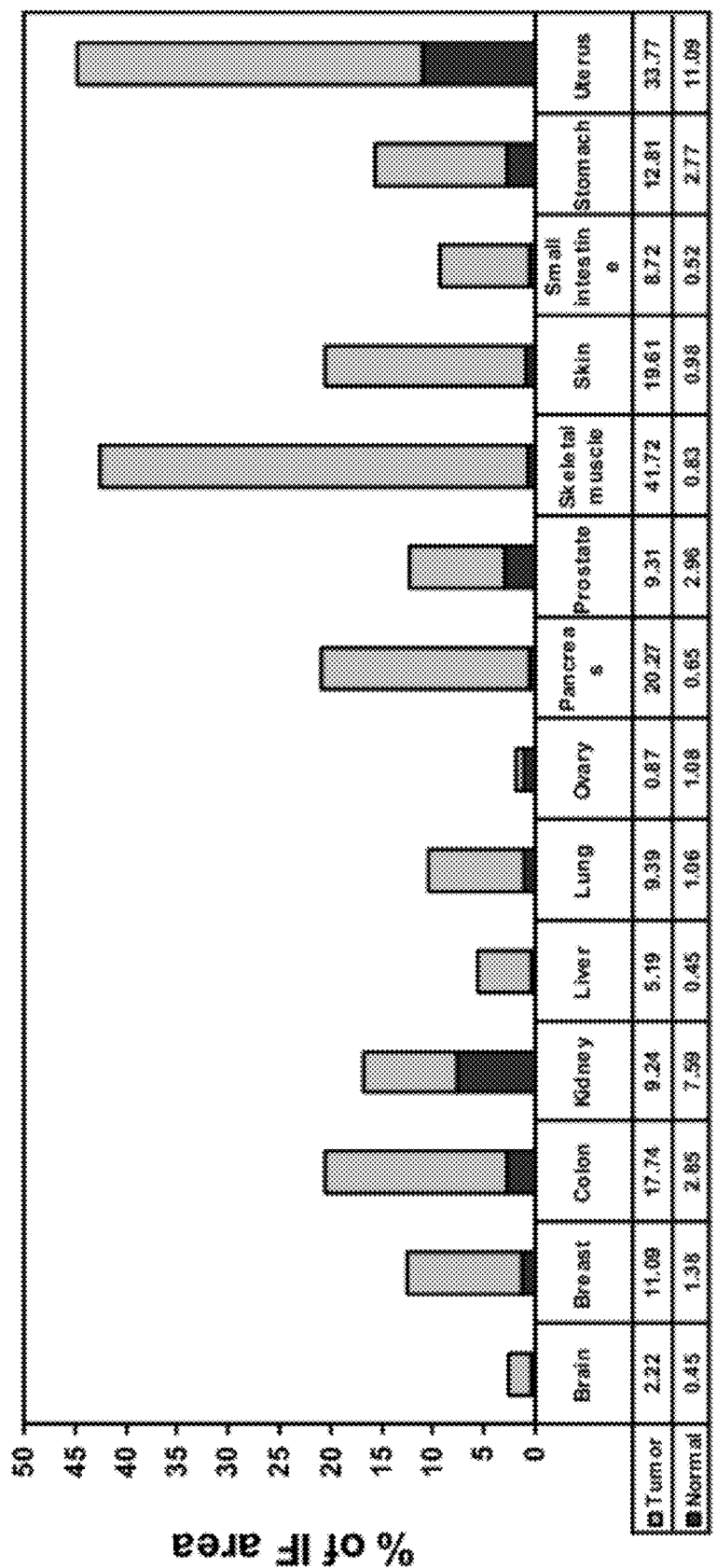
Figure 4A:
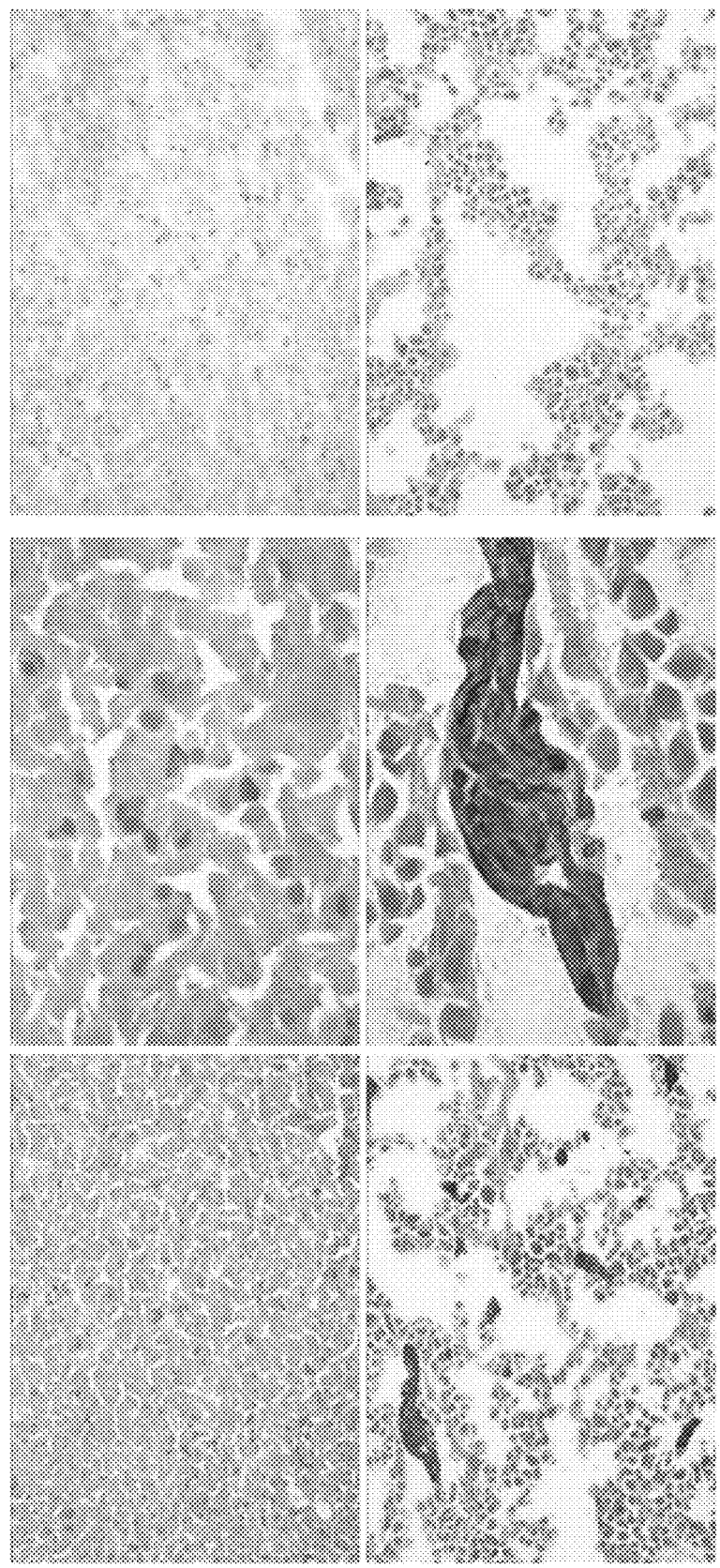
FIG. 4(A) to (N), shows immunohistochemical images of human tissue at 100× (left panels) and 400× (middle panels) magnification stained with SHD2B10-mouse IgG as described in Example 8. Staining with isotype control antibody is shown at 100× magnification (right panels). Upper panels: normal tissue, lower panels: tumor tissue. (A) brain, (B) breast, (C) colon, (D) kidney, (E) liver, (F) lung, (G) ovary, (H) pancreas, (I) prostate, (J) skeletal muscle, (K) skin, (L) small intestine, (M) stomach, (N) uterus.
Figure 4B:
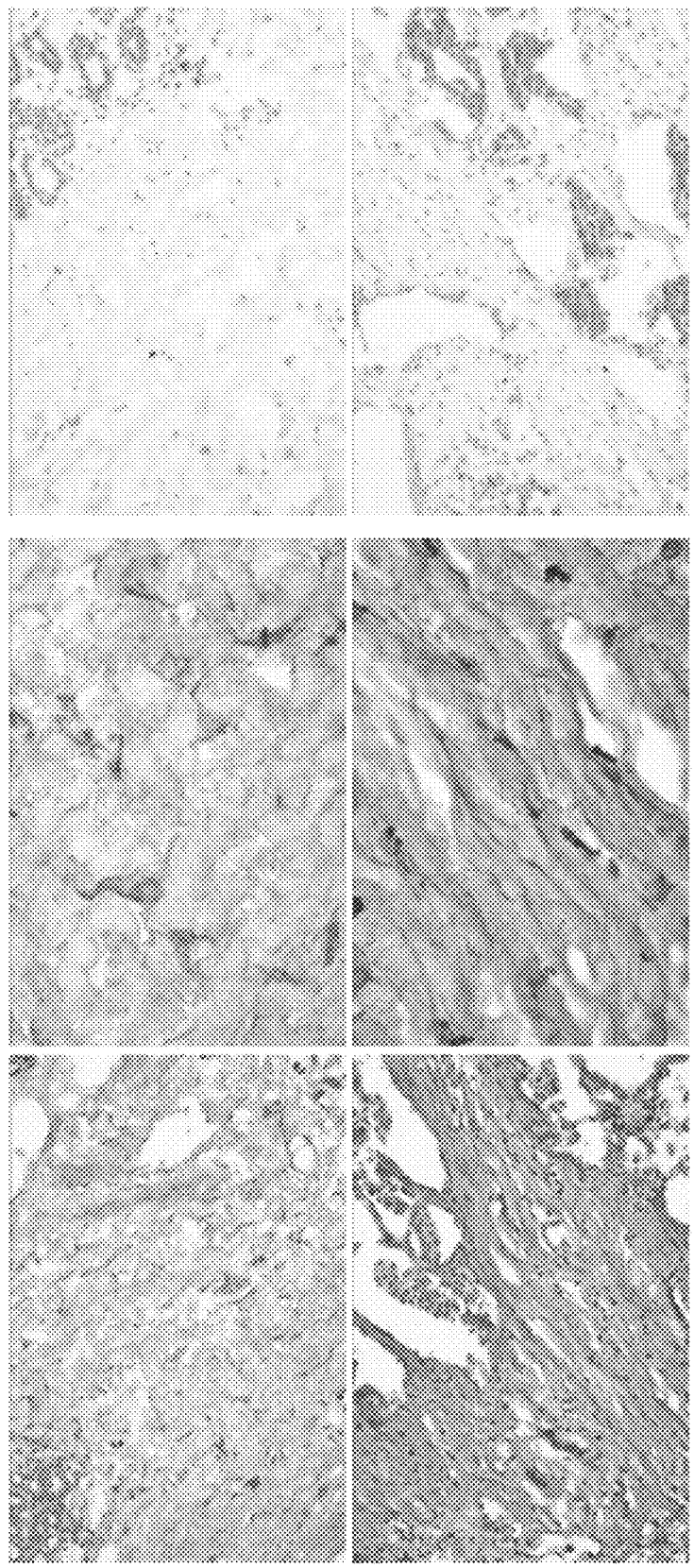
Figure 4C:
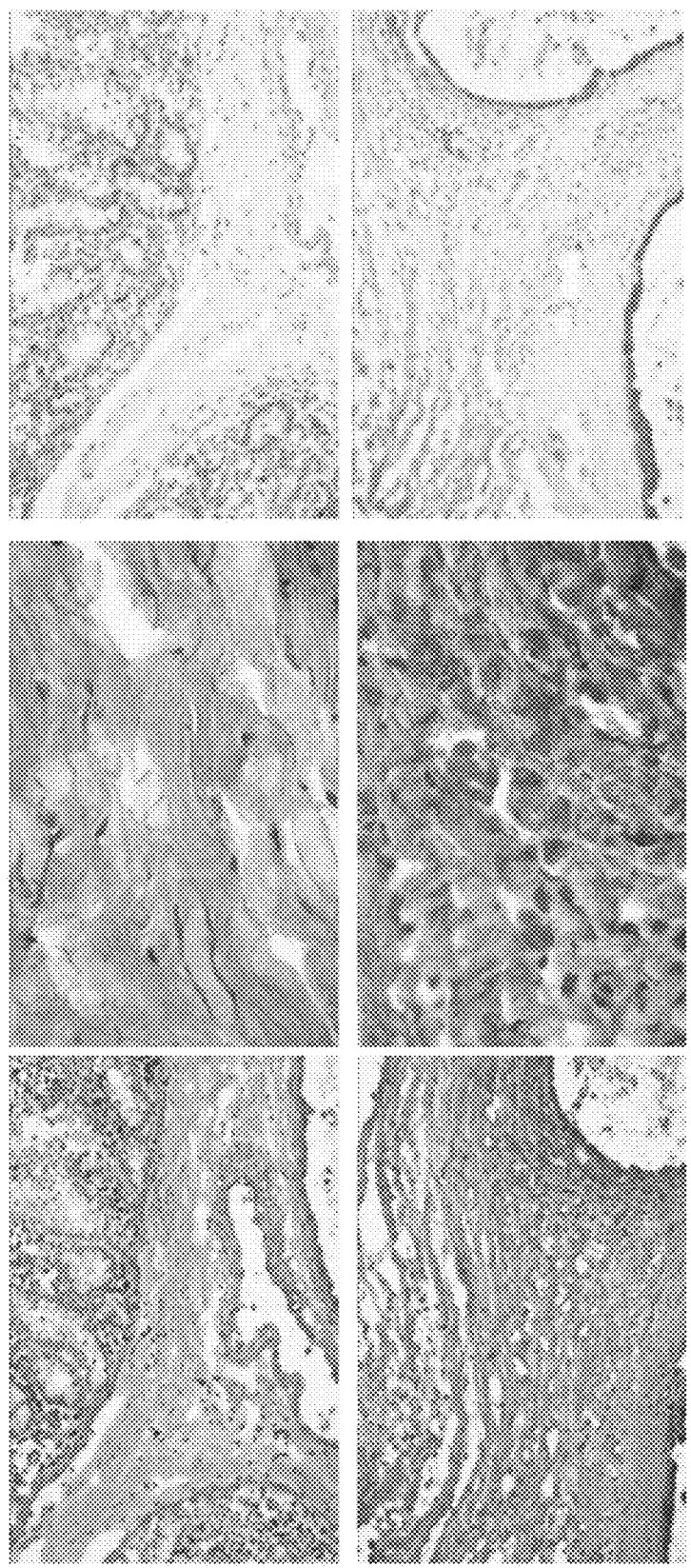
Figure 4D:
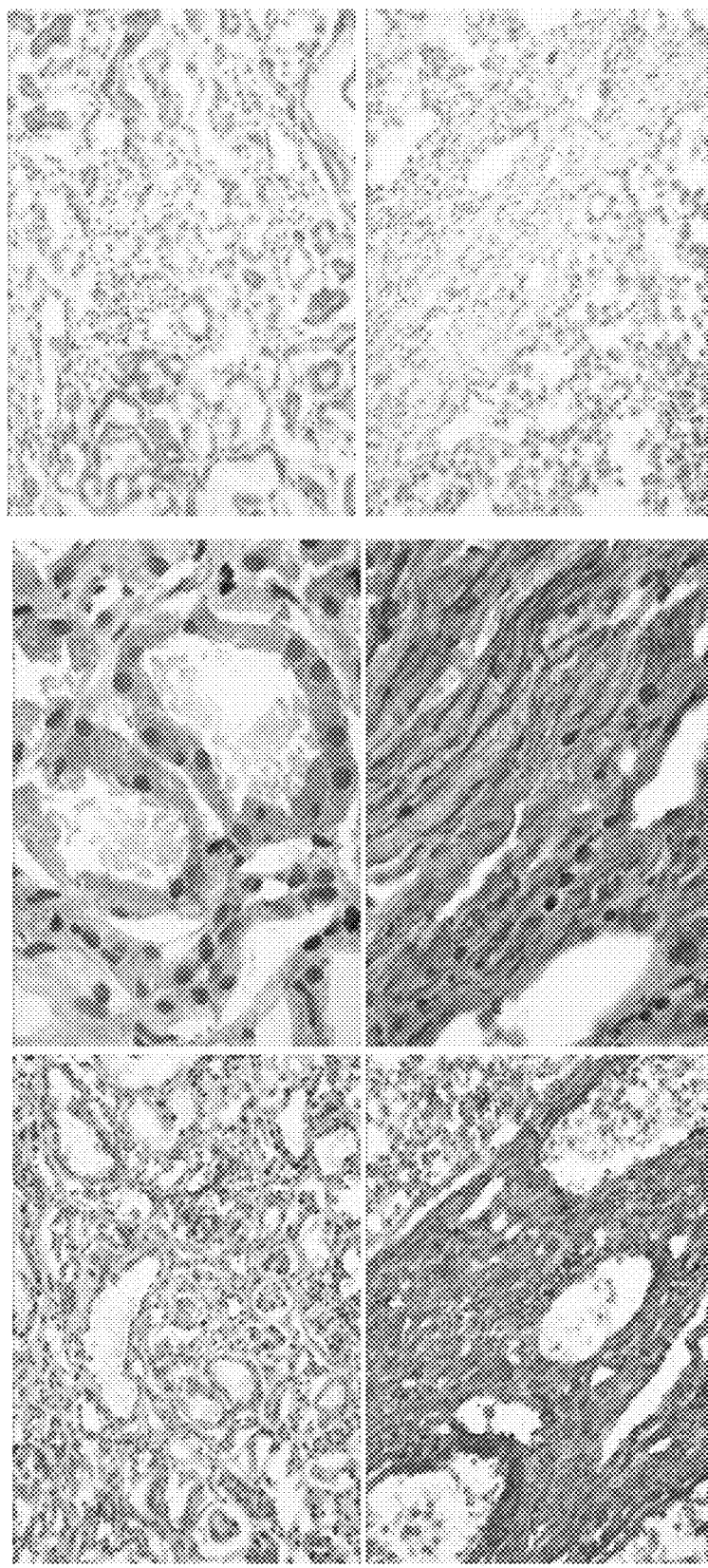
Figure 4E:
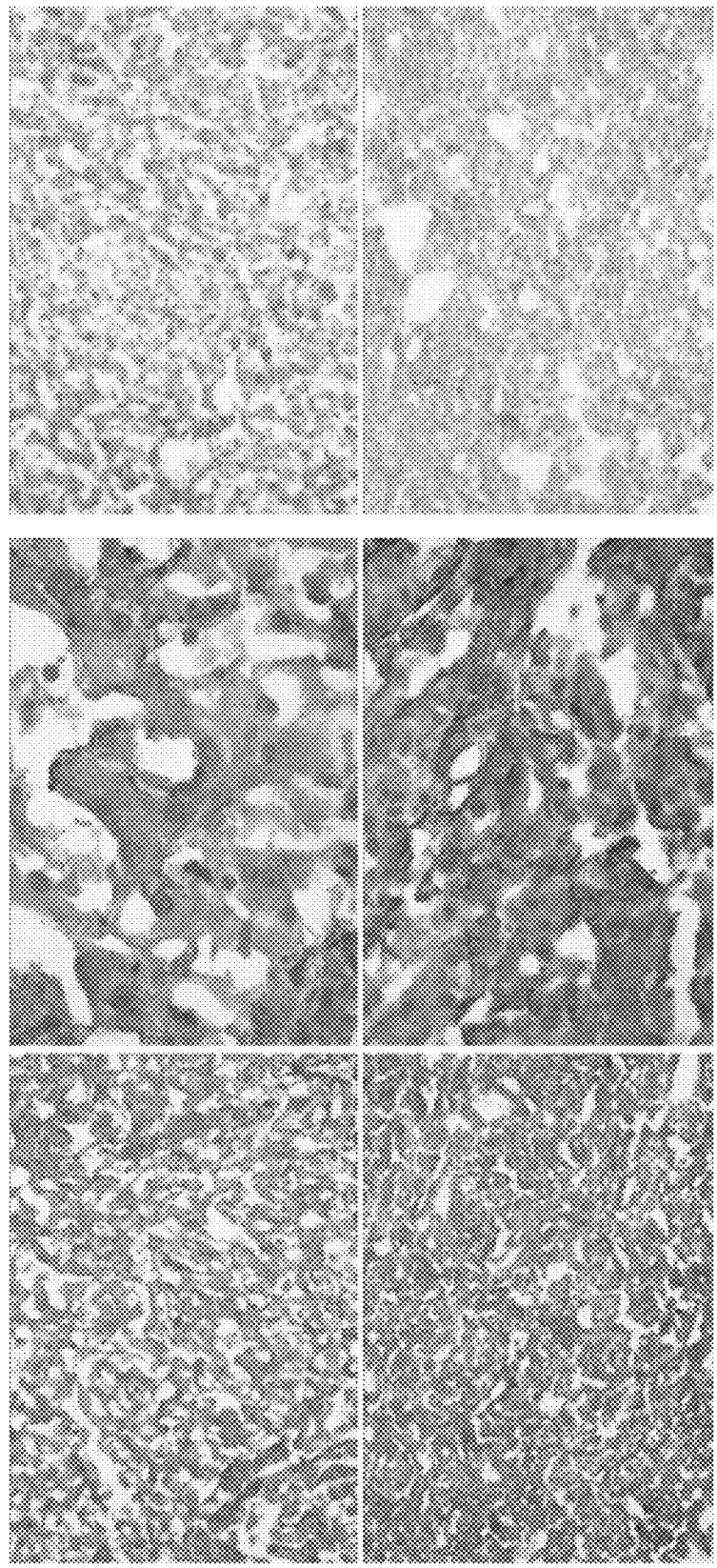
Figure 4F:
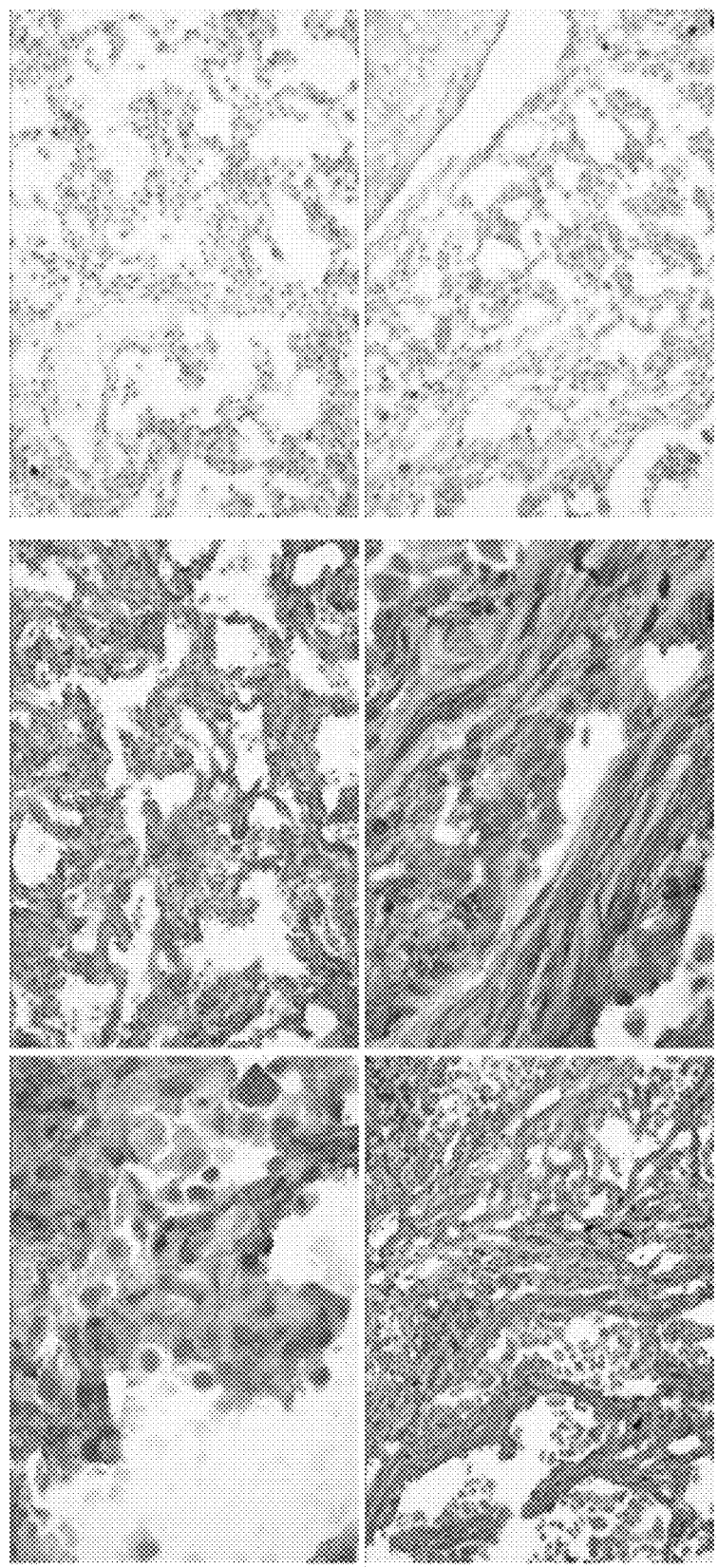
Figure 4H:
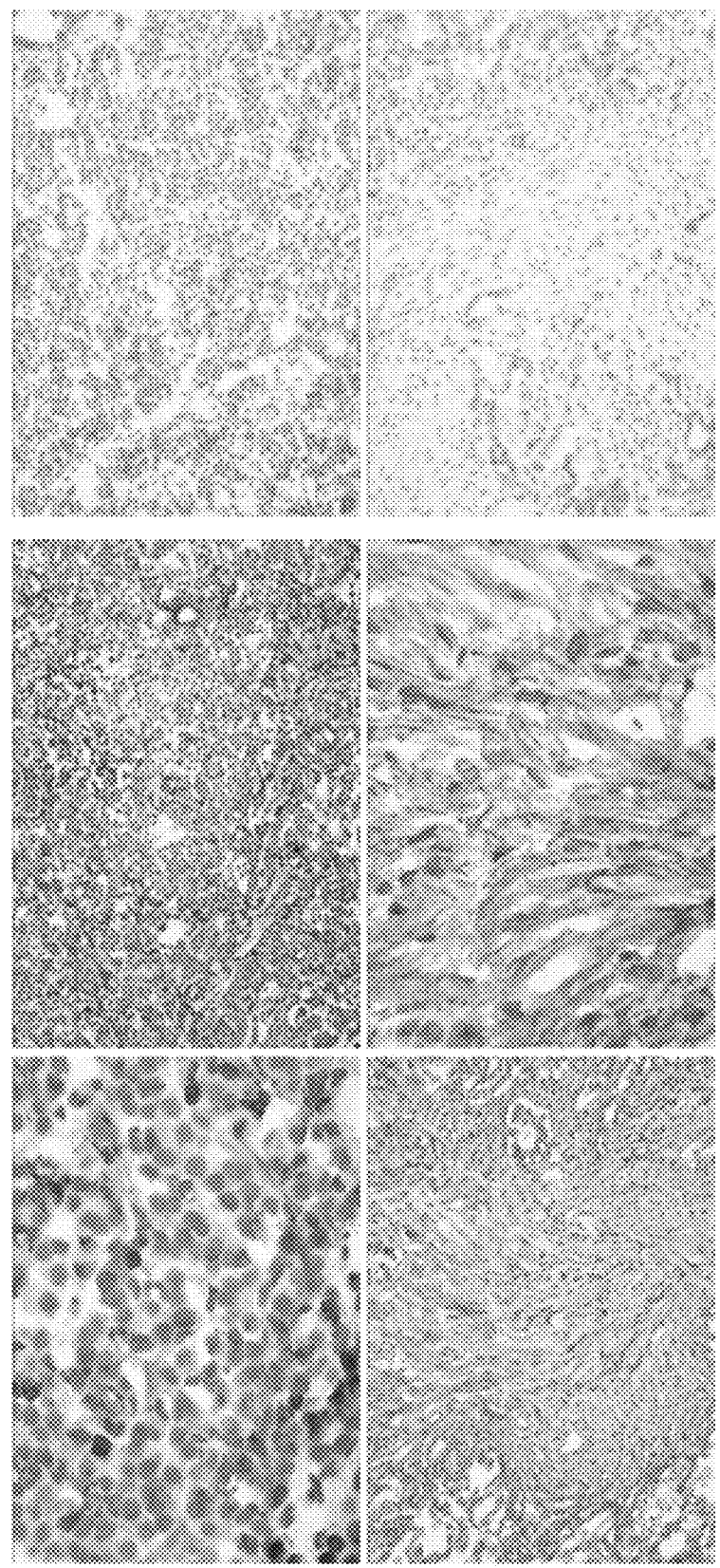
Figure 4I:
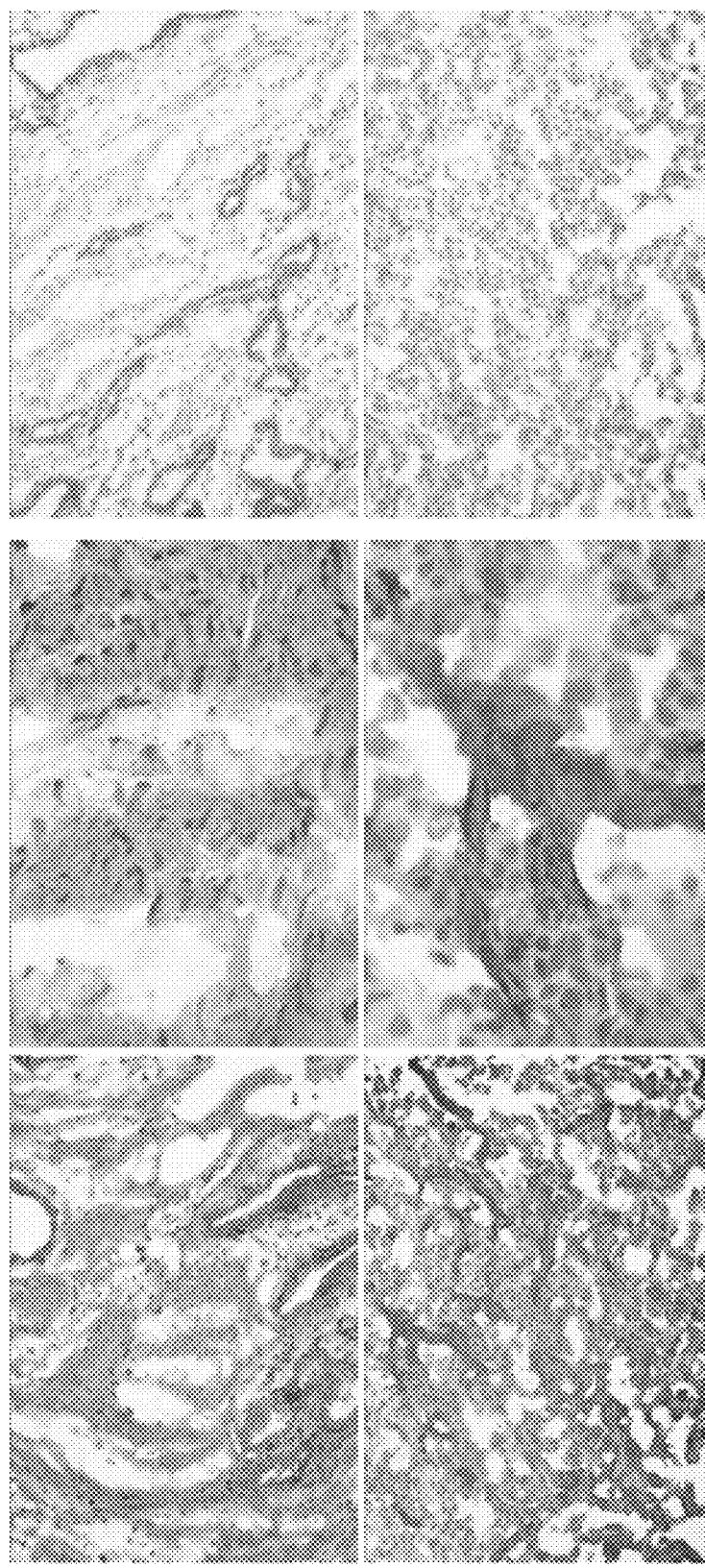
Figure 4J:
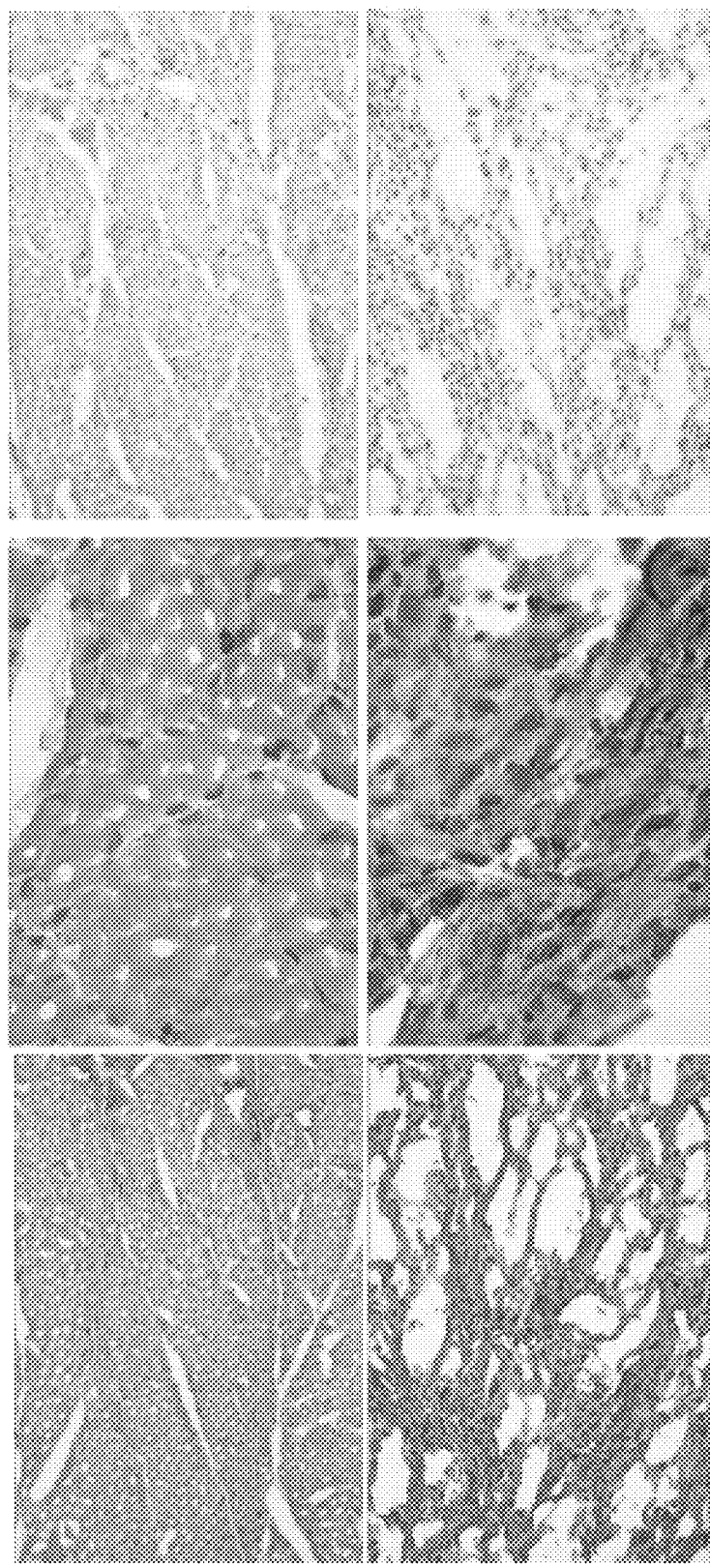
Figure 4K:
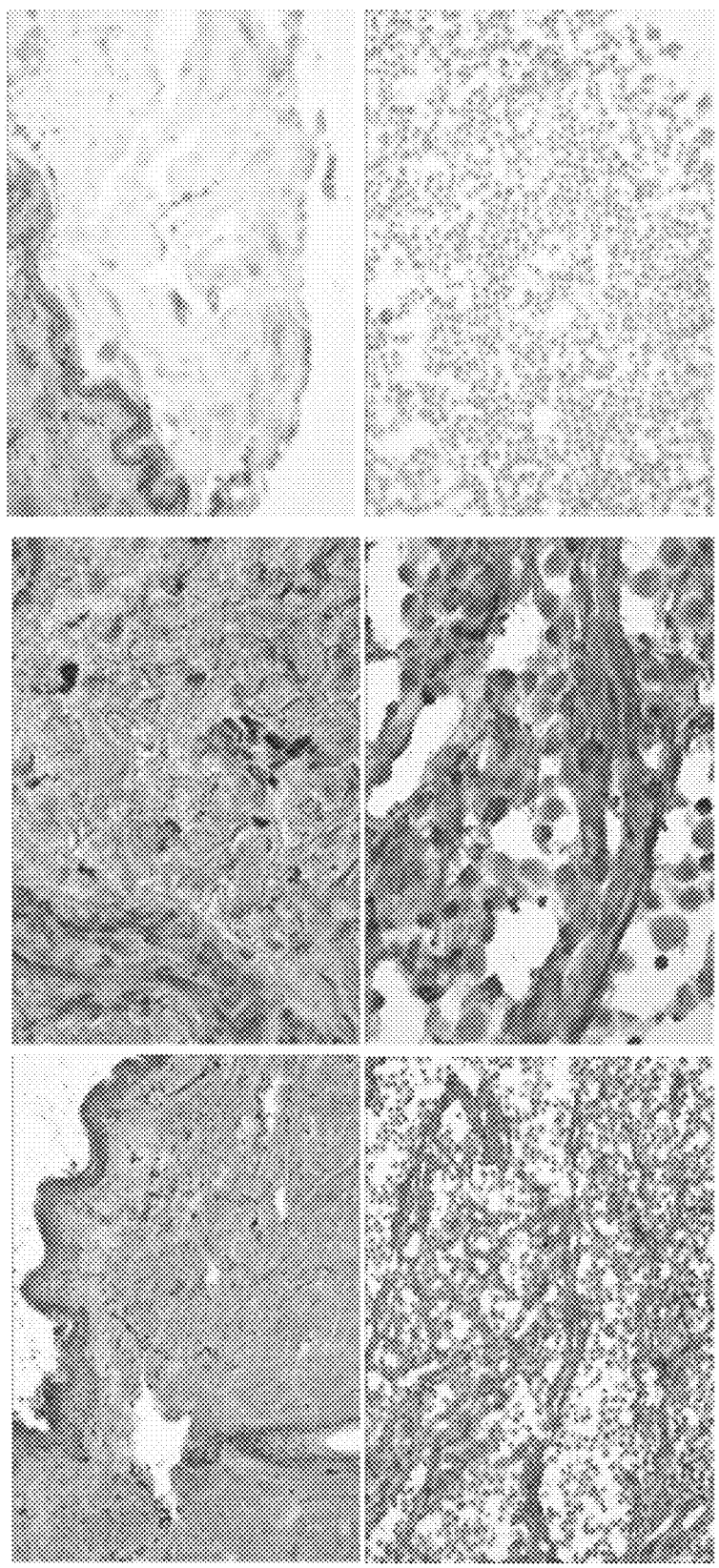
Figure 4L:
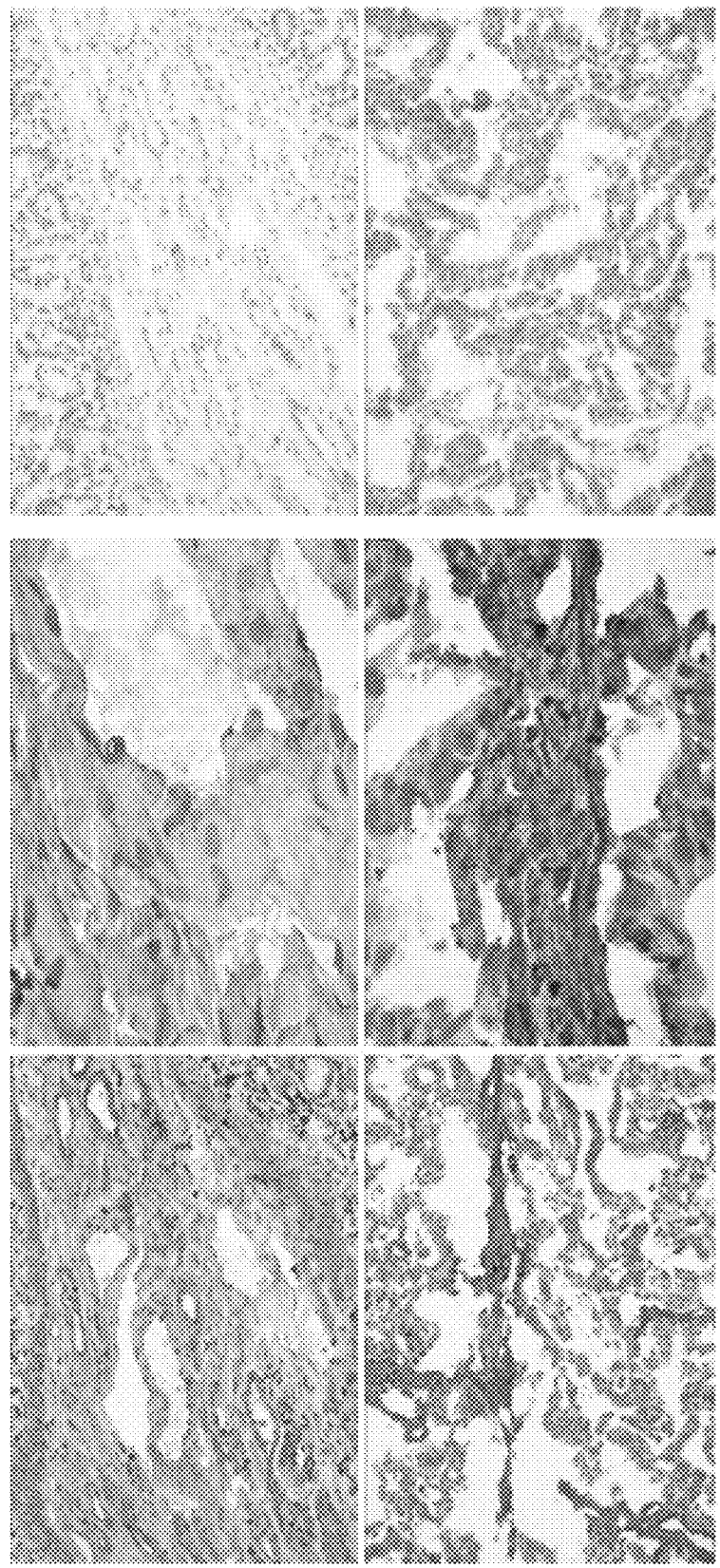
Figure 4M:
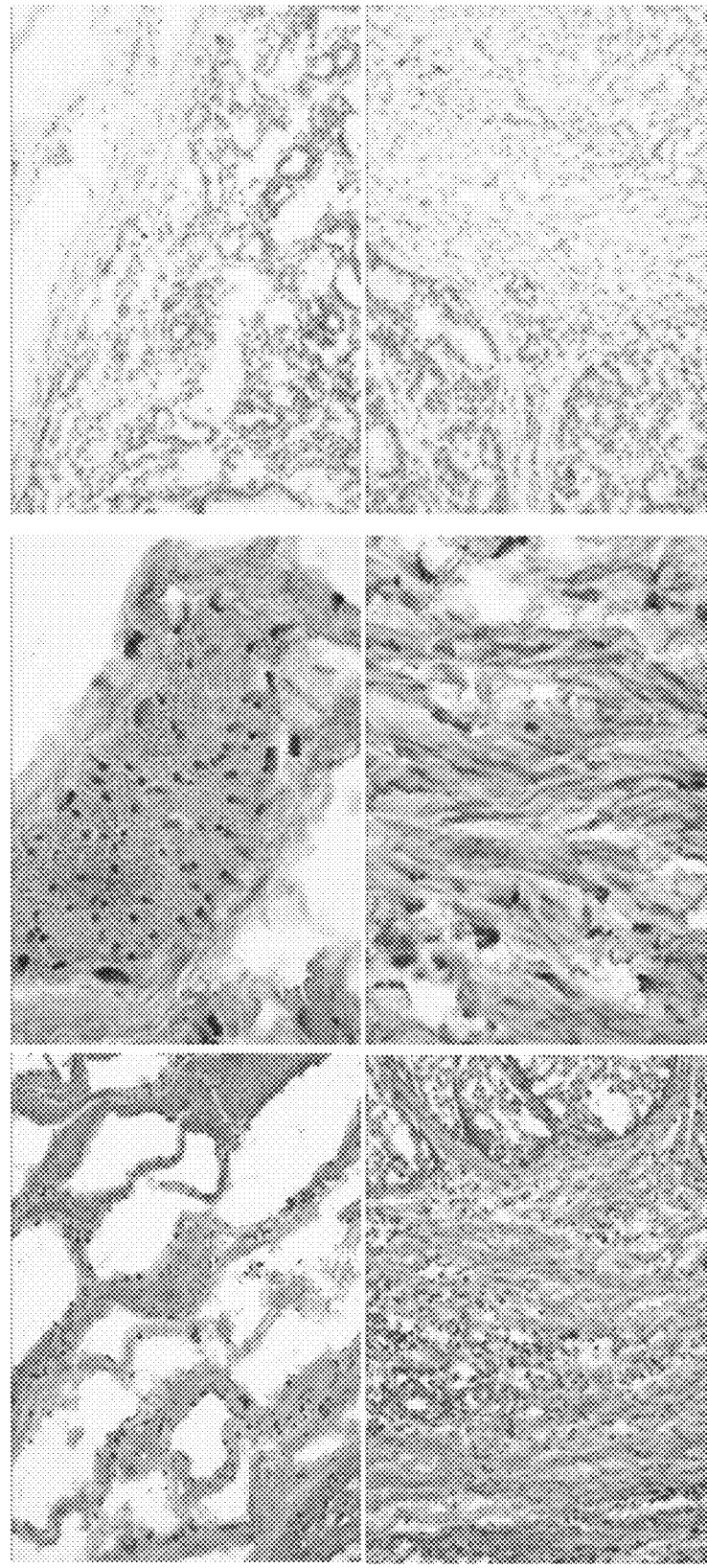
Figure 4N:
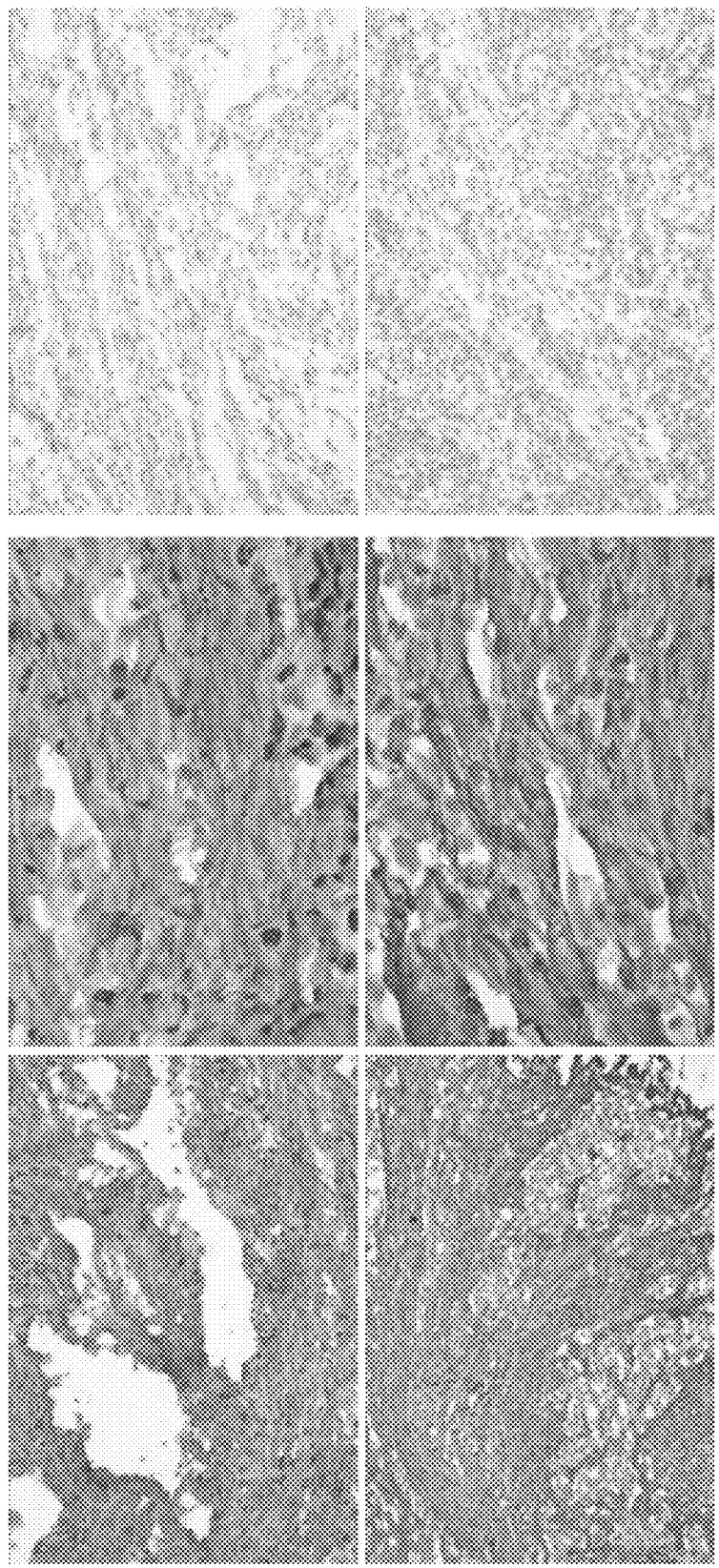

Binding of Anti-TNC A2 Antibodies on Human Tumor Tissue Versus Normal Tissue Sections In order to check the specificity of the selected 2B10 Fab for the A2 domain of human tenascin (TNC-A2), and to evaluate its capability to bind selectively to tumor tissues versus normal tissues, immunohistochemical analyses were performed. Briefly, the 2B10 variable region in a Fab fragment was fused to a FLAG fragment (SHD2B10-FLAG). Healthy and cancerous human uterine tissue samples were prepared for immunohistochemical staining Subsequently, the samples were incubated with the SHD2B10-FLAG Fab fragment. The samples were then washed and incubated with a fluorescent antibody specific for the FLAG epitope. Cancerous tissue samples exhibited higher expression levels of TNC A2 as compared to the healthy tissue samples (FIG. 3A). Various human tissue samples from healthy individuals and cancer patients were incubated with the SHD2B10-FLAG Fab fragment as described. FIG. 3B gives the quantified expression levels of TNC A2 in various human tissue samples in terms of % of immunofluorescence surface area. In a another set of experiments the 2B10 variable region was used in a mouse IgG format. Healthy and cancerous human tissue samples from different organs were prepared for immunohistochemical staining Subsequently, the samples were incubated with the SHD2B10-mouse IgG. The samples were then washed and incubated with a peroxidase developing system. FIG. 4 A-N shows that cancerous tissue samples exhibited higher expression levels of TNC A2 as compared to the healthy tissue samples.

Example 9

Binding of Anti-TNC A2 Antibodies to Tenascin-C on U87 MG Glioblastoma Cells

Figure 5:
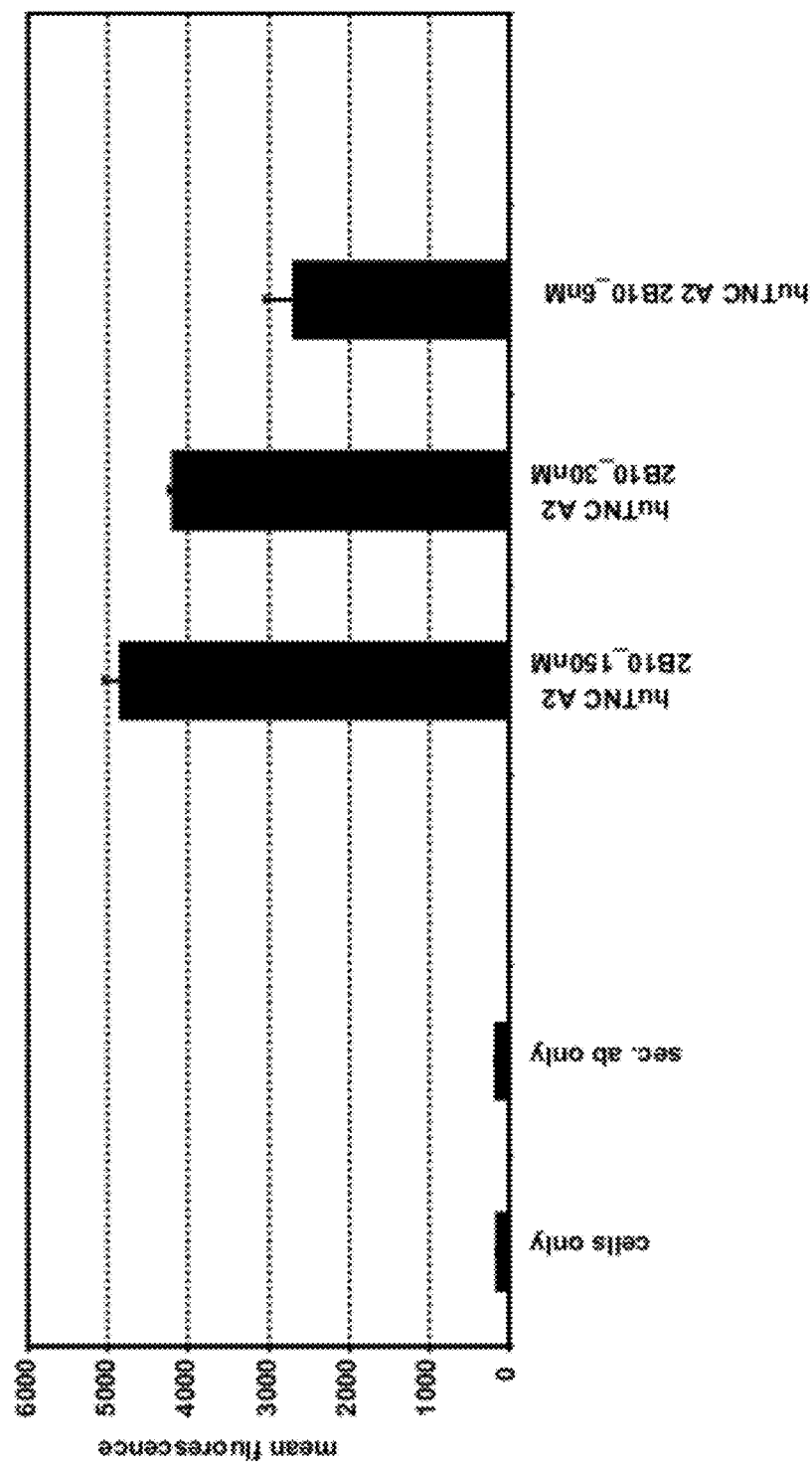
FIG. 5 shows binding of 2B10-derived human IgG to TNC A2 expressed on U87MG glioblastoma tumor cells as determined by flow cytometry (see Example 9). Mean fluorescence intensity of cells treated with different concentrations of 2B10 IgG compared to untreated cells and cells stained only with the secondary antibody (negative controls) is shown.

The 2B10 Fab was converted to a human IgG1 antibody and tested for binding to TNC A2 expressed on U87MG glioblastoma tumor cells by FACS. Briefly, 200.000 cells per well were incubated with the indicated concentration of the anti-TNC A2 antibody 2B10 in a round bottom 96-well plate, incubated for 30 min at 4° C. and washed once with PBS/ 0.1% BSA. Bound antibody was detected with FITC-conjugated AffiniPure F(ab')2 Fragment goat anti-human IgG Fcγ Specific (Jackson Immuno Research Lab #109-096-098, working solution: 1:20 diluted in PBS/0.1% BSA, freshly prepared) after incubation for 30 min at 4° C., using a FACS Cantoll (Software FACS Diva). FIG. 5 shows the mean fluorescence intensity of binding in a dose-dependent manner compared to untreated cells and cells stained only with the secondary antibody.

Figure 8:
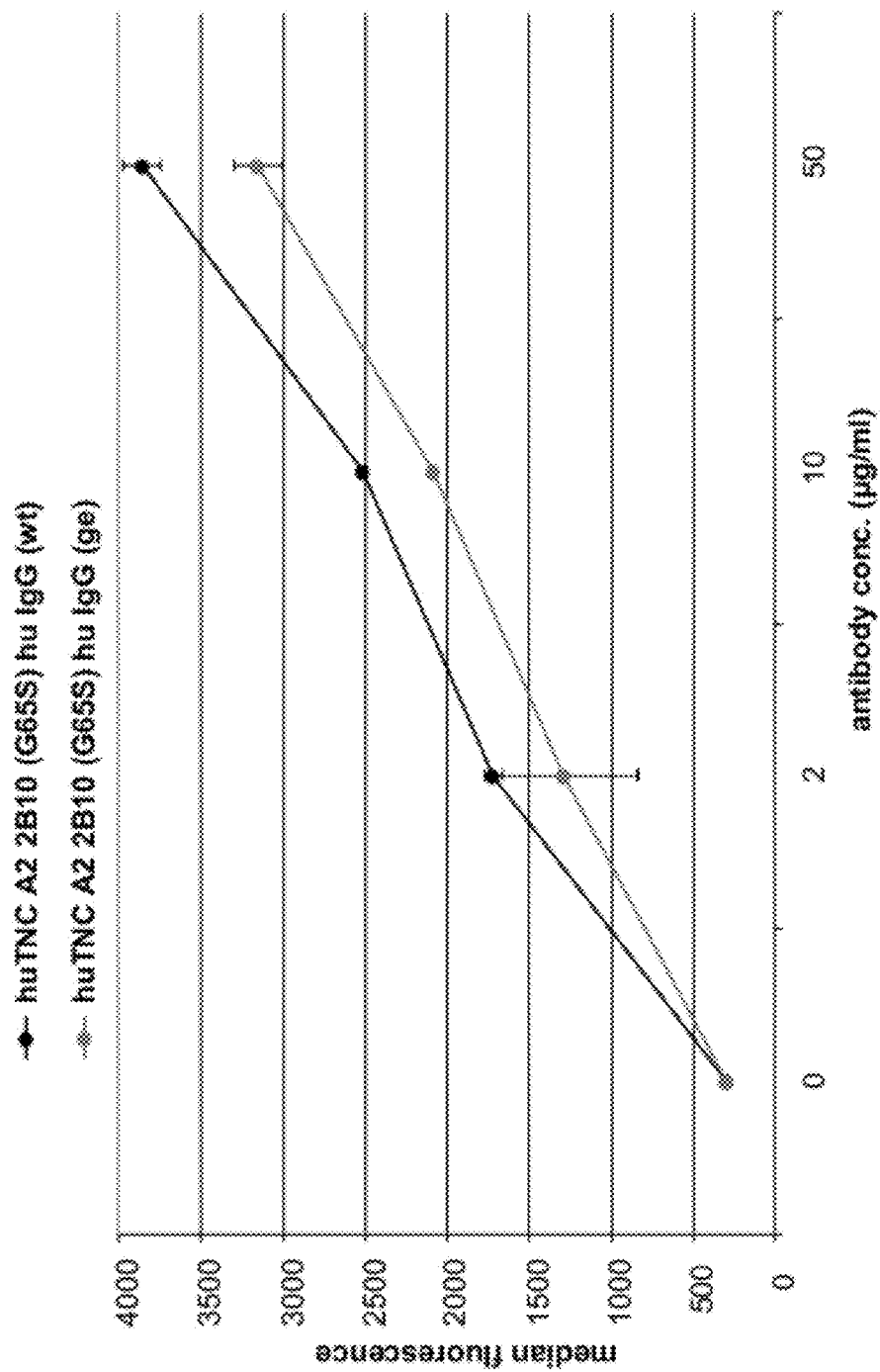
FIG. 8 shows binding of anti-TNC A2 antibody 2B10 as wildtype (wt) and glycoengineered (ge) version to TNC A2 on U87MG cells.

Using the same experimental procedure, the glycoengineered 2B10 human IgG antibody was tested for binding to TNC A2 on U87MG cells, compared to the wild-type 2B10 human IgG antibody. FIG. 8 shows that both the wild-type and the glycoengineered 2B10 antibody bind to TNC A2 on U87MG cells.

Example 10

Binding of Affinity Matured Anti-TNC A2 Antibodies to Tenascin-C on Tumor Cells

Binding of human IgG1 antibodies derived from affinity matured 2B10 Fabs to human TNC A2 on U87MG glioblastoma cells or SK-Mel5 melanoma cells is measured by FACS. Briefly, 200.000 cells per well are incubated with the indicated concentration of the 2B10 derived anti-TNC A2 antibodies in a round bottom 96-well-plate, incubated for 30 min at 4° C. and washed once with PBS/0.1% BSA. Bound antibody is detected with FITC-conjugated AffiniPure F(ab')2 Fragment goat anti-human IgG Fcγ Specific (Jackson Immuno Research Lab #109-096-098, working solution: 1:20 diluted in PBS/0.1% BSA, freshly prepared) after incubation for 30 min at 4° C. using a FACS CantoII (Software FACS Diva).

Example 11

Antibody-Dependent Cell-Mediated Cytotoxicity Mediated by Glycoengineered Anti-TNC A2 IgG1 Antibodies Human IgG1 antibodies against TNC A2 derived from 2B10 are glycoengineered by co-transfection with plasmids encoding for GnTIII and ManII as described in Example 1.

Subsequently, glycoengineered 2B10 parental and affinity matured human IgG1 antibodies derived from 2B10 are compared in an ADCC assay for their potential to mediate superior antibody mediated cellular cytotoxicity compared to their non-glycoengineered wildtype version. Briefly, U87MG glioblastoma cells or SK-Mel5 melanoma cells as target cells are collected, washed and resuspended in culture medium and stained with freshly prepared Calcein AM (Molecular Probes) at 37° C. for 30 min, washed three times, counted and diluted to 300,000 cells/ml. This suspension is transferred to a round bottom 96-well plate (30,000 cells/well), the respective antibody dilution is added and incubated for 10 min to facilitate the binding of the tested antibody to the cells prior to contact with effector cells. Effector to target ratio is 30 to 1 for PBMCs; alternatively NK92 cells can be applied. Co-incubation is performed for 4 hours. As read-out the release of lactate dehydrogenase (LDH) into supernatant after disintegration of the attacked cells is used. LDH from co-culture supernatant is collected and analyzed with a LDH detection Kit (Roche Applied Science). Substrate conversion by the LDH enzyme is measured with an ELISA absorbance reader (SoftMaxPro software, reference wavelengths: 490 nm versus 650 nm).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that specifically binds to the A2 domain of tenascin C (TNC A2), wherein the antibody comprises three heavy chain complementarity determining regions (HCDRs) HCDR1, HCDR2, HCDR3 and three light chain CDRs (LCDRs) LCDR1, LCDR2, LCDR3, having the amino acid sequences as follows:
   (a) a heavy chain CDR1 of SEQ ID NO: 3;
   (b) a heavy chain CDR2 of SEQ ID NO: 9;
   (c) a heavy chain CDR3 of SEQ ID NO: 27;
   (d) a light chain CDR1 of SEQ ID NO: 29;
   (e) a light chain CDR2 of SEQ ID NO: 35 and
   (f) a light chain CDR3 of SEQ ID NO:47
wherein said antibody comprises a glycoengineered IgG Fc region, wherein said antibody has an increased proportion of non-fucosylated oligosaccharides in said Fc region, as compared to a non-glycoengineered antibody.

2. The antibody of claim 1, which is a monoclonal antibody.

3. The antibody of claim 1, which is a human, a humanized, or a chimeric antibody.

4. The antibody of claim 1, wherein said antibody binds to human TNC A2 with a KD value lower than about 1 μM.

5. The antibody of claim 1, wherein the antibody comprises a heavy chain variable region (VH) and a light chain variable region (VL), wherein said VH has an amino acid sequence having at least 95% sequence identity to the amino acid sequence of SEQ ID NO: 59 and wherein said VL has an amino acid sequence having at least 95% sequence identity to the amino acid sequence of SEQ ID NO:57.

6. The antibody of claim 1, wherein said antibody has increased ADCC effector function and/or increased Fc receptor binding affinity as compared to a non-glycoengineered antibody.

7. An immunoconjugate comprising the antibody of claim 1 and a cytotoxic agent.

8. A pharmaceutical formulation comprising the antibody of claim 1 and a pharmaceutically acceptable carrier.

9. An isolated antibody that specifically binds to the A2 domain of Tenascin-C (TNC A2), wherein the antibody comprises three heavy chain complementarity determining regions (HCDRs) HCDR1, HCDR2, HCDR3 and three light chain CDRs (LCDRs) LCDR1, LCDR2, LCDR3 comprising the combination of the heavy chain CDR1 (HCDR1) of SEQ ID NO: 3 the heavy chain CDR2 (HCDR2) of SEQ ID NO: 9, and the heavy chain CDR3 (HCDR3) of SEQ ID NO: 27, and the light chain CDR1 (LCDR1) of SEQ ID NO: 29, the light chain CDR2 (LCDR2) of SEQ ID NO: 35, and the light chain CDR3 (LCDR3) of SEQ ID NO:47, wherein said antibody is a full length IgG class antibody having a human constant region comprising a glycoengineered Fc region having an increased proportion of non-fucosylated oligosaccharides in said Fc region, as compared to a non-glycoengineered antibody.

10. The antibody of claim 9, wherein said antibody has increased ADCC effector function and/or increased Fc receptor binding affinity as compared to a non-glycoengineered antibody.

11. An immunoconjugate comprising the antibody of claim 9 and a cytotoxic agent.

12. A pharmaceutical formulation comprising the antibody of claim 9 and a pharmaceutically acceptable carrier.

13. The antibody of claim 9, wherein the antibody comprises a heavy chain variable region (VH) and a light chain variable region (VL), wherein said VH has an amino acid sequence having at least 95% sequence identity to the amino acid sequence of SEQ ID NO: 59.

14. The antibody of claim 13, wherein said VL has an amino acid sequence having at least 95% sequence identity to the amino acid sequence of SEQ ID NO: 57.

15. The antibody of claim 13, wherein said VH has the amino acid sequence of SEQ ID NO: 59.

16. The antibody of claim 15, wherein said VL has the amino acid sequence of SEQ ID NO:57.

17. The antibody of claim 1, wherein said Fc region is a human Fc region.

18. The antibody of claim 1, wherein said Fc region is an IgG1 Fc region.

* * * * *

```
                          SEQUENCE LISTING

<160> NUMBER OF SEQ ID NOS: 136

<210> SEQ ID NO 1
<211> LENGTH: 1611
<212> TYPE: DNA
<213> ORGANISM: Artificial Sequence
<220> FEATURE:
<223> OTHER INFORMATION: Library Template for DP47-3 library

<400> SEQUENCE: 1
atgaaatacc tattgcctac ggcagccgct ggattgttat tactcgcggc ccagccggcc      60
atggccgaaa tcgtgttaac gcagtctcca ggcaccctgt ctttgtctcc aggggaaaga     120
gccaccctct cttgcagggc cagtcagagt gttagcagca gctacttagc ctggtaccag     180
cagaaacctg gccaggctcc caggctcctc atctatggag catccagcag ggccactggc     240
atcccagaca ggttcagtgg cagtggatcc gggacagact tcactctcac catcagcaga     300
ctggagcctg aagattttgc agtgtattac tgtcagcagt atggtagctc accgctgacg     360
ttcggccagg ggaccaaagt ggaaatcaaa cgtacggtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg tggagccgca     720
gaacaaaaac tcatctcaga agaggatctg aatggagccg cagactacaa ggacgacgac     780
gacaagggtg ccgcataata aggcgcgcca attctatttc aaggagacag tcatatgaaa     840
tacctgctgc cgaccgctgc tgctggtctg ctgctcctcg ctgcccagcc ggcgatggcc     900
gaggtgcaat gctggagtc tgggggaggc ttggtacagc ctggggggtc cctgagactc     960
tcctgtgcag cctccggatt caccttagc agttatgcca tgagctgggt ccgccaggct    1020
ccagggaagg gctggagtg gtctcagct attagtggta gtgtggtag cacatactac    1080 gcagactccg tgaagggccg gttcaccatc tccagagaca attccaagaa cacgctgtat    1140
ctgcagatga acagcctgag agccgaggac acggccgtat attactgtgc gaaaccgttt    1200
ccgtattttg actactgggg ccaaggaacc ctggtcaccg tctcgagtgc tagcaccaaa    1260
ggcccatcgg tcttccccct ggcaccctcc tccaagagca cctctggggg cacagcggcc    1320
ctgggctgcc tggtcaagga ctacttcccc gaaccggtga cggtgtcgtg gaactcaggc    1380
gccctgacca gcggcgtgca caccttcccg gctgtcctac agtcctcagg actctactcc    1440
```

| ctcagcagcg tggtgaccgt gccctccagc agcttgggca cccagaccta catctgcaac | 1500 |
| gtgaatcaca agcccagcaa caccaaagtg acaagaaag ttgagcccaa atcttgtgac | 1560 |
| gcggccgcaa gcactagtgc ccatcaccat caccatcacg ccgcggcata g | 1611 |

```
<210> SEQ ID NO 2
<211> LENGTH: 1617
<212> TYPE: DNA
<213> ORGANISM: Artificial Sequence
<220> FEATURE:
<223> OTHER INFORMATION: Library Template for DP88-3 library

<400> SEQUENCE: 2
```

| atgaaatacc tattgcctac ggcagccgct ggattgttat tactcgcggc ccagccggcc | 60 |
| atggccgata tccagatgac ccagtctcca tcctccctgt ctgcatctgt cggagaccgg | 120 |
| gtcaccatca cctgccgggc aagtcagggc attagaaatg atttaggctg gtaccagcag | 180 |
| aagccaggga agcccctaa gcgcctgatc tatgctgcat ccagtttgca gagtggcgtc | 240 |
| ccatcaaggt tcagcggcag tggatccggg acagagttca ctctcaccat cagcagcttg | 300 |
| cagcctgaag attttgccac ctattactgc ttgcagcata atagttaccc cacgtttggc | 360 |
| cagggcacca aagtcgagat caagcgtacg gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca aagcagacta cgagaaacac aaagtctacg cctgcgaagt cacccatcag | 660 |
| ggcctgagct cgcccgtcac aaagagcttc aacaggggag agtgtggagc cgcagaacaa | 720 |
| aaactcatct cagaagagga tctgaatgga gccgcagact acaaggacga cgacgacaag | 780 |
| ggtgccgcat aataaggcgc gccaattcta tttcaaggag acagtcatat gaaatacctg | 840 |
| ctgccgaccc tgctgctggg tctgctgctc tcgctgcccc agccggcgat ggcccaggtg | 900 |
| caattggtgc agtctggggc tgaggtgaag aagcctgggt cctcggtgaa ggtctcctgc | 960 |
| aaggcctccg gaggcacatt cagcagctac gctataagct gggtgcgaca ggcccctgga | 1020 |
| caagggctcg agtggatggg agggatcatc ctatctttg gtacagcaaa ctacgcacag | 1080 |
| aagttccagg gcagggtcac cattactgca gacaaatcca cgagcacagc ctacatggag | 1140 |
| ctgagcagcc tgagatctga ggacaccgcc gtgtattact gtgcgagact atccccaggc | 1200 |
| ggttactatg ttatggatgc ctggggccaa gggaccaccg tgaccgtctc ctcagctagc | 1260 |
| accaaaggcc catcggtctt ccccctggca ccctcctcca agagcacctc tgggggcaca | 1320 |
| gcggccctgg gctgcctggt caaggactac ttccccgaac cggtgacggt gtcgtggaac | 1380 |
| tcaggcgccc tgaccagcgg cgtgcacacc ttcccggctg tcctacagtc ctcaggactc | 1440 |
| tactccctca gcagcgtggt gaccgtgccc tccagcagct gggcaccca gacctacatc | 1500 |
| tgcaacgtga atcacaagcc cagcaacacc aaagtggaca gaaagttga gcccaaatct | 1560 |
| tgtgacgcgg ccgcaagcac tagtgcccat caccatcacc atcacgccgc ggcatag | 1617 |

```
<210> SEQ ID NO 3
<211> LENGTH: 5
<212> TYPE: PRT
<213> ORGANISM: Artificial Sequence
<220> FEATURE:
<223> OTHER INFORMATION: HCDR1 Kabat

<400> SEQUENCE: 3
```

Ser Tyr Ala Ile Ser
1               5

<210> SEQ ID NO 4
<211> LENGTH: 15
<212> TYPE: DNA
<213> ORGANISM: Artificial Sequence
<220> FEATURE:
<223> OTHER INFORMATION: HCDR1 Kabat (DNA 1)

<400> SEQUENCE: 4
agctacgcta taagc                                                    15

<210> SEQ ID NO 5
<211> LENGTH: 7
<212> TYPE: PRT
<213> ORGANISM: Artificial Sequence
<220> FEATURE:
<223> OTHER INFORMATION: HCDR1 Chothia

<400> SEQUENCE: 5

Gly Gly Thr Phe Ser Ser Tyr
1               5

<210> SEQ ID NO 6
<211> LENGTH: 21
<212> TYPE: DNA
<213> ORGANISM: Artificial Sequence
<220> FEATURE:
<223> OTHER INFORMATION: HCDR1 Chothia (DNA1)

<400> SEQUENCE: 6
ggaggcacat tcagcagcta c                                             21

<210> SEQ ID NO 7
<211> LENGTH: 10
<212> TYPE: PRT
<213> ORGANISM: Artificial Sequence
<220> FEATURE:
<223> OTHER INFORMATION: HCDR1 AbM

<400> SEQUENCE: 7

Gly Gly Thr Phe Ser Ser Tyr Ala Ile Ser
1               5                   10

<210> SEQ ID NO 8
<211> LENGTH: 30
<212> TYPE: DNA
<213> ORGANISM: Artificial Sequence
<220> FEATURE:
<223> OTHER INFORMATION: HCDR1 AbM (DNA1)

<400> SEQUENCE: 8
ggaggcacat tcagcagcta cgctataagc                                    30

<210> SEQ ID NO 9
<211> LENGTH: 16
<212> TYPE: PRT
<213> ORGANISM: Artificial Sequence
<220> FEATURE:
<223> OTHER INFORMATION: HCDR2 Kabat (1)

<400> SEQUENCE: 9

Gly Ile Ile Pro Ile Phe Gly Thr Ala Asn Tyr Ala Gln Lys Phe Gln
1               5                   10                  15

```
<210> SEQ ID NO 10
<211> LENGTH: 48
<212> TYPE: DNA
<213> ORGANISM: Artificial Sequence
<220> FEATURE:
<223> OTHER INFORMATION: HCDR2 Kabat (1) (DNA)

<400> SEQUENCE: 10
gggatcatcc ctatctttgg tacagcaaac tacgcacaga agttccag            48

<210> SEQ ID NO 11
<211> LENGTH: 16
<212> TYPE: PRT
<213> ORGANISM: Artificial Sequence
<220> FEATURE:
<223> OTHER INFORMATION: HCDR2 Kabat (2)

<400> SEQUENCE: 11

Ala Ile Ile Pro Ile Leu Gly Ile Ala Asn Tyr Ala Gln Lys Phe Gln
1               5                   10                  15

<210> SEQ ID NO 12
<211> LENGTH: 48
<212> TYPE: DNA
<213> ORGANISM: Artificial Sequence
<220> FEATURE:
<223> OTHER INFORMATION: HCDR2 Kabat (2) (DNA)

<400> SEQUENCE: 12
gctatcatcc cgatccttgg tatcgcaaac tacgcacaga agttccag            48

<210> SEQ ID NO 13
<211> LENGTH: 16
<212> TYPE: PRT
<213> ORGANISM: Artificial Sequence
<220> FEATURE:
<223> OTHER INFORMATION: HCDR2 Kabat (3)

<400> SEQUENCE: 13

Val Ile Ile Pro Ile Leu Gly Thr Ala Asn Tyr Ala Gln Lys Phe Gln
1               5                   10                  15

<210> SEQ ID NO 14
<211> LENGTH: 48
<212> TYPE: DNA
<213> ORGANISM: Artificial Sequence
<220> FEATURE:
<223> OTHER INFORMATION: HCDR2 Kabat (3) (DNA)

<400> SEQUENCE: 14
gtgatcatcc ctatccttgg taccgcaaac tacgcacaga agttccag            48

<210> SEQ ID NO 15
<211> LENGTH: 8
<212> TYPE: PRT
<213> ORGANISM: Artificial Sequence
<220> FEATURE:
<223> OTHER INFORMATION: HCDR2 Chothia (1)

<400> SEQUENCE: 15

Ile Pro Ile Phe Gly Thr Ala Asn
1               5

<210> SEQ ID NO 16
<211> LENGTH: 21
<212> TYPE: DNA
```

```
<213> ORGANISM: Artificial Sequence
<220> FEATURE:
<223> OTHER INFORMATION: HCDR2 Chothia (1) (DNA)

<400> SEQUENCE: 16
atccctatct tggtacagc a                                              21

<210> SEQ ID NO 17
<211> LENGTH: 8
<212> TYPE: PRT
<213> ORGANISM: Artificial Sequence
<220> FEATURE:
<223> OTHER INFORMATION: HCDR2 Chothia (2)

<400> SEQUENCE: 17

Ile Pro Ile Leu Gly Ile Ala Asn
1               5

<210> SEQ ID NO 18
<211> LENGTH: 21
<212> TYPE: DNA
<213> ORGANISM: Artificial Sequence
<220> FEATURE:
<223> OTHER INFORMATION: HCDR2 Chothia (2) (DNA)

<400> SEQUENCE: 18
atcccgatcc ttggtatcgc a                                             21

<210> SEQ ID NO 19
<211> LENGTH: 8
<212> TYPE: PRT
<213> ORGANISM: Artificial Sequence
<220> FEATURE:
<223> OTHER INFORMATION: HCDR2 Chothia (3)

<400> SEQUENCE: 19

Ile Pro Ile Leu Gly Thr Ala Asn
1               5

<210> SEQ ID NO 20
<211> LENGTH: 21
<212> TYPE: DNA
<213> ORGANISM: Artificial Sequence
<220> FEATURE:
<223> OTHER INFORMATION: HCDR2 Chothia (3) (DNA)

<400> SEQUENCE: 20
atccctatcc ttggtaccgc a                                             21

<210> SEQ ID NO 21
<211> LENGTH: 10
<212> TYPE: PRT
<213> ORGANISM: Artificial Sequence
<220> FEATURE:
<223> OTHER INFORMATION: HCDR2 AbM (1)

<400> SEQUENCE: 21

Gly Ile Ile Pro Ile Phe Gly Thr Ala Asn
1               5                   10

<210> SEQ ID NO 22
<211> LENGTH: 27
<212> TYPE: DNA
<213> ORGANISM: Artificial Sequence
<220> FEATURE:
<223> OTHER INFORMATION: HCDR2 AbM (1) (DNA)
```

<400> SEQUENCE: 22
gggatcatcc ctatctttgg tacagca         27

<210> SEQ ID NO 23
<211> LENGTH: 10
<212> TYPE: PRT
<213> ORGANISM: Artificial Sequence
<220> FEATURE:
<223> OTHER INFORMATION: HCDR2 AbM (2)

<400> SEQUENCE: 23

Ala Ile Ile Pro Ile Leu Gly Ile Ala Asn
1               5                   10

<210> SEQ ID NO 24
<211> LENGTH: 27
<212> TYPE: DNA
<213> ORGANISM: Artificial Sequence
<220> FEATURE:
<223> OTHER INFORMATION: HCDR2 AbM (2) (DNA)

<400> SEQUENCE: 24
gctatcatcc cgatccttgg tatcgca         27

<210> SEQ ID NO 25
<211> LENGTH: 10
<212> TYPE: PRT
<213> ORGANISM: Artificial Sequence
<220> FEATURE:
<223> OTHER INFORMATION: HCDR2 AbM (3)

<400> SEQUENCE: 25

Val Ile Ile Pro Ile Leu Gly Thr Ala Asn
1               5                   10

<210> SEQ ID NO 26
<211> LENGTH: 27
<212> TYPE: DNA
<213> ORGANISM: Artificial Sequence
<220> FEATURE:
<223> OTHER INFORMATION: HCDR2 AbM (3) (DNA)

<400> SEQUENCE: 26
gtgatcatcc ctatccttgg taccgca         27

<210> SEQ ID NO 27
<211> LENGTH: 8
<212> TYPE: PRT
<213> ORGANISM: Artificial Sequence
<220> FEATURE:
<223> OTHER INFORMATION: HCDR3

<400> SEQUENCE: 27

Tyr Cys Ala Arg Leu Tyr Gly Tyr
1               5

<210> SEQ ID NO 28
<211> LENGTH: 24
<212> TYPE: DNA
<213> ORGANISM: Artificial Sequence
<220> FEATURE:
<223> OTHER INFORMATION: HCDR3 (DNA)

<400> SEQUENCE: 28
tactgtgcga gactgtacgg ttac            24

```
<210> SEQ ID NO 29
<211> LENGTH: 11
<212> TYPE: PRT
<213> ORGANISM: Artificial Sequence
<220> FEATURE:
<223> OTHER INFORMATION: LCDR1 (1)

<400> SEQUENCE: 29

Arg Ala Ser Gln Gly Ile Arg Asn Asp Leu Gly
1               5                   10

<210> SEQ ID NO 30
<211> LENGTH: 33
<212> TYPE: DNA
<213> ORGANISM: Artificial Sequence
<220> FEATURE:
<223> OTHER INFORMATION: LCDR1 (1) (DNA 1)

<400> SEQUENCE: 30
cgggcaagtc agggcattag aaatgattta ggc                                   33

<210> SEQ ID NO 31
<211> LENGTH: 11
<212> TYPE: PRT
<213> ORGANISM: Artificial Sequence
<220> FEATURE:
<223> OTHER INFORMATION: LCDR1 (2)

<400> SEQUENCE: 31

Arg Ala Ser Gln Gly Ile Arg Asn Val Leu Gly
1               5                   10

<210> SEQ ID NO 32
<211> LENGTH: 33
<212> TYPE: DNA
<213> ORGANISM: Artificial Sequence
<220> FEATURE:
<223> OTHER INFORMATION: LCDR1 (2) (DNA 1)

<400> SEQUENCE: 32
cgggcaagtc agggcattcg taatgtttta ggc                                   33

<210> SEQ ID NO 33
<211> LENGTH: 11
<212> TYPE: PRT
<213> ORGANISM: Artificial Sequence
<220> FEATURE:
<223> OTHER INFORMATION: LCDR1 (3)

<400> SEQUENCE: 33

Arg Ala Ser Gln Ser Ile Arg Asn Val Leu Gly
1               5                   10

<210> SEQ ID NO 34
<211> LENGTH: 33
<212> TYPE: DNA
<213> ORGANISM: Artificial Sequence
<220> FEATURE:
<223> OTHER INFORMATION: LCDR1 (3) (DNA)

<400> SEQUENCE: 34
cgggcaagtc agagcattcg taatgtttta ggc                                   33

<210> SEQ ID NO 35
<211> LENGTH: 7
<212> TYPE: PRT
```

```
<213> ORGANISM: Artificial Sequence
<220> FEATURE:
<223> OTHER INFORMATION: LCDR2 (1)

<400> SEQUENCE: 35

Ala Ala Ser Ser Leu Gln Ser
1               5

<210> SEQ ID NO 36
<211> LENGTH: 21
<212> TYPE: DNA
<213> ORGANISM: Artificial Sequence
<220> FEATURE:
<223> OTHER INFORMATION: LCDR2 (1) (DNA)

<400> SEQUENCE: 36
gctgcatcca gtttgcagag t                                                   21

<210> SEQ ID NO 37
<211> LENGTH: 7
<212> TYPE: PRT
<213> ORGANISM: Artificial Sequence
<220> FEATURE:
<223> OTHER INFORMATION: LCDR2 (2)

<400> SEQUENCE: 37

Asp Ser Ser Ser Leu Gln Ser
1               5

<210> SEQ ID NO 38
<211> LENGTH: 21
<212> TYPE: DNA
<213> ORGANISM: Artificial Sequence
<220> FEATURE:
<223> OTHER INFORMATION: LCDR2 (2) (DNA)

<400> SEQUENCE: 38
gattcgtcca gtttgcagag t                                                   21

<210> SEQ ID NO 39
<211> LENGTH: 7
<212> TYPE: PRT
<213> ORGANISM: Artificial Sequence
<220> FEATURE:
<223> OTHER INFORMATION: LCDR2 (3)

<400> SEQUENCE: 39

Asp Ala Tyr Ser Leu Gln Ser
1               5

<210> SEQ ID NO 40
<211> LENGTH: 21
<212> TYPE: DNA
<213> ORGANISM: Artificial Sequence
<220> FEATURE:
<223> OTHER INFORMATION: LCDR2 (3) (DNA)

<400> SEQUENCE: 40
gatgcttaca gcttgcagag t                                                   21

<210> SEQ ID NO 41
<211> LENGTH: 7
<212> TYPE: PRT
<213> ORGANISM: Artificial Sequence
<220> FEATURE:
<223> OTHER INFORMATION: LCDR2 (4)
```

```
<400> SEQUENCE: 41

Asp Val Ser Ser Leu Gln Ser
1               5

<210> SEQ ID NO 42
<211> LENGTH: 21
<212> TYPE: DNA
<213> ORGANISM: Artificial Sequence
<220> FEATURE:
<223> OTHER INFORMATION: LCDR2 (4) (DNA)

<400> SEQUENCE: 42
gatgtgtcca gtttgcagag t                                        21

<210> SEQ ID NO 43
<211> LENGTH: 7
<212> TYPE: PRT
<213> ORGANISM: Artificial Sequence
<220> FEATURE:
<223> OTHER INFORMATION: LCDR2 (5)

<400> SEQUENCE: 43

Asp Ala Ser Ser Leu Gln Ser
1               5

<210> SEQ ID NO 44
<211> LENGTH: 21
<212> TYPE: DNA
<213> ORGANISM: Artificial Sequence
<220> FEATURE:
<223> OTHER INFORMATION: LCDR2 (5) (DNA)

<400> SEQUENCE: 44
gatgcgtcca gtttgcagag t                                        21

<210> SEQ ID NO 45
<211> LENGTH: 7
<212> TYPE: PRT
<213> ORGANISM: Artificial Sequence
<220> FEATURE:
<223> OTHER INFORMATION: LCDR2 (6)

<400> SEQUENCE: 45

Ala Ala Thr Ser Leu Gln Ser
1               5

<210> SEQ ID NO 46
<211> LENGTH: 21
<212> TYPE: DNA
<213> ORGANISM: Artificial Sequence
<220> FEATURE:
<223> OTHER INFORMATION: LCDR2 (6) (DNA)

<400> SEQUENCE: 46
gctgctacca gtttgcagag t                                        21

<210> SEQ ID NO 47
<211> LENGTH: 9
<212> TYPE: PRT
<213> ORGANISM: Artificial Sequence
<220> FEATURE:
<223> OTHER INFORMATION: LCDR3

<400> SEQUENCE: 47

Leu Gln Asn Gly Leu Gln Pro Ala Thr
1               5
```

<210> SEQ ID NO 48
<211> LENGTH: 27
<212> TYPE: DNA
<213> ORGANISM: Artificial Sequence
<220> FEATURE:
<223> OTHER INFORMATION: LCDR3 (DNA 1)

<400> SEQUENCE: 48
ttgcagaatg gtctgcagcc cgcgacg                                27

<210> SEQ ID NO 49
<211> LENGTH: 15
<212> TYPE: DNA
<213> ORGANISM: Artificial Sequence
<220> FEATURE:
<223> OTHER INFORMATION: HCDR1 Kabat (DNA 2)

<400> SEQUENCE: 49
agctatgcta taagc                                             15

<210> SEQ ID NO 50
<211> LENGTH: 21
<212> TYPE: DNA
<213> ORGANISM: Artificial Sequence
<220> FEATURE:
<223> OTHER INFORMATION: HCDR1 Chothia (DNA 2)

<400> SEQUENCE: 50
ggaggcacat tcagcagcta t                                      21

<210> SEQ ID NO 51
<211> LENGTH: 30
<212> TYPE: DNA
<213> ORGANISM: Artificial Sequence
<220> FEATURE:
<223> OTHER INFORMATION: HCDR1 AbM (DNA 2)

<400> SEQUENCE: 51
ggaggcacat tcagcagcta tgctataagc                             30

<210> SEQ ID NO 52
<211> LENGTH: 33
<212> TYPE: DNA
<213> ORGANISM: Artificial Sequence
<220> FEATURE:
<223> OTHER INFORMATION: LCDR1 (1) (DNA 2)

<400> SEQUENCE: 52
cgggcaagtc agggcattcg taatgattta ggc                         33

<210> SEQ ID NO 53
<211> LENGTH: 33
<212> TYPE: DNA
<213> ORGANISM: Artificial Sequence
<220> FEATURE:
<223> OTHER INFORMATION: LCDR1 (2) (DNA 2)

<400> SEQUENCE: 53
cgggcaagtc agggcattcg taatgtttta ggc                         33

<210> SEQ ID NO 54
<211> LENGTH: 27
<212> TYPE: DNA
<213> ORGANISM: Artificial Sequence
<220> FEATURE:

<223> OTHER INFORMATION: LCDR3 (DNA 2)

<400> SEQUENCE: 54
ctgcagaatg gtctgcagcc cgcgacg                27

<210> SEQ ID NO 55
<211> LENGTH: 107
<212> TYPE: PRT
<213> ORGANISM: Artificial Sequence
<220> FEATURE:
<223> OTHER INFORMATION: 2B10; VL

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 56
<211> LENGTH: 321
<212> TYPE: DNA
<213> ORGANISM: Artificial Sequence
<220> FEATURE:
<223> OTHER INFORMATION: 2B10; VL

<400> SEQUENCE: 56

```
gatatccaga tgacccagtc tccatcctcc ctgtctgcat ctgtcggaga ccgggtcacc    60
atcacctgcc gggcaagtca gggcattaga aatgatttag ctggtacca gcagaagcca   120 gggaaagccc ctaagcgcct gatctatgct gcatccagtt tgcagagtgg cgtcccatca   180
aggttcagcg gcggtggatc cgggacagag ttcactctca ccatcagcag cttgcagcct   240
gaagattttg ccacctatta ctgcttgcag aatggtctgc agcccgcgac gtttggccag   300
ggcaccaaag tcgagatcaa g                                            321
```

<210> SEQ ID NO 57
<211> LENGTH: 107
<212> TYPE: PRT
<213> ORGANISM: Artificial Sequence
<220> FEATURE:
<223> OTHER INFORMATION: 2B10(GS); VL

<400> SEQUENCE: 57

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
```

```
                        50                  55                  60
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Asn Gly Leu Gln Pro Ala
                 85                  90                  95

Thr Phe Gly Gln Gly Thr Lys Val Glu Ile Lys
            100                 105

<210> SEQ ID NO 58
<211> LENGTH: 321
<212> TYPE: DNA
<213> ORGANISM: Artificial Sequence
<220> FEATURE:
<223> OTHER INFORMATION: 2B10(GS); VL

<400> SEQUENCE: 58
gatatccaga tgacccagtc tccatcctcc ctgtctgcat ctgtcggaga ccgggtcacc    60
atcacctgcc gggcaagtca gggcattaga aatgatttag ctggtaccag cagaagcca    120 gggaaagccc ctaagcgcct gatctatgct gcatccagtt tgcagagtgg cgtcccatca   180
aggttcagcg gcagtggatc cgggacagag ttcactctca ccatcagcag cttgcagcct   240
gaagattttg ccacctatta ctgcttgcag aatggtctgc agcccgcgac gtttggccag   300
ggcaccaaag tcgagatcaa g                                             321

<210> SEQ ID NO 59
<211> LENGTH: 121
<212> TYPE: PRT
<213> ORGANISM: Artificial Sequence
<220> FEATURE:
<223> OTHER INFORMATION: 2B10; VH

<400> SEQUENCE: 59

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 60
<211> LENGTH: 363
<212> TYPE: DNA
<213> ORGANISM: Artificial Sequence
<220> FEATURE:
<223> OTHER INFORMATION: 2B10; VH

<400> SEQUENCE: 60
caggtgcaat tggtgcagtc tggggctgag gtgaagaagc ctgggtcctc ggtgaaggtc    60
```

```
tcctgcaagg cctccggagg cacattcagc agctacgcta taagctgggt gcgacaggcc    120
cctggacaag ggctcgagtg gatgggaggg atcatcccta tctttggtac agcaaactac    180
gcacagaagt tccagggcag ggtcaccatt actgcagaca atccacgag cacagcctac    240 atggagctga gcagcctgag atctgaggac accgccgtgt attactgtgc gagactgtac    300
ggttacgctt actacggtgc ttttgactac tggggccaag gaccaccgt gaccgtctcc    360 tca                                                                 363
```

```
<210> SEQ ID NO 61
<211> LENGTH: 107
<212> TYPE: PRT
<213> ORGANISM: Artificial Sequence
<220> FEATURE:
<223> OTHER INFORMATION: 2B10_C3B6; VL

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

```
<210> SEQ ID NO 62
<211> LENGTH: 321
<212> TYPE: DNA
<213> ORGANISM: Artificial Sequence
<220> FEATURE:
<223> OTHER INFORMATION: 2B10_C3B6; VL

<400> SEQUENCE: 62
gatatccaga tgacccagtc tccatcctcc ctgtctgcat ctgtcggaga ccgggtcacc     60
atcacctgcc gggcaagtca gggcattaga aatgatttag ctggtacca gcagaagcca    120 gggaaagccc ctaagcgcct gatctatgct gcatccagtt tgcagagtgg cgtcccatca    180
aggttcagcg gcagtggatc cgggacagag ttcactctca ccatcagcag cttgcagcct    240
gaagattttg ccacctatta ctgcttgcag aatggtctgc agcccgcgac gtttggccag    300
ggcaccaaag tcgagatcaa g                                              321
```

```
<210> SEQ ID NO 63
<211> LENGTH: 121
<212> TYPE: PRT
<213> ORGANISM: Artificial Sequence
<220> FEATURE:
<223> OTHER INFORMATION: 2B10_C3B6; VH

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                    20                  25                  30
Ala Ile Ser Trp Val Arg Gln Ala Pro Gly Gln Gly Leu Glu Trp Met
            35                  40                  45

Gly Ala Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 64
<211> LENGTH: 363
<212> TYPE: DNA
<213> ORGANISM: Artificial Sequence
<220> FEATURE:
<223> OTHER INFORMATION: 2B10_C3B6; VH

<400> SEQUENCE: 64
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag ggctcgagtg gatgggagct atcatcccga tccttggtat cgcaaactac     180
gcacagaagt tccagggcag ggtcaccatt actgcagaca aatccacgag cacagcctac     240
atggagctga gcagcctgag atctgaggac accgccgtgt attactgtgc gagactgtac     300
ggttacgctt actacggtgc ttttgactac tggggccaag gaccaccgt gaccgtctcc      360 tca                                                                   363

<210> SEQ ID NO 65
<211> LENGTH: 107
<212> TYPE: PRT
<213> ORGANISM: Artificial Sequence
<220> FEATURE:
<223> OTHER INFORMATION: 2B10_6A12; VL

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 66
<211> LENGTH: 321
<212> TYPE: DNA
```

-continued

<213> ORGANISM: Artificial Sequence
<220> FEATURE:
<223> OTHER INFORMATION: 2B10_6A12; VL

<400> SEQUENCE: 66

```
gatatccaga tgacccagtc tccatcctcc ctgtctgcat ctgtcggaga ccgggtcacc    60
atcacctgcc gggcaagtca gggcattaga aatgatttag ctggtacca gcagaagcca   120
gggaaagccc ctaagcgcct gatctatgct gcatccagtt tgcagagtgg cgtcccatca   180
aggttcagcg gcagtggatc cgggacagag ttcactctca ccatcagcag cttgcagcct   240
gaagattttg ccacctatta ctgcttgcag aatggtctgc agcccgcgac gtttggccag   300
ggcaccaaag tcgagatcaa g                                              321
```

<210> SEQ ID NO 67
<211> LENGTH: 121
<212> TYPE: PRT
<213> ORGANISM: Artificial Sequence
<220> FEATURE:
<223> OTHER INFORMATION: 2B10_6A12; VH

<400> SEQUENCE: 67

```
Gln Val Gln Leu Val Gln Ser Gly Ala Glu Val Lys Lys Pro Gly Ser
 1               5                  10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Val Ile Ile Pro Ile Leu Gly Thr Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Leu Tyr Gly Tyr Ala Tyr Tyr Gly Ala Phe Asp Tyr Trp Gly
            100                 105                 110
Gln Gly Thr Thr Val Thr Val Ser Ser
        115                 120
```

<210> SEQ ID NO 68
<211> LENGTH: 363
<212> TYPE: DNA
<213> ORGANISM: Artificial Sequence
<220> FEATURE:
<223> OTHER INFORMATION: 2B10_6A12; VH

<400> SEQUENCE: 68

```
caggtgcaat tggtgcagtc tggggctgag gtgaagaagc ctgggtcctc ggtgaaggtc    60
tcctgcaagg cctccggagg cacattcagc agctatgcta taagctgggt gcgacaggcc   120
cctggacaag gctcgagtg gatgggagtg atcatccta tccttggtac cgcaaactac    180
gcacagaagt tccagggcag ggtcaccatt actgcagaca atccacgag cacagcctac   240
atggagctga gcagcctgag atctgaggac accgccgtgt attactgtgc gagactgtac   300
ggttacgctt actacggtgc ttttgactac tggggccaag gaccaccgt gaccgtctcc   360
tca                                                                  363
```

<210> SEQ ID NO 69
<211> LENGTH: 107

```
<212> TYPE: PRT
<213> ORGANISM: Artificial Sequence
<220> FEATURE:
<223> OTHER INFORMATION: 2B10_C3A6; VL

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Tyr Asp Ser Ser Ser Leu Gln Ser Gly Val Pro Ser Arg Phe Ser Gly
50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 70
<211> LENGTH: 321
<212> TYPE: DNA
<213> ORGANISM: Artificial Sequence
<220> FEATURE:
<223> OTHER INFORMATION: 2B10_C3A6; VL

<400> SEQUENCE: 70
gacatccaga tgacccagtc tccttcctcc ctgtctgcat ctgtcggaga ccgggtcacc      60
atcacctgcc gggcaagtca gggcattcgt aatgttttag ctggtaccca gcagaagcca    120
gggaaagccc ctaagcgcct gatctatgat tcgtccagtt tgcagagtgg cgtcccatca    180
aggttcagcg gcggtggatc cgggacagag ttcactctca ccatcagcag cttgcagcct    240
gaagattttg ccacctatta ctgcttgcag aatggtctgc agcccgcgac gtttggccag    300
ggcaccaaag tcgagatcaa g                                              321

<210> SEQ ID NO 71
<211> LENGTH: 121
<212> TYPE: PRT
<213> ORGANISM: Artificial Sequence
<220> FEATURE:
<223> OTHER INFORMATION: 2B10_C3A6; VH

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
```

100                 105                 110
Gln Gly Thr Thr Val Thr Val Ser Ser
        115                 120

<210> SEQ ID NO 72
<211> LENGTH: 363
<212> TYPE: DNA
<213> ORGANISM: Artificial Sequence
<220> FEATURE:
<223> OTHER INFORMATION: 2B10_C3A6; VH

<400> SEQUENCE: 72
caggtgcaat tggtgcagtc tggggctgag gtgaagaagc ctgggtcctc ggtgaaggtc     60
tcctgcaagg cctccggagg cacattcagc agctacgcta taagctgggt gcgacaggcc    120
cctggacaag gctcgagtg gatgggaggg atcatcccta tctttggtac agcaaactac    180
gcacagaagt tccagggcag ggtcaccatt actgcagaca atccacgag cacagcctac    240 atggagctga gcagcctgag atctgaggac accgccgtgt attactgtgc gagactgtac    300
ggttacgctt actacggtgc ttttgactac tggggccaag gaccaccgt gaccgtctcc    360 tca                                                                 363

<210> SEQ ID NO 73
<211> LENGTH: 107
<212> TYPE: PRT
<213> ORGANISM: Artificial Sequence
<220> FEATURE:
<223> OTHER INFORMATION: 2B10_D1A2_wt; VL

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Tyr Asp Ala Tyr Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 74
<211> LENGTH: 321
<212> TYPE: DNA
<213> ORGANISM: Artificial Sequence
<220> FEATURE:
<223> OTHER INFORMATION: 2B10_D1A2_wt; VL

<400> SEQUENCE: 74
gatatccaga tgacccagtc tccatcctcc ctgtctgcat ctgtcggaga ccgggtcacc     60
atcacctgcc gggcaagtca ggggattcgt aatgttttag ctggtaccag cagaagcca    120 gggaaagccc ctaagcgcct gatctatgat gcttacagct tgcagagtgg cgtcccatca    180
aggttcagcg gcgtggatc cgggacagag ttcactctca ccatcagcag cttgcagcct    240
gaagattttg ccacctatta ctgcttgcag aatggtctgc agcccgcgac gtttggccag    300

```
ggcaccaaag tcgagatcaa g                                           321
```

<210> SEQ ID NO 75
<211> LENGTH: 121
<212> TYPE: PRT
<213> ORGANISM: Artificial Sequence
<220> FEATURE:
<223> OTHER INFORMATION: 2B10_D1A2_wt; VH

<400> SEQUENCE: 75

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

<210> SEQ ID NO 76
<211> LENGTH: 363
<212> TYPE: DNA
<213> ORGANISM: Artificial Sequence
<220> FEATURE:
<223> OTHER INFORMATION: 2B10_D1A2_wt; VH

<400> SEQUENCE: 76

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag gctcgagtg gatgggaggg atcatccta tctttggtac agcaaactac    180
gcacagaagt tccagggcag ggtcaccatt actgcagaca aatccacgag cacagcctac   240
atggagctga gcagcctgag atctgaggac accgccgtgt attactgtgc gagactgtac   300
ggttacgctt actacggtgc ttttgactac tggggccaag gaccaccgt gaccgtctcc    360 tca                                                                 363
```

<210> SEQ ID NO 77
<211> LENGTH: 107
<212> TYPE: PRT
<213> ORGANISM: Artificial Sequence
<220> FEATURE:
<223> OTHER INFORMATION: 2B10_D1A2_VD; VL

<400> SEQUENCE: 77

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45
```

Tyr Asp Ala Tyr Ser Leu Gln Ser Gly Val Pro Ser Arg Phe Ser Gly
            50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 78
<211> LENGTH: 321
<212> TYPE: DNA
<213> ORGANISM: Artificial Sequence
<220> FEATURE:
<223> OTHER INFORMATION: 2B10_D1A2_VD; VL

<400> SEQUENCE: 78
gacatccaga tgacccagtc tccatcctcc ctgtctgcat ctgtcggaga ccgggtcacc      60
atcacctgcc gggcaagtca ggggattcgt aatgatttag ctggtaccag cagaaagcca     120
gggaaagccc ctaagcgcct gatctatgat gcttacagct tgcagagtgg cgtcccatca     180
aggttcagcg gcggtggatc cgggacagag ttcactctca ccatcagcag cttgcagcct     240
gaagattttg ccacctatta ctgcttgcag aatggtctgc agcccgcgac gtttggccag     300
ggcaccaaag tcgagatcaa g                                               321

<210> SEQ ID NO 79
<211> LENGTH: 121
<212> TYPE: PRT
<213> ORGANISM: Artificial Sequence
<220> FEATURE:
<223> OTHER INFORMATION: 2B10_D1A2_VD; VH

<400> SEQUENCE: 79

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120

<210> SEQ ID NO 80
<211> LENGTH: 363
<212> TYPE: DNA
<213> ORGANISM: Artificial Sequence
<220> FEATURE:
<223> OTHER INFORMATION: 2B10_D1A2_VD; VH

<400> SEQUENCE: 80

```
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag ggctcgagtg gatgggaggg atcatcccta tctttggtac agcaaactac     180
gcacagaagt tccagggcag ggtcaccatt actgcagaca atccacgag cacagcctac      240 atggagctga gcagcctgag atctgaggac accgccgtgt attactgtgc gagactgtac     300
ggttacgctt actacggtgc ttttgactac tggggccaag gaccaccgt gaccgtctcc      360 tca                                                                   363
```

<210> SEQ ID NO 81
<211> LENGTH: 107
<212> TYPE: PRT
<213> ORGANISM: Artificial Sequence
<220> FEATURE:
<223> OTHER INFORMATION: 2B10_O7D8; VL

<400> SEQUENCE: 81

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Val
            20                  25                  30

Leu Gly Trp Tyr Gln Gln Lys Pro Gly Lys Ala Pro Lys Arg Leu Ile
        35                  40                  45

Tyr Asp Val Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 82
<211> LENGTH: 321
<212> TYPE: DNA
<213> ORGANISM: Artificial Sequence
<220> FEATURE:
<223> OTHER INFORMATION: 2B10_O7D8; VL

<400> SEQUENCE: 82

```
gatatccaga tgacccagtc tccatcctcc ctgtctgcat ctgtcggaga ccgggtcacc      60
atcacctgcc gggcaagtca gagcattcgt aatgttttag ctggtacca gcagaagcca     120 gggaaagccc ctaagcgcct gatctatgat gtgtccagtt tgcagagtgg cgtcccatca     180
aggttcagcg gcggtggatc cgggacagag ttcactctca ccatcagcag cttgcagcct     240
gaagattttg ccacctatta ctgcttgcag aatggtctgc agcccgcgac gtttggccag     300
ggcaccaaag tcgagatcaa g                                               321
```

<210> SEQ ID NO 83
<211> LENGTH: 121
<212> TYPE: PRT
<213> ORGANISM: Artificial Sequence
<220> FEATURE:
<223> OTHER INFORMATION: 2B10_O7D8; VH

<400> SEQUENCE: 83

```
Gln Val Gln Leu Val Gln Ser Gly Ala Glu Val Lys Lys Pro Gly Ser
1               5                   10                  15
```

Ser Val Lys Val Ser Cys Lys Ala Ser Gly Gly Thr Phe Ser Ser Tyr
        20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Gly Ala Phe Asp Tyr Trp Gly
            100                 105                 110

Gln Gly Thr Thr Val Thr Val Ser Ser
        115                 120

<210> SEQ ID NO 84
<211> LENGTH: 363
<212> TYPE: DNA
<213> ORGANISM: Artificial Sequence
<220> FEATURE:
<223> OTHER INFORMATION: 2B10_O7D8; VH

<400> SEQUENCE: 84
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag ggctcgagtg gatgggaggg atcatcccta tctttggtac agcaaactac   180
gcacagaagt tccagggcag ggtcaccatt actgcagaca atccacgag cacagcctac    240 atggagctga gcagcctgag atctgaggac accgccgtgt attactgtgc gagactgtac   300
ggttacgctt actacggtgc ttttgactac tggggccaag gaccaccgt gaccgtctcc    360 tca    363

<210> SEQ ID NO 85
<211> LENGTH: 107
<212> TYPE: PRT
<213> ORGANISM: Artificial Sequence
<220> FEATURE:
<223> OTHER INFORMATION: 2B10_O1F7; VL

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Tyr Asp Ala Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105

<210> SEQ ID NO 86

<211> LENGTH: 321
<212> TYPE: DNA
<213> ORGANISM: Artificial Sequence
<220> FEATURE:
<223> OTHER INFORMATION: 2B10_O1F7; VL

<400> SEQUENCE: 86

```
gatatccaga tgacccagtc tccatcctcc ctgtctgcat ctgtcggaga ccgggtcacc    60
atcacctgcc gggcaagtca gggcattcgt aatgttttag ctggtacca gcagaagcca   120
gggaaagccc ctaagcgcct gatctatgat gcgtccagtt tgcagagtgg cgtcccatca   180
aggttcagcg gcggtggatc cgggacagag ttcactctca ccatcagcag cttgcagcct   240
gaagattttg ccacctatta ctgcctgcag aatggtctgc agcccgcgac gtttggccag   300
ggcaccaaag tcgagatcaa g                                             321
```

<210> SEQ ID NO 87
<211> LENGTH: 121
<212> TYPE: PRT
<213> ORGANISM: Artificial Sequence
<220> FEATURE:
<223> OTHER INFORMATION: 2B10_O1F7; VH

<400> SEQUENCE: 87

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

<210> SEQ ID NO 88
<211> LENGTH: 363
<212> TYPE: DNA
<213> ORGANISM: Artificial Sequence
<220> FEATURE:
<223> OTHER INFORMATION: 2B10_O1F7; VH

<400> SEQUENCE: 88

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag gctcgagtg gatgggaggg atcatcccta tctttggtac agcaaactac   180
gcacagaagt tccagggcag ggtcaccatt actgcagaca atccacgag cacagcctac   240
atggagctga gcagcctgag atctgaggac accgccgtgt attactgtgc gagactgtac   300
ggttacgctt actacggtgc ttttgactac tggggccaag gaccaccgt gaccgtctcc   360
tca                                                                 363
```

-continued

<210> SEQ ID NO 89
<211> LENGTH: 107
<212> TYPE: PRT
<213> ORGANISM: Artificial Sequence
<220> FEATURE:
<223> OTHER INFORMATION: 2B10_6H10; VL

<400> SEQUENCE: 89

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Gln Ala Ala Thr Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 90
<211> LENGTH: 321
<212> TYPE: DNA
<213> ORGANISM: Artificial Sequence
<220> FEATURE:
<223> OTHER INFORMATION: 2B10_6H10; VL

<400> SEQUENCE: 90

```
gacatccaga tgacccagtc tccatcctcc ctgtctgcat ctgtcggaga ccgggtcacc    60
atcacctgcc gggcaagtca gggcattcgt aatgttttag ctggtaccag cagaagcca   120 gggaaagccc ctaagcgcct gatccaggct gctaccagtt tgcagagtgg cgtcccatca   180
aggttcagcg gcggtggatc cgggacagag ttcactctca ccatcagcag cttgcagcct   240
gaagattttg ccacctatta ctgcttgcag aatggtctgc agcccgcgac gtttggccag   300
ggcaccaaag tcgagatcaa g                                             321
```

<210> SEQ ID NO 91
<211> LENGTH: 121
<212> TYPE: PRT
<213> ORGANISM: Artificial Sequence
<220> FEATURE:
<223> OTHER INFORMATION: 2B10_6H10; VH

<400> SEQUENCE: 91

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
            115                 120

<210> SEQ ID NO 92
<211> LENGTH: 363
<212> TYPE: DNA
<213> ORGANISM: Artificial Sequence
<220> FEATURE:
<223> OTHER INFORMATION: 2B10_6H10; VH

<400> SEQUENCE: 92
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag gctcgagtg gatgggaggg atcatccta tctttggtac agcaaactac    180
gcacagaagt tccagggcag ggtcaccatt actgcagaca atccacgag cacagcctac    240 atggagctga gcagcctgag atctgaggac accgccgtgt attactgtgc gagactgtac    300
ggttacgctt actacggtgc ttttgactac tggggccaag gaccaccgt gaccgtctcc    360 tca    363

<210> SEQ ID NO 93
<211> LENGTH: 330
<212> TYPE: PRT
<213> ORGANISM: Homo sapiens

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly

```
            210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 94
<211> LENGTH: 990
<212> TYPE: DNA
<213> ORGANISM: Homo sapiens

<400> SEQUENCE: 94

```
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                      990
```

<210> SEQ ID NO 95
<211> LENGTH: 107
<212> TYPE: PRT
<213> ORGANISM: Homo sapiens

<400> SEQUENCE: 95

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 96
<211> LENGTH: 321
<212> TYPE: DNA
<213> ORGANISM: Homo sapiens

<400> SEQUENCE: 96

```
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                                321
```

<210> SEQ ID NO 97
<211> LENGTH: 119
<212> TYPE: PRT
<213> ORGANISM: Artificial Sequence
<220> FEATURE:
<223> OTHER INFORMATION: Human TNC-A2 avi-tag his6-tag

<400> SEQUENCE: 97

```
Ala Ser Thr Gly Glu Thr Pro Asn Leu Gly Glu Val Val Val Ala Glu
 1               5                  10                  15

Val Gly Trp Asp Ala Leu Lys Leu Asn Trp Thr Ala Pro Glu Gly Ala
            20                  25                  30

Tyr Glu Tyr Phe Phe Ile Gln Val Gln Glu Ala Asp Thr Val Glu Ala
            35                  40                  45

Ala Gln Asn Leu Thr Val Pro Gly Gly Leu Arg Ser Thr Asp Leu Pro
 50                  55                  60

Gly Leu Lys Ala Ala Thr His Tyr Thr Ile Thr Ile Arg Gly Val Thr
 65                  70                  75                  80

Gln Asp Phe Ser Thr Thr Pro Leu Ser Val Glu Val Leu Thr Ala Ser
                 85                  90                  95

Gly Leu Asn Asp Ile Phe Glu Ala Gln Lys Ile Glu Trp His Glu Gly
            100                 105                 110

Thr His His His His His His
            115
```

<210> SEQ ID NO 98
<211> LENGTH: 357
<212> TYPE: DNA
<213> ORGANISM: Artificial Sequence
<220> FEATURE:
<223> OTHER INFORMATION: Human TNC-A2 avi-tag his6-tag

<400> SEQUENCE: 98

```
gcgtccaccg gggaaacccc gaacctgggc gaagtggtgg tggcggaagt gggttgggat      60
gcgctgaaac tgaactggac cgcgccggaa ggcgcgtatg aatattttt catccaggtg       120 caggaagcgg ataccgttga agcggcgcag aacctgaccg ttccgggcgg tctgcgtagc      180
accgatctgc cgggcctgaa agcggcgacc cattatacca ttaccatccg tggggtgacc      240
caggatttta gcaccacccc gctgtctgtg gaagtgctga ccgctagcgg cctgaacgac      300
atcttcgagg ctcagaaaat cgaatggcac gaaggtaccc atcaccatca ccaccac        357
```

<210> SEQ ID NO 99
<211> LENGTH: 670
<212> TYPE: PRT
<213> ORGANISM: Artificial Sequence
<220> FEATURE:
<223> OTHER INFORMATION: TNC Fn5 huA1A2 huA3 avi his biotin from
      E. coli = pETR7477

<400> SEQUENCE: 99

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300
```

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
            325                 330                 335

Thr Ser Tyr Val Leu Arg Gly Leu Glu Pro Gly Gln Glu Tyr Asn Val
        340                 345                 350

Leu Leu Thr Ala Glu Lys Gly Arg His Lys Ser Lys Pro Ala Arg Val
    355                 360                 365

Lys Ala Ser Thr Glu Gln Ala Pro Glu Leu Glu Asn Leu Thr Val Thr
370                 375                 380

Glu Val Gly Trp Asp Gly Leu Arg Leu Asn Trp Thr Ala Ala Asp Gln
385                 390                 395                 400

Ala Tyr Glu His Phe Ile Ile Gln Val Gln Glu Ala Asn Lys Val Glu
                405                 410                 415

Ala Ala Arg Asn Leu Thr Val Pro Gly Ser Leu Arg Ala Val Asp Ile
            420                 425                 430

Pro Gly Leu Lys Ala Ala Thr Pro Tyr Thr Val Ser Ile Tyr Gly Val
        435                 440                 445

Ile Gln Gly Tyr Arg Thr Pro Val Leu Ser Ala Glu Ala Ser Thr Gly
450                 455                 460

Glu Thr Pro Asn Leu Gly Glu Val Val Val Ala Glu Val Gly Trp Asp
465                 470                 475                 480

Ala Leu Lys Leu Asn Trp Thr Ala Pro Glu Gly Ala Tyr Glu Tyr Phe
                485                 490                 495

Phe Ile Gln Val Gln Glu Ala Asp Thr Val Glu Ala Ala Gln Asn Leu
            500                 505                 510

Thr Val Pro Gly Gly Leu Arg Ser Thr Asp Leu Pro Gly Leu Lys Ala
        515                 520                 525

Ala Thr His Tyr Thr Ile Thr Ile Arg Gly Val Thr Gln Asp Phe Ser
530                 535                 540

Thr Thr Pro Leu Ser Val Glu Val Leu Thr Glu Glu Val Pro Asp Met
545                 550                 555                 560

Gly Asn Leu Thr Val Thr Glu Val Ser Trp Asp Ala Leu Arg Leu Asn
                565                 570                 575

Trp Thr Thr Pro Asp Gly Thr Tyr Asp Gln Phe Thr Ile Gln Val Gln
            580                 585                 590

Glu Ala Asp Gln Val Glu Glu Ala His Asn Leu Thr Val Pro Gly Ser
        595                 600                 605

Leu Arg Ser Met Glu Ile Pro Gly Leu Arg Ala Gly Thr Pro Tyr Thr
610                 615                 620

Val Thr Leu His Gly Glu Val Arg Gly His Ser Thr Arg Pro Leu Ala
625                 630                 635                 640

Val Glu Val Val Thr Ala Ser Gly Leu Asn Asp Ile Phe Glu Ala Gln
                645                 650                 655

Lys Ile Glu Trp His Glu Gly Thr His His His His His
            660                 665                 670

<210> SEQ ID NO 100
<211> LENGTH: 2013
<212> TYPE: DNA
<213> ORGANISM: Artificial Sequence
<220> FEATURE:
<223> OTHER INFORMATION: TNC Fn5 huA1A2 huA3 avi his biotin from
      E. coli = pETR7477 (DNA)

<400> SEQUENCE: 100

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600
tggcctttgc agggctggca agccacgttt ggtggtggcg accatcctcc aaaatcggat    660
ggttcaacta gtggttctgg tcatcaccat caccatcact ccgcgggtct ggtgccacgc    720
ggtagtactg caattggtat gaaagaaacc gctgctgcta aattcgaacg ccagcacatg    780
gacagcccag atctgggtac cggtggtggc tccggtattg agggacgcgg gtccatggga    840
tatcggggat ccgagctgga caccccaag acctgcagg tgtccgagac agccgagaca    900
agcctgaccc tgctgtggaa accccctg gccaagttcg accggtacag actgaactac    960
agcctgccca ctggacagtg ggtcggcgtg cagctgcccc ggaacaccac ctcctacgtg   1020
ctgcggggcc tggaacccgg ccaggaatac aacgtcctgc tgacggccga aagggccgg   1080
cacaagagca agcccgccag agtgaaggcc agcaccgagc aggcccccga gctggaaaac   1140
ctgaccgtga ccgaagtggg ctgggacggc ctgcggctga actggaccgc ggctgaccag   1200
gcctatgagc actttatcat tcaggtgcag gaggccaaca aggtggaggc agctcggaac   1260
ctcaccgtgc tggcagcct tcgggctgtg acataccgg gcctcaaggc tgctacgcct   1320
tatacagtct ccatctatgg ggtgatccag ggctatagaa accagtgct ctctgctgag   1380
gcctccacag gcgaaacacc gaacctgggc gaagtggtgg tggcggaagt gggttgggat   1440
gcgctgaaac tgaactggac cgcgccggaa ggcgcgtatg aatatttttt catccaggtg   1500
caggaagcgg ataccgttga agcggcgcag aacctgaccg ttccgggcgg tctgcgtagc   1560
accgatctgc cgggcctgaa agcggcgacc cattatacca ttaccatccg tggggtgacc   1620
caggacttct ctaccacccc tctgagcgtg gaggtgctga ccgaggaggt acccgacatg   1680
ggcaacctga ccgtgaccga ggtgtcctgg gacgccctgc ggctgaactg gaccaccccc   1740
gacggcacct acgaccagtt cacaatccag gtgcaggaag ccgaccaggt cgaagaggcc   1800
cacaatctga cagtgccagg cagcctgcgg agcatggaaa tccccggcct gagagccggc   1860
acccctaca ccgtgaccct gcacggcgaa gtgcggggcc acagcaccag acccctggcc   1920
gtggaagtgg tcacagctag cggcctgaac gacatcttcg aggctcagaa aatcgaatgg   1980
cacgaaggta cccatcacca tcaccaccac taa                                 2013
```

<210> SEQ ID NO 101
<211> LENGTH: 670
<212> TYPE: PRT
<213> ORGANISM: Artificial Sequence
<220> FEATURE:
<223> OTHER INFORMATION: TNC Fn5 cyA1A2 huA3 avi his biotin from
E. coli = pETR7478

<400> SEQUENCE: 101

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Gln Ala Pro Glu Leu Glu Asn Leu Thr Val Thr
370                 375                 380

Glu Val Gly Trp Asp Gly Leu Arg Leu Asn Trp Thr Ala Ala Asp Gln
385                 390                 395                 400

Ala Tyr Glu His Phe Val Ile Gln Val Gln Glu Ala Asn Lys Val Glu
                405                 410                 415
```

Ala Ala Gln Asn Leu Thr Val Pro Gly Asn Leu Arg Ala Val Asp Ile
            420                 425                 430

Pro Gly Leu Lys Ala Ala Thr Pro Tyr Thr Val Ser Ile Tyr Gly Val
        435                 440                 445

Ile Gln Gly Tyr Arg Thr Pro Val Leu Ser Ala Glu Ala Ser Thr Gly
    450                 455                 460

Glu Thr Pro Asn Leu Gly Glu Val Met Val Ser Glu Val Gly Trp Asp
465                 470                 475                 480

Ala Leu Lys Leu Asn Trp Thr Val Pro Glu Gly Ala Tyr Glu Tyr Phe
                485                 490                 495

Phe Ile Gln Val Gln Glu Ala Asp Thr Val Glu Ala Ala Gln Asn His
            500                 505                 510

Thr Val Pro Gly Gly Leu Arg Ser Thr Asp Leu Pro Gly Leu Lys Ala
        515                 520                 525

Ala Thr His Tyr Thr Ile Thr Ile Arg Gly Val Thr Gln Asp Phe Ser
    530                 535                 540

Thr Thr Pro Leu Ser Val Glu Val Leu Thr Glu Glu Val Pro Asp Met
545                 550                 555                 560

Gly Asn Leu Thr Val Thr Glu Val Ser Trp Asp Ala Leu Arg Leu Asn
                565                 570                 575

Trp Thr Thr Pro Asp Gly Thr Tyr Asp Gln Phe Thr Ile Gln Val Gln
            580                 585                 590

Glu Ala Asp Gln Val Glu Glu Ala His Asn Leu Thr Val Pro Gly Ser
        595                 600                 605

Leu Arg Ser Met Glu Ile Pro Gly Leu Arg Ala Gly Thr Pro Tyr Thr
    610                 615                 620

Val Thr Leu His Gly Glu Val Arg Gly His Ser Thr Arg Pro Leu Ala
625                 630                 635                 640

Val Glu Val Val Thr Ala Ser Gly Leu Asn Asp Ile Phe Glu Ala Gln
                645                 650                 655

Lys Ile Glu Trp His Glu Gly Thr His His His His His His
            660                 665                 670

<210> SEQ ID NO 102
<211> LENGTH: 2013
<212> TYPE: DNA
<213> ORGANISM: Artificial Sequence
<220> FEATURE:
<223> OTHER INFORMATION: TNC Fn5 cyA1A2 huA3 avi his biotin from
      E. coli = pETR7478 (DNA)

<400> SEQUENCE: 102 atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atagctga caagcacaac      240 atgttgggtg ttgtccaaa agagcgtgca gagatttcaa tgcttgaagg agcggttttg     300 gatattgat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca gtgtaacccat cctgacttca tgttgtatga cgctcttgat     480
gttgttttat acatggaccc aatgtgcctg atgcgttcc caaaattagt ttgttttaaa     540
aaacgtattg aagctatccc acaaattgat aagtacttga atccagcaa gtatatagca     600

```
tggcctttgc agggctggca agccacgttt ggtggtggcg accatcctcc aaaatcggat    660
ggttcaacta gtggttctgg tcatcaccat caccatcact ccgcgggtct ggtgccacgc    720
ggtagtactg caattggtat gaaagaaacc gctgctgcta aattcgaacg ccagcacatg    780
gacagcccag atctgggtac cggtggtggc tccggtattg agggacgcgg gtccatggga    840
tatcggggat ccgagctgga caccccaag gacctgcagg tgtccgagac agccgagaca    900
agcctgaccc tgctgtggaa accccctg gccaagttcg accggtacag actgaactac    960
agcctgccca ctggacagtg ggtcggcgtg cagctgcccc ggaacaccac ctcctacgtg   1020
ctgcggggcc tggaacccgg ccaggaatac aacgtcctgc tgacggccga agggcaga    1080
cacaagagca agcccgccag agtgaaggcc agcaccgagc aggcccccga gctggaaaac   1140
ctgaccgtga ccgaagtggg ctgggacggc ctgagactga actggacagc cgccgaccag   1200
gcttatgagc acttcgtgat ccaggtgcag gaagccaaca aggtcgaggc cgcccagaat   1260
ctgaccgtgc ccggcaacct gagagccgtg acatccctg gcctgaaggc tgccaccccc   1320
tacaccgtgt ccatctacgg cgtgattcag ggctaccgga cccctgtgct gtctgccgag   1380
gccagcacag gcgagacacc caacctgggc gaagtgatgg tgtctgaagt gggatgggat   1440
gccctgaagc tcaattggac cgtgcctgag ggcgcctacg agtacttctt tattcaggtc   1500
caggaagctg acaccgtcga agccgctcag aaccacacag tgcctggcgg cctgagaagc   1560
accgatctgc ccggcctgaa agccgctaca cactacacaa tcaccatcag aggcgtgacc   1620
caggacttca gcaccacccc cctgagcgtg gaggtgctga ccgaagaggt acccgacatg   1680
ggcaacctga ccgtgaccga ggtgtcctgg gacgccctgc ggctgaactg gaccaccccc   1740
gacggcacct acgaccagtt cacaatccag gtgcaggaag ccgaccaggt cgaagaggcc   1800
cacaatctga cagtgccagg cagcctgcgg agcatggaaa tccccggcct gagagccggc   1860
acccctaca ccgtgaccct gcacggcgaa gtgcggggcc acagcaccag acccctggcc   1920
gtggaagtgg tcacagctag cggcctgaac gacatcttcg aggctcagaa aatcgaatgg   1980
cacgaaggta cccatcacca tcaccaccac taa                                 2013
```

<210> SEQ ID NO 103
<211> LENGTH: 670
<212> TYPE: PRT
<213> ORGANISM: Artificial Sequence
<220> FEATURE:
<223> OTHER INFORMATION: TNC Fn5 muA1A2 huA3 avi his biotin from
      E. coli = pETR7479

<400> SEQUENCE: 103

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser

-continued

```
                100                 105                 110
Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Gly Ser Thr Ser
            210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Ser Gly
            260                 265                 270

Ile Glu Gly Arg Gly Ser Met Gly Tyr Arg Gly Ser Glu Leu Asp Thr
            275                 280                 285

Pro Lys Asp Leu Gln Val Ser Glu Thr Ala Glu Thr Ser Leu Thr Leu
            290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
            355                 360                 365

Lys Ala Ser Thr Glu Glu Val Pro Ser Leu Glu Asn Leu Thr Val Thr
            370                 375                 380

Glu Ala Gly Trp Asp Gly Leu Arg Leu Asn Trp Thr Ala Asp Asp Leu
385                 390                 395                 400

Ala Tyr Glu Tyr Phe Val Ile Gln Val Gln Glu Ala Asn Asn Val Glu
                405                 410                 415

Thr Ala His Asn Phe Thr Val Pro Gly Asn Leu Arg Ala Ala Asp Ile
            420                 425                 430

Pro Gly Leu Lys Val Ala Thr Ser Tyr Arg Val Ser Ile Tyr Gly Val
            435                 440                 445

Ala Arg Gly Tyr Arg Thr Pro Val Leu Ser Ala Glu Thr Ser Thr Gly
450                 455                 460

Thr Thr Pro Asn Leu Gly Glu Val Thr Val Ala Glu Val Gly Trp Asp
465                 470                 475                 480

Ala Leu Thr Leu Asn Trp Thr Ala Pro Glu Gly Ala Tyr Lys Asn Phe
                485                 490                 495

Phe Ile Gln Val Leu Glu Ala Asp Thr Thr Gln Thr Val Gln Asn Leu
            500                 505                 510

Thr Val Pro Gly Gly Leu Arg Ser Val Asp Leu Pro Gly Leu Lys Ala
            515                 520                 525
```

```
Ala Thr Arg Tyr Tyr Ile Thr Leu Arg Gly Val Thr Gln Asp Phe Gly
        530                 535                 540

Thr Ala Pro Leu Ser Val Glu Val Leu Thr Glu Glu Val Pro Asp Met
545                 550                 555                 560

Gly Asn Leu Thr Val Thr Glu Val Ser Trp Asp Ala Leu Arg Leu Asn
                565                 570                 575

Trp Thr Thr Pro Asp Gly Thr Tyr Asp Gln Phe Thr Ile Gln Val Gln
                580                 585                 590

Glu Ala Asp Gln Val Glu Glu Ala His Asn Leu Thr Val Pro Gly Ser
            595                 600                 605

Leu Arg Ser Met Glu Ile Pro Gly Leu Arg Ala Gly Thr Pro Tyr Thr
        610                 615                 620

Val Thr Leu His Gly Glu Val Arg Gly His Ser Thr Arg Pro Leu Ala
625                 630                 635                 640

Val Glu Val Val Thr Ala Ser Gly Leu Asn Asp Ile Phe Glu Ala Gln
                645                 650                 655

Lys Ile Glu Trp His Glu Gly Thr His His His His His His
            660                 665                 670
```

<210> SEQ ID NO 104
<211> LENGTH: 2013
<212> TYPE: DNA
<213> ORGANISM: Artificial Sequence
<220> FEATURE:
<223> OTHER INFORMATION: TNC Fn5 muA1A2 huA3 avi his biotin from
      E. coli = pETR7479 (DNA)

<400> SEQUENCE: 104

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg ttgtcccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ggttcaacta gtggttctgg tcatcaccat caccatcact ccgcgggtct ggtgccacgc    720
ggtagtactg caattggtat gaaagaaacc gctgctgcta aattcgaacg ccagcacatg    780
gacagcccag atctgggtac cggtggtggc tccggtattg agggacgcgg gtccatggga    840
tatcggggat ccgagctgga caccccaag gacctgcagg tgtccgagac agccgagaca    900
agcctgaccc tgctgtggaa accccctg gccaagttcg accggtacag actgaactac    960
agcctgccca ctggacagtg gtcggcgtg cagctgcccc ggaacaccac ctcctacgtg   1020
ctgcggggcc tggaacccgg ccaggaatac aacgtcctgc tgacggccga agggccgg     1080 cacaagagca gcccgccag agtgaaggcc agcaccgagg aagtgcccag cctggaaaac   1140
ctgaccgtga ccgaggccgg ctgggacggc ctgcggctga ctggaccgc cgacgacctg   1200
```

```
gcctacgagt acttcgtgat ccaggtgcag gaagccaaca acgtcgagac agcccacaac   1260
ttcaccgtgc ccggcaacct gagagccgcc gacatccccg gcctgaaggt ggccacatcc   1320
taccgggtgt ccatctacgg cgtggccagg ggctaccgga ccccgtgct gtccgccgag    1380
acaagcaccg gcaccacgcc gaacctgggc gaagtgaccg tggcggaagt gggttgggat   1440
gcgctgaccc tgaattggac cgcaccggaa ggcgcgtata aaaacttttt catccaggtg   1500
ctggaagcgg ataccaccca gaccgtgcag aacctgaccg tgccgggtgg tctgcgtagc   1560
gtggatctgc cgggcctgaa agcggcgacc cgttattaca ttaccctgcg tggcgtgacc   1620
caggattttg caccgcgcc gctgtctgtg gaagtgctga ccgaggaggt acccgacatg   1680
ggcaacctga ccgtgaccga ggtgtcctgg gacgccctgc ggctgaactg gaccacccc   1740
gacggcacct acgaccagtt cacaatccag gtgcaggaag ccgaccaggt cgaagaggcc   1800
cacaatctga cagtgccagg cagcctgcgg agcatggaaa tccccggcct gagagccggc   1860
accccctaca ccgtgaccct gcacggcgaa gtgcggggcc acagcaccag acccctggcc   1920
gtggaagtgg tcacagctag cggcctgaac gacatcttcg aggctcagaa aatcgaatgg   1980
cacgaaggta cccatcacca tcaccaccac taa                                2013
```

<210> SEQ ID NO 105
<211> LENGTH: 773
<212> TYPE: PRT
<213> ORGANISM: Artificial Sequence
<220> FEATURE:
<223> OTHER INFORMATION: HEK human TNC 1-8

<400> SEQUENCE: 105

```
Met Gly Trp Ser Cys Ile Ile Leu Phe Leu Val Ala Thr Ala Thr Gly
1               5                   10                  15

Val His Ser Glu Val Ser Pro Pro Lys Asp Leu Val Val Thr Glu Val
            20                  25                  30

Thr Glu Glu Thr Val Asn Leu Ala Trp Asp Asn Glu Met Arg Val Thr
        35                  40                  45

Glu Tyr Leu Val Val Tyr Thr Pro Thr His Glu Gly Gly Leu Glu Met
    50                  55                  60

Gln Phe Arg Val Pro Gly Asp Gln Thr Ser Thr Ile Ile Arg Glu Leu
65                  70                  75                  80

Glu Pro Gly Val Glu Tyr Phe Ile Arg Val Phe Ala Ile Leu Glu Asn
                85                  90                  95

Lys Lys Ser Ile Pro Val Ser Ala Arg Val Ala Thr Tyr Leu Pro Ala
            100                 105                 110

Pro Glu Gly Leu Lys Phe Lys Ser Ile Lys Glu Thr Ser Val Glu Val
        115                 120                 125

Glu Trp Asp Pro Leu Asp Ile Ala Phe Glu Thr Trp Glu Ile Ile Phe
    130                 135                 140

Arg Asn Met Asn Lys Glu Asp Glu Gly Glu Ile Thr Lys Ser Leu Arg
145                 150                 155                 160

Arg Pro Glu Thr Ser Tyr Arg Gln Thr Gly Leu Ala Pro Gly Gln Glu
                165                 170                 175

Tyr Glu Ile Ser Leu His Ile Val Lys Asn Asn Thr Arg Gly Pro Gly
            180                 185                 190

Leu Lys Arg Val Thr Thr Thr Arg Leu Asp Ala Pro Ser Gln Ile Glu
        195                 200                 205

Val Lys Asp Val Thr Asp Thr Thr Ala Leu Ile Thr Trp Phe Lys Pro
    210                 215                 220
```

```
Leu Ala Glu Ile Asp Gly Ile Glu Leu Thr Tyr Gly Ile Lys Asp Val
225                 230                 235                 240

Pro Gly Asp Arg Thr Thr Ile Asp Leu Thr Glu Asp Glu Asn Gln Tyr
                245                 250                 255

Ser Ile Gly Asn Leu Lys Pro Asp Thr Glu Tyr Glu Val Ser Leu Ile
            260                 265                 270

Ser Arg Arg Gly Asp Met Ser Ser Asn Pro Ala Lys Glu Thr Phe Thr
        275                 280                 285

Thr Gly Leu Asp Ala Pro Arg Asn Leu Arg Arg Val Ser Gln Thr Asp
    290                 295                 300

Asn Ser Ile Thr Leu Glu Trp Arg Asn Gly Lys Ala Ala Ile Asp Ser
305                 310                 315                 320

Tyr Arg Ile Lys Tyr Ala Pro Ile Ser Gly Gly Asp His Ala Glu Val
                325                 330                 335

Asp Val Pro Lys Ser Gln Gln Ala Thr Thr Lys Thr Thr Leu Thr Gly
            340                 345                 350

Leu Arg Pro Gly Thr Glu Tyr Gly Ile Gly Val Ser Ala Val Lys Glu
        355                 360                 365

Asp Lys Glu Ser Asn Pro Ala Thr Ile Asn Ala Ala Thr Glu Leu Asp
    370                 375                 380

Thr Pro Lys Asp Leu Gln Val Ser Glu Thr Ala Glu Thr Ser Leu Thr
385                 390                 395                 400

Leu Leu Trp Lys Thr Pro Leu Ala Lys Phe Asp Arg Tyr Arg Leu Asn
                405                 410                 415

Tyr Ser Leu Pro Thr Gly Gln Trp Val Gly Val Gln Leu Pro Arg Asn
            420                 425                 430

Thr Thr Ser Tyr Val Leu Arg Gly Leu Glu Pro Gly Gln Glu Tyr Asn
        435                 440                 445

Val Leu Leu Thr Ala Glu Lys Gly Arg His Lys Ser Lys Pro Ala Arg
    450                 455                 460

Val Lys Ala Ser Thr Glu Gln Ala Ala Met Gly Ser Pro Lys Glu Val
465                 470                 475                 480

Ile Phe Ser Asp Ile Thr Glu Asn Ser Ala Thr Val Ser Trp Arg Ala
                485                 490                 495

Pro Thr Ala Gln Val Glu Ser Phe Arg Ile Thr Tyr Val Pro Ile Thr
            500                 505                 510

Gly Gly Thr Pro Ser Met Val Thr Val Asp Gly Thr Lys Thr Gln Thr
        515                 520                 525

Arg Leu Val Lys Leu Ile Pro Gly Val Glu Tyr Leu Val Ser Ile Ile
    530                 535                 540

Ala Met Lys Gly Phe Glu Glu Ser Glu Pro Val Ser Gly Ser Phe Thr
545                 550                 555                 560

Thr Ala Leu Asp Gly Pro Ser Gly Leu Val Thr Ala Asn Ile Thr Asp
                565                 570                 575

Ser Glu Ala Leu Ala Arg Trp Gln Pro Ala Ile Ala Thr Val Asp Ser
            580                 585                 590

Tyr Val Ile Ser Tyr Thr Gly Glu Lys Val Pro Glu Ile Thr Arg Thr
        595                 600                 605

Val Ser Gly Asn Thr Val Glu Tyr Ala Leu Thr Asp Leu Glu Pro Ala
    610                 615                 620

Thr Glu Tyr Thr Leu Arg Ile Phe Ala Glu Lys Gly Pro Gln Lys Ser
625                 630                 635                 640
```

```
Ser Thr Ile Thr Ala Lys Phe Thr Thr Asp Leu Asp Ser Pro Arg Asp
                645                 650                 655

Leu Thr Ala Thr Glu Val Gln Ser Glu Thr Ala Leu Leu Thr Trp Arg
            660                 665                 670

Pro Pro Arg Ala Ser Val Thr Gly Tyr Leu Leu Val Tyr Glu Ser Val
        675                 680                 685

Asp Gly Thr Val Lys Glu Val Ile Val Gly Pro Asp Thr Thr Ser Tyr
    690                 695                 700

Ser Leu Ala Asp Leu Ser Pro Ser Thr His Tyr Thr Ala Lys Ile Gln
705                 710                 715                 720

Ala Leu Asn Gly Pro Leu Arg Ser Asn Met Ile Gln Thr Ile Phe Thr
                725                 730                 735

Thr Val Asp Leu Glu Val Leu Phe Gln Gly Pro Gly Ser Gly Leu Asn
            740                 745                 750

Asp Ile Phe Glu Ala Gln Lys Ile Glu Trp His Glu Ala Arg Ala His
        755                 760                 765

His His His His His
    770

<210> SEQ ID NO 106
<211> LENGTH: 2322
<212> TYPE: DNA
<213> ORGANISM: Artificial Sequence
<220> FEATURE:
<223> OTHER INFORMATION: HEK human TNC 1-8 (DNA)

<400> SEQUENCE: 106
atgggatgga gctgtatcat cctcttcttg gtagcaacag ctaccggtgt gcattccgag    60
gtgtctcctc ccaaagacct cgttgtgaca gaagtgacgg aagagacggt caacctggcc   120
tgggacaatg agatgcgggt cacagagtac cttgtcgtgt acacgcccac ccacgagggt   180
ggtctggaaa tgcagttccg tgtgcctggg accagacgt ccaccatcat ccgggagctg   240
gagcctggtg tggagtactt tatccgtgta tttgccatcc tggagaacaa gaagagcatt   300
cctgtcagcg ccagggtggc cacgtactta cctgcacctg aaggcctgaa attcaagtcc   360
atcaaggaga catctgtgga agtggagtgg gatcctctag acattgcttt tgaaacctgg   420
gagatcatct tccggaatat gaataaagaa gatgagggag agatcaccaa agcctgagg   480 aggccagaga cctcttaccg gcaaactggt ctagctcctg gcaagagta tgagatatct   540 ctgcacatag tgaaaacaa tacccggggc cctggcctga gagggtgac caccacacgc   600 ttggatgccc ccagccagat cgaggtgaaa gatgtcacag acaccactgc cttgatcacc   660
tggttcaagc ccctggctga gatcgatggc attgagctga cctacggcat caaagacgtg   720
ccaggagacc gtaccaccat cgatctcaca gaggacgaga accagtactc catcgggaac   780
ctgaagcctg acactgagta cgaggtgtcc ctcatctccc gcagaggtga catgtcaagc   840
aacccagcca agagaccttt cacaacaggc tcgatgctcc caggaatct tcgacgtgtt   900 tcccagacag ataacagcat cacccctgga atggaggaatg gcaaggcagc tattgacagt   960
tacagaatta agtatgcccc catctctgga ggggaccacg ctgaggttga tgttccaaag  1020
agccaacaag ccacaaccaa aaccacactc acaggtctga ggcccgggaac tgaatatggg  1080 attggagttt ctgctgtgaa ggaagacaag gagagcaatc cagcgaccat caacgcagcc  1140
acagagttgg acacgcccaa ggaccttcag gtttctgaaa ctgcagagac cagcctgacc  1200
ctgctctgga gagacaccgt tggccaaattt gaccgctacc gcctcaatta cagtctcccc  1260
```

```
acaggccagt gggtgggagt gcagcttcca agaaacacca cttcctatgt cctgagaggc    1320
ctggaaccag gacaggagta caatgtcctc ctgacagccg agaaaggcag acacaagagc    1380
aagcccgcac gtgtgaaggc atccactgaa caagccgcca tgggctcccc aaaggaagtc    1440
attttctcag acatcactga aaattcggct actgtcagct ggagggcacc cacagcccaa    1500
gtggagagct tccggattac ctatgtgccc attacaggag gtacaccctc catggtaact    1560
gtggacggaa ccaagactca gaccaggctg gtgaaactca tacctggcgt ggagtacctt    1620
gtcagcatca tcgccatgaa gggctttgag gaaagtgaac ctgtctcagg gtcattcacc    1680
acagctctgg atggcccatc tggcctggtg acagccaaca tcactgactc agaagccttg    1740
gccaggtggc agccagccat tgccactgtg gacagttatg tcatctccta cacaggcgag    1800
aaagtgccag aaattacacg cacggtgtcc gggaacacag tggagtatgc tctgaccgac    1860
ctcgagcctg ccacggaata cacactgaga atctttgcag agaaagggcc ccagaagagc    1920
tcaaccatca ctgccaagtt cacaacagac ctcgattctc caagagactt gactgctact    1980
gaggttcagt cggaaactgc cctccttacc tggcgacccc ccgggcatc agtcaccggt     2040 tacctgctgg tctatgaatc agtggatggc acagtcaagg aagtcattgt gggtccagat    2100
accacctcct acagcctggc agacctgagc ccatccaccc actacacagc caagatccag    2160
gcactcaatg gccccctgag gagcaatatg atccagacca tcttcaccac agtcgacctg    2220
gaagttctgt tccaggggcc cggctcaggc ctgaacgaca tcttcgaggc ccagaagatc    2280
gagtggcacg aggctcgagc tcaccaccat caccatcact ga    2322
```

```
<210> SEQ ID NO 107
<211> LENGTH: 19
<212> TYPE: PRT
<213> ORGANISM: Artificial Sequence
<220> FEATURE:
<223> OTHER INFORMATION: Leader Sequence 1

<400> SEQUENCE: 107

Met Asp Trp Thr Trp Arg Ile Leu Phe Leu Val Ala Ala Ala Thr Gly
1               5                   10                  15

Ala His Ser

<210> SEQ ID NO 108
<211> LENGTH: 57
<212> TYPE: DNA
<213> ORGANISM: Artificial Sequence
<220> FEATURE:
<223> OTHER INFORMATION: Leader Sequence 1 (DNA1)

<400> SEQUENCE: 108
atggactgga cctggagaat cctcttcttg gtggcagcag ccacaggagc ccactcc    57

<210> SEQ ID NO 109
<211> LENGTH: 57
<212> TYPE: DNA
<213> ORGANISM: Artificial Sequence
<220> FEATURE:
<223> OTHER INFORMATION: Leader Sequence 1 (DNA 2)

<400> SEQUENCE: 109
atggactgga cctggaggat cctcttcttg gtggcagcag ccacaggagc ccactcc    57

<210> SEQ ID NO 110
<211> LENGTH: 22
<212> TYPE: PRT
```

<213> ORGANISM: Artificial Sequence
<220> FEATURE:
<223> OTHER INFORMATION: Leader Sequence 2

<400> SEQUENCE: 110

Met Asp Met Arg Val Pro Ala Gln Leu Leu Gly Leu Leu Leu Leu Trp
1               5                   10                  15

Phe Pro Gly Ala Arg Cys
            20

<210> SEQ ID NO 111
<211> LENGTH: 66
<212> TYPE: DNA
<213> ORGANISM: Artificial Sequence
<220> FEATURE:
<223> OTHER INFORMATION: Leader Sequence 2 (DNA)

<400> SEQUENCE: 111
atggacatga gggtccccgc tcagctcctg ggcctcctgc tgctctggtt cccaggtgcc    60
aggtgt                                                              66

<210> SEQ ID NO 112
<211> LENGTH: 19
<212> TYPE: PRT
<213> ORGANISM: Artificial Sequence
<220> FEATURE:
<223> OTHER INFORMATION: Leader Sequence 3

<400> SEQUENCE: 112

Met Gly Trp Ser Cys Ile Ile Leu Phe Leu Val Ala Thr Ala Thr Gly
1               5                   10                  15

Val His Ser

<210> SEQ ID NO 113
<211> LENGTH: 57
<212> TYPE: DNA
<213> ORGANISM: Artificial Sequence
<220> FEATURE:
<223> OTHER INFORMATION: Leader Sequence 3 (DNA 1)

<400> SEQUENCE: 113
atgggatgga gctgtatcat cctcttcttg gtagcaacag ctaccggtgt gcattcc    57

<210> SEQ ID NO 114
<211> LENGTH: 57
<212> TYPE: DNA
<213> ORGANISM: Artificial Sequence
<220> FEATURE:
<223> OTHER INFORMATION: Leader Sequence 3 (DNA 1)

<400> SEQUENCE: 114
atgggctggt cctgcatcat cctgtttctg gtggctaccg ccactggagt gcattcc    57

<210> SEQ ID NO 115
<211> LENGTH: 57
<212> TYPE: DNA
<213> ORGANISM: Artificial Sequence
<220> FEATURE:
<223> OTHER INFORMATION: Leader Sequence 3 (DNA 3)

<400> SEQUENCE: 115
atgggctggt cctgcatcat cctgtttctg gtcgccacag ccaccggcgt gcactct    57

<210> SEQ ID NO 116

```
<211> LENGTH: 26
<212> TYPE: DNA
<213> ORGANISM: Artificial Sequence
<220> FEATURE:
<223> OTHER INFORMATION: LMB3

<400> SEQUENCE: 116
caggaaacag ctatgaccat gattac                                          26

<210> SEQ ID NO 117
<211> LENGTH: 63
<212> TYPE: DNA
<213> ORGANISM: Artificial Sequence
<220> FEATURE:
<223> OTHER INFORMATION: LibL1b_new
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 117
cactttggtc ccctggccga acgtmnnggg mnnmnnmnna ccctgctgac agtaatacac     60
tgc                                                                   63

<210> SEQ ID NO 118
<211> LENGTH: 28
<212> TYPE: DNA
<213> ORGANISM: Artificial Sequence
<220> FEATURE:
<223> OTHER INFORMATION: MS63

<400> SEQUENCE: 118
tttcgcacag taatatacgg ccgtgtcc                                        28

<210> SEQ ID NO 119
<211> LENGTH: 25
<212> TYPE: DNA
<213> ORGANISM: Artificial Sequence
<220> FEATURE:
<223> OTHER INFORMATION: MS64

<400> SEQUENCE: 119
acgttcggcc aggggaccaa agtgg                                           25

<210> SEQ ID NO 120
<211> LENGTH: 60
<212> TYPE: DNA
<213> ORGANISM: Artificial Sequence
<220> FEATURE:
<223> OTHER INFORMATION: Lib2H
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
```

```
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 120
ggccgtatat tactgtgcga aannknnknn knnknnkttt gactactggg gccaaggaac        60

<210> SEQ ID NO 121
<211> LENGTH: 30
<212> TYPE: DNA
<213> ORGANISM: Artificial Sequence
<220> FEATURE:
<223> OTHER INFORMATION: fdseqlong

<400> SEQUENCE: 121
gacgttagta aatgaatttt ctgtatgagg                                         30

<210> SEQ ID NO 122
<211> LENGTH: 69
<212> TYPE: DNA
<213> ORGANISM: Artificial Sequence
<220> FEATURE:
<223> OTHER INFORMATION: RJH_LIB3
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t

<400> SEQUENCE: 122
gactttggtg ccctggccaa acgtmnnggg mnnmnnaccm nnctgcaagc agtaataggt        60
ggcaaaatc                                                                69

<210> SEQ ID NO 123
<211> LENGTH: 27
<212> TYPE: DNA
<213> ORGANISM: Artificial Sequence
<220> FEATURE:
<223> OTHER INFORMATION: RJH31

<400> SEQUENCE: 123
acgtttggcc agggcaccaa agtcgag                                            27

<210> SEQ ID NO 124
<211> LENGTH: 28
<212> TYPE: DNA
<213> ORGANISM: Artificial Sequence
<220> FEATURE:
<223> OTHER INFORMATION: RJH32
```

```
<400> SEQUENCE: 124
tctcgcacag taatacacgg cggtgtcc                                         28

<210> SEQ ID NO 125
<211> LENGTH: 94
<212> TYPE: DNA
<213> ORGANISM: Artificial Sequence
<220> FEATURE:
<223> OTHER INFORMATION: LIB88_2
<220> FEATURE:
<221> NAME/KEY: misc_difference
<222> LOCATION: (29)..(55)
<223> OTHER INFORMATION: (33% GAC Asp; 26% GGT Gly; 10% GAA Glu; 9% CGT
      Arg; 7% Lys; 6% GTT Val; 5% TCT Ser; 4% CTG Leu)1 - (23% GGT Gly;
      17% TAC Tyr; 16% TCT Ser; 11% GCT Ala; 9% CGT Arg; 7% AAC Asn; 6%
      ACT Thr; 6% GTT Val; 5% CCG Pro)8
<220> FEATURE:
<221> NAME/KEY: misc_feature
<222> LOCATION: (30)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 125
ggacaccgcc gtgtattact gtgcgagabn nnnbnnbnnb nnbnnbnnbn nbnnbtttga       60
ctactggggc caagggacca ccgtgaccgt ctcc                                  94

<210> SEQ ID NO 126
<211> LENGTH: 63
<212> TYPE: DNA
<213> ORGANISM: Artificial Sequence
<220> FEATURE:
<223> OTHER INFORMATION: AM_Vk1A30_L1_ba

<400> SEQUENCE: 126
cctggcttct gctggtacca gcctaaatca ttacgaatgc cctgacttgc ccggcaggtg      60
atg                                                                   63

<210> SEQ ID NO 127
<211> LENGTH: 27
<212> TYPE: DNA
<213> ORGANISM: Artificial Sequence
<220> FEATURE:
<223> OTHER INFORMATION: RJH50(Vk1A30_L1/L2_fo)
```

<400> SEQUENCE: 127
gctggtacca gcagaagcca gggaaag                                27

<210> SEQ ID NO 128
<211> LENGTH: 26
<212> TYPE: DNA
<213> ORGANISM: Artificial Sequence
<220> FEATURE:
<223> OTHER INFORMATION: RJH51(Vk1A30_BsiWI_ba)

<400> SEQUENCE: 128
ggtgcagcca ccgtacgctt gatctc                                 26

<210> SEQ ID NO 129
<211> LENGTH: 61
<212> TYPE: DNA
<213> ORGANISM: Artificial Sequence
<220> FEATURE:
<223> OTHER INFORMATION: AM_Vk1A30_L2_ba

<400> SEQUENCE: 129
cttgatggga cgccactctg caaactggac gcagcataga tcaggcgctt aggggctttc    60
c                                                            61

<210> SEQ ID NO 130
<211> LENGTH: 27
<212> TYPE: DNA
<213> ORGANISM: Artificial Sequence
<220> FEATURE:
<223> OTHER INFORMATION: RJH52(Vk1A30_L2/L3)

<400> SEQUENCE: 130
ttgcagagtg gcgtcccatc aaggttc                                27

<210> SEQ ID NO 131
<211> LENGTH: 26
<212> TYPE: DNA
<213> ORGANISM: Artificial Sequence
<220> FEATURE:
<223> OTHER INFORMATION: RJH53

<400> SEQUENCE: 131
catcagggcc tgagctcgcc cgtcac                                 26

<210> SEQ ID NO 132
<211> LENGTH: 62
<212> TYPE: DNA
<213> ORGANISM: Artificial Sequence
<220> FEATURE:
<223> OTHER INFORMATION: AM_DP88_H1_ba_opt

<400> SEQUENCE: 132
gtccaggggc ctgtcgcacc cagcttatag cgtagctgct gaatgtgcct ccggaggcct    60
tg                                                           62

<210> SEQ ID NO 133
<211> LENGTH: 28
<212> TYPE: DNA
<213> ORGANISM: Artificial Sequence
<220> FEATURE:
<223> OTHER INFORMATION: RJH54(DP88_H1/H2_fo)

<400> SEQUENCE: 133
ataagctggg tgcgacaggc ccctggac                               28

```
<210> SEQ ID NO 134
<211> LENGTH: 26
<212> TYPE: DNA
<213> ORGANISM: Artificial Sequence
<220> FEATURE:
<223> OTHER INFORMATION: MS52

<400> SEQUENCE: 134
gaagaccgat gggcctttgg tgctag                                        26

<210> SEQ ID NO 135
<211> LENGTH: 83
<212> TYPE: DNA
<213> ORGANISM: Artificial Sequence
<220> FEATURE:
<223> OTHER INFORMATION: AM_DP88_H2_ba

<400> SEQUENCE: 135
gaccctgccc tggaacttct gtgcgtagtt tgcggtacca aagatagggga tgatccctcc  60 catccactcg agcccttgtc cag                                           83

<210> SEQ ID NO 136
<211> LENGTH: 29
<212> TYPE: DNA
<213> ORGANISM: Artificial Sequence
<220> FEATURE:
<223> OTHER INFORMATION: RJH55 (DP88_H2H3_fo)

<400> SEQUENCE: 136
tacgcacaga agttccaggg cagggtcac                                     29
```